US008501780B2

(12) United States Patent
Kerns et al.

(10) Patent No.: US 8,501,780 B2
(45) Date of Patent: *Aug. 6, 2013

(54) INDAZOLE CARBOXAMIDES AND THEIR USE

(75) Inventors: Jeffrey K. Kerns, King of Prussia, PA (US); Christine Edwards, Harlow Essex (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 1678 days.

This patent is subject to a terminal disclaimer.

(21) Appl. No.: 11/570,060

(22) PCT Filed: Jun. 24, 2005

(86) PCT No.: PCT/US2005/022870
§ 371 (c)(1),
(2), (4) Date: Dec. 5, 2006

(87) PCT Pub. No.: WO2006/002434
PCT Pub. Date: Jan. 5, 2006

(65) Prior Publication Data
US 2007/0281933 A1 Dec. 6, 2007

Related U.S. Application Data

(60) Provisional application No. 60/582,655, filed on Jun. 24, 2004.

(51) Int. Cl.
*A61K 31/445* (2006.01)
*C07D 401/14* (2006.01)

(52) U.S. Cl.
USPC ........... 514/322; 514/212; 514/255; 514/323; 514/412; 514/422; 540/602; 544/373; 546/199; 546/201; 548/469

(58) Field of Classification Search
USPC .. 514/212, 255, 322, 323, 412, 422; 540/602; 544/373; 546/199, 201; 548/469
See application file for complete search history.

(56) References Cited

U.S. PATENT DOCUMENTS

| 4,775,761 | A | 10/1988 | Strupczewski | 546/199 |
|---|---|---|---|---|
| 5,026,856 | A | 6/1991 | Yatsunami et al. | 546/156 |
| 5,254,473 | A | 10/1993 | Patel | 436/1 |
| 5,256,673 | A | 10/1993 | Böttcher et al. | 514/338 |
| 5,330,986 | A | 7/1994 | Shutske | 514/252.19 |
| 5,861,414 | A * | 1/1999 | Allen et al. | 514/316 |
| 6,245,799 | B1 | 6/2001 | Asselin et al. | 514/414 |
| 6,358,994 | B1 | 3/2002 | Fritz et al. | 514/220 |
| 6,509,340 | B1 | 1/2003 | Van Amsterdam et al. | 514/252.11 |
| 6,589,954 | B1 | 7/2003 | Mavunkel et al. | 514/254.06 |
| 6,787,535 | B2 | 9/2004 | Beard et al. | 514/183 |
| 6,897,231 | B2 * | 5/2005 | Bhagwat et al. | 514/403 |
| 6,919,335 | B2 | 7/2005 | Iwanowicz et al. | 514/230.5 |
| 7,176,231 | B2 | 2/2007 | Heckel et al. | 514/418 |
| 7,186,743 | B2 * | 3/2007 | Bergmanis et al. | 514/406 |
| 7,214,699 | B2 * | 5/2007 | Cournoyer et al. | 514/403 |
| 7,375,219 | B2 | 5/2008 | Maddaford et al. | 540/524 |
| 2002/0103229 | A1 | 8/2002 | Bhagwat et al. | 514/338 |
| 2002/0147189 | A1 | 10/2002 | Cai et al. | 514/217.06 |
| 2002/0161004 | A1 | 10/2002 | Browner et al. | 514/228.2 |
| 2003/0022898 | A1 | 1/2003 | Burke et al. | 514/250 |
| 2005/0009876 | A1 * | 1/2005 | Bhagwat et al. | 514/338 |
| 2005/0153966 | A1 | 7/2005 | Gangloff et al. | 514/243 |
| 2005/0165086 | A1 | 7/2005 | Callahan et al. | 514/443 |
| 2006/0116419 | A1 | 6/2006 | Callahan et al. | 514/447 |
| 2007/0254873 | A1 * | 11/2007 | Kerns et al. | 514/228.8 |
| 2007/0281933 | A1 | 12/2007 | Kerns et al. | 514/234.5 |
| 2007/0282101 | A1 * | 12/2007 | Ericsson et al. | 544/119 |

(Continued)

FOREIGN PATENT DOCUMENTS
DE 3342632 6/1985
DE 19500689 7/1996

(Continued)

OTHER PUBLICATIONS

U.S. Appl. No. 10/597,154, Dated Jan. 13, 2005, Baldwin et al.

(Continued)

*Primary Examiner* — Celia Chang
(74) *Attorney, Agent, or Firm* — Nora L. Stein; Theodore R. Furman

(57) ABSTRACT

The invention is directed to novel indazole carboxamide derivatives. Specifically, the invention is directed to compounds according to Formula I:

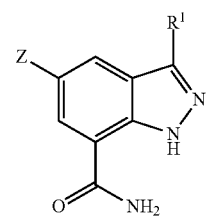

wherein R1 and Z are defined below, and to pharmaceutically-acceptable salts thereof.

The compounds of the invention are inhibitors of IKK2 and can be useful in the treatment of disorders associated with inappropriate IKK2 (also known as IKKβ) activity, such as rheumatoid arthritis, asthma, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

5 Claims, No Drawings

U.S. PATENT DOCUMENTS

| | | | |
|---|---|---|---|
| 2008/0146606 A1 | 6/2008 | Bamborough et al. | 514/300 |
| 2008/0242685 A1 | 10/2008 | Kerns et al. | 514/265.1 |
| 2008/0262040 A1* | 10/2008 | Callahan et al. | 514/322 |
| 2008/0269200 A1* | 10/2008 | Baldwin et al. | 514/217.08 |
| 2008/0269291 A1* | 10/2008 | Kerns et al. | 514/323 |
| 2008/0293802 A1 | 11/2008 | Kerns et al. | 514/419 |
| 2009/0030014 A1 | 1/2009 | Kugimiya et al. | 514/254.08 |
| 2009/0099178 A1* | 4/2009 | Bhagwat et al. | 514/234.5 |
| 2009/0143372 A1* | 6/2009 | Deng et al. | 514/228.2 |
| 2010/0130468 A1 | 5/2010 | Busch-Petersen et al. | 514/210.21 |
| 2010/0179139 A1 | 7/2010 | Bamborough et al. | 514/228.2 |

FOREIGN PATENT DOCUMENTS

| | | |
|---|---|---|
| DE | 19807993 | 9/1999 |
| DE | 19928424 | 12/2000 |
| DE | 10112151 | 9/2002 |
| DE | 10259244 | 7/2004 |
| EP | 279263 | 8/1993 |
| EP | 0556949 A2 | 8/1993 |
| EP | 610134 | 8/1994 |
| EP | 416609 | 1/1997 |
| EP | 0812826 | 12/1997 |
| EP | 1077213 | 2/2001 |
| EP | 1134221 | 9/2001 |
| EP | 1209158 | 5/2002 |
| JP | A-60-132980 | 7/1985 |
| JP | A-2002-533333 | 10/2002 |
| WO | WO94/21627 | 9/1994 |
| WO | WO94/21630 | 9/1994 |
| WO | WO96/40115 | 12/1996 |
| WO | WO97/44319 | 11/1997 |
| WO | WO98/06715 | 2/1998 |
| WO | WO98/28292 | 7/1998 |
| WO | WO99/43652 | 2/1999 |
| WO | WO99/17773 | 4/1999 |
| WO | WO00/00487 | 1/2000 |
| WO | WO01/00610 | 1/2001 |
| WO | WO01/30774 | 5/2001 |
| WO | WO01/34598 | 5/2001 |
| WO | WO01/58890 | 8/2001 |
| WO | WO01/68648 | 9/2001 |
| WO | WO01/083472 | 11/2001 |
| WO | WO01/87298 | 11/2001 |
| WO | WO01/98290 | 12/2001 |
| WO | WO02/14317 | 2/2002 |
| WO | WO02/16353 | 2/2002 |
| WO | WO02/24679 | 3/2002 |
| WO | WO02/24693 | 3/2002 |
| WO | WO02/28860 | 3/2002 |
| WO | WO02/30353 | 4/2002 |
| WO | WO02/30423 | 4/2002 |
| WO | WO02/41843 | 5/2002 |
| WO | WO02/44153 | 6/2002 |
| WO | WO02/46171 | 6/2002 |
| WO | WO02/051837 | 7/2002 |
| WO | WO02/060386 | 8/2002 |
| WO | WO02/094265 | 11/2002 |
| WO | WO02/094322 | 11/2002 |
| WO | WO02/094813 | 11/2002 |
| WO | WO03/07076 | 1/2003 |
| WO | WO03/010158 | 2/2003 |
| WO | WO03/010163 | 2/2003 |
| WO | WO03/022898 | 3/2003 |
| WO | WO03/024935 | 3/2003 |
| WO | WO03/024936 | 3/2003 |
| WO | WO03/027075 | 4/2003 |
| WO | WO03/035625 | 5/2003 |
| WO | WO03/037886 | 5/2003 |
| WO | WO03/068193 A | 8/2003 |
| WO | WO03/084959 | 10/2003 |
| WO | WO03/087087 | 10/2003 |
| WO | WO03/095430 | 11/2003 |
| WO | WO03/101987 | 12/2003 |
| WO | WO03/103661 | 12/2003 |
| WO | WO03/104218 | 12/2003 |
| WO | WO2004/019935 | 3/2004 |
| WO | WO2004/022553 | 3/2004 |
| WO | WO2004/024730 | 3/2004 |
| WO | WO2004/024732 | 3/2004 |
| WO | WO2004/024736 | 3/2004 |
| WO | WO2004/047760 | 6/2004 |
| WO | WO2004/075846 | 9/2004 |
| WO | WO2004/089913 | 10/2004 |
| WO | WO2004/106293 | 12/2004 |
| WO | WO2005/012283 | 2/2005 |
| WO | WO2005/035527 | 4/2005 |
| WO | WO2005/035537 | 4/2005 |
| WO | WO2005/067923 | 7/2005 |
| WO | WO2006/002434 | 1/2006 |
| WO | WO 2006/034317 | 3/2006 |
| WO | WO2006/106326 | 10/2006 |
| WO | WO2007/005534 | 1/2007 |
| WO | WO2007/010964 | 1/2007 |
| WO | WO2007/114848 | 10/2007 |
| WO | WO2009/112473 | 9/2009 |
| WO | WO2010/102968 | 9/2010 |
| WO | WO2010/106016 | 9/2010 |

OTHER PUBLICATIONS

U.S. Appl. No. 11/931,189, Dated Oct. 31, 2007, Deng et al.
U.S. Appl. No. 12/093,750, Dated May 15, 2005, Kerns et al.
U.S. Appl. No. 12/093,750, Dated May 15, 2008, Kerns et al.
U.S. Appl. No. 12/096,397, Dated Jun. 6, 2008, Kerns et al.
U.S. Appl. No. 12/532,773, Dated May 27, 2010, Bush-Petersen et al.
Aupperle et al., "NF-κB Regulation by Iκb Kinase in Primary Fibroblast-Like Synoviocytes" *J. Immunology* (1999) 163:427-433.
Aupperles. J. Immunology 2001; 166: 2705-11.
Aupperle et al., "NF-R13 Regulation by IκB Kinase-2 in Rheumatoid Arthritis Synoviocytes" *J. Immunology* (2001) 166:31496-31501.
Baxter, Bioorg. Med. Chem. Lett., 14, 2817-2822 (2004).
Breton et al., "The Natural Product Hymenialdisine Inhibits Interleukin-8 Production in U937 Cells by Inhibition of Nuclear Factor-κB" JPET (1997) 282(1):459-466.
Burke et al., "BMS-345541 Is a Highly Selective Inhibitor of IκB Kinase That Binds at an Allosteric Site of the Enzyme and Blocks NF-κB-dependent Transcription in Mice" *J. Biol Chem.* (2003) 278:1450-1456.
Guttridge et al., "Nf-κb-Induced Loss of MyoD Messenger RNA: Possible Role in Muscle Decay and Cachexia" *Science* (2000) 289:2363-2365.
Micallef., et al.: "Brominated isoindolines: Precursors to functionalised nitroxides", Journal of the Chemical Society; Perkin 2, (001), 65 and 72, 1999.
Miller, et al: "3,5-Disubstituted-indole-7-carboxamides: The Discovery of a novel series of potent, selective inhibitors of IKK-β". Bioorganic & Medicine Chemistry Letters 21 (2011) 2255-2258.
Murata et al., "Discovery of novel and selective IKK-β serine-threonine protein kinase inhibitors. Part 1." *Bioorg. Med. Chem. Letter* (2003) 13:913-198.
Murata et al., "Synthesis and structure—activity relationships of novel IKK-β inhibitors. Part 2: Improvement of in vitro activity" *Bioorg. Med. Chem. Letter* (2004) 14(15):4013-4017.
Murata, et al. "Synthesis and structure—activity relationships of novel IKK-β inhibitors. Part 3: Orally active anti-inflammatory agents," *Bioorg. Med. Chem. Letter* (2004) 14(15):4019-4022.
Peet et al., "IκB Kinases α and β Show a Random Sequential Kinetic Mechanism and Are Inhibited by Staurosporine and Quercetin" *J. Biol. Chem.* (1999) 274:32655-32661.
Pierce, et al., "Novel Inhibitors of Cytokine-induced IkBec Phosphorylation and Endothelial Cell Adhesion Molecule Expression Show Anti-inflammatory Effects in Vivo" J. Biol. Chem. (1997) 272:21096-21103.
Tyle, Pharmaceutical Research, 1986, vol. 3, No. 6, pp. 318-326.
TW Green, Protecting Groups in organic Synthesis; PG M Wuts, John Wiley & Sons, 1991.
Roshak, et al., "Inhibition of NfκB-Mediated Interleukin-1$^\beta$-Stimulated Prostaglandin $E_2$ Formation by the Marine Natural Product Hymenialdisine" *JPET* (1997) 283(2):955-961.

Roshak, et al., "Manipulation of Distinct NfκB Proteins Alters Interleukin-1β-induced Human Rheumatoid Synovial Fibroblast Prostaglandin E2 Formation" *J. Biol. Chem.* (1996) 271:31496-31501.

Sullivan et al., "2-Chloro-4-(trifluoromethyl)pyrimidine-5-N-(3',5'-bis(trifluoromethyl)phenyl)- carboxamide: A Potent Inhibitor of NF-κb- and AP-1-Mediated Gene Expression Identified Using Solution-Phase Combinatorial Chemistry" J. Med. Chem. (1998) 41:413-419.

Stereochemistry of Organic Compounds, TW Green, P G M Wuts, E L ELeil, S H Wile, L N Mander, Wiley-Interscience, 1994.

Tak et al., "Inhibitor of nuclear factor κb kinase $^\beta$ is a key regulator of synovial inflammation" *Arthritis and Rheumatism* (2001) 44(8):1897-1907.

Wahl et al., "Sulfasalazine: a potent and specific inhibitor of nuclear factor kappa B" *J. Clin. Invest.* (1998) 101(5):1163-1174.

Wisniewski et al., "Assay for IκB Kinases Using an in Vivo Biotinylated IκB Protein Substrate" *Analytical Biochem.* (1999) 274:220-228.

Boettcher, et al., Abstract No. 98323-88-7 (Sep. 29, 1985).

Baldwin, CA 143:172 754 (Jul. 2005).

Restriction Requirement dated May 20, 2009 in U.S. Appl. No. 10/597,154.

Official Action dated Oct. 27, 2009 in U.S. Appl. No. 10/597,154.

Final Action dated Jul. 15, 2010 in U.S. Appl. No. 10/597,154.

Final Action dated May 14, 2009 in U.S. Appl. No. 11/575,416.

Official Action dated Jan. 4, 2010 in U.S. Appl. No. 11/575,416.

Notice of Allowance dated Aug. 11, 2010 in U.S. Appl. No. 11/575,416.

Restriction dated Apr. 6, 2010 in U.S. Appl. No. 11/931,189.

Official Action dated Aug. 23, 2010 in U.S. Appl. No. 11/931,189.

Notice of Allowance dated Jan. 31, 2011 in U.S. Appl. No. 11/931,189.

Notice of Allowance dated Jul. 14, 2011 in U.S. Appl. No. 11/931,189.

Restriction Requirement dated Aug. 26, 2010 in U.S. Appl. No. 12/093,750.

Official Action dated Dec. 16, 2010 in U.S. Appl. No. 12/093,750.

Official Action dated Jun. 2, 2011 in U.S. Appl. No. 12/093,750.

Official Action dated May 26, 2011 in U.S. Appl. No. 12/096,397.

Notice of Allowance dated Mar. 14, 2011 in U.S. Appl. No. 12/532,773.

* cited by examiner

INDAZOLE CARBOXAMIDES AND THEIR USE

This application is a 371 of International Application No. PCT/US2005/022870, filed 24 Jun. 2005, which claims benefit of U.S. Provisional Application No. 60/582,655, filed 24 Jun. 2004.

FIELD OF THE INVENTION

The invention is directed to certain indazole carboxamide compounds, which are inhibitors of kinase activity. More specifically, the compounds are IKK2 inhibitors. These compounds are useful in the treatment of disorders associated with inappropriate IKK2 (also known as IKKβ activity, in particular in the treatment and prevention of disorders mediated by IKK2 mechanisms including inflammatory and tissue repair disorders. Such disorders include rheumatoid arthritis, asthma, and COPD (chronic obstructive pulmonary disease).

BACKGROUND OF THE INVENTION

An important large family of enzymes is the protein kinase enzyme family. Currently, there are about 500 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the γ-phosphate of the ATP-$Mg^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied families of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

Nuclear factor κB (NF-κB) belongs to a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing migration of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), environmental and oxidative stress and DNA damaging agents. Apparently common to all stimuli however, is the phosphorylation and subsequent degradation of IκB. IκB is phosphorylated on two N-terminal serines by the recently identified IκB kinases (IKK-α and IKK-β). IKK-β is also known as IKK2. Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines and chemokines, cell adhesion molecules, acute phase proteins, immunoregulatory proteins, eicosanoid metabolizing enzymes and anti-apoptotic genes.

It is well-known that NF-κB plays a key role in the regulated expression of a large number of pro-inflammatory mediators including cytokines such as TNF, IL-1β, IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB.

Further evidence for a role of NF-κB in inflammatory disorders comes from studies of rheumatoid synovium.

Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α or IL-1β. Such a distribution may be the underlying mechanism for the increased cytokine and eicosanoid production characteristic of this tissue. See Roshak, A. K., et al., *J. Biol. Chem.*, 271, 31496-31501 (1996). Expression of IKK-β has been shown in synoviocytes of rheumatoid arthritis patients and gene transfer studies have demonstrated the central role of IKK-β in stimulated inflammatory mediator production in these cells. See Aupperele et al. *J. Immunology* 1999. 163:427-433 and Aupperle et al. *J. Immunology* 2001; 166:2705-11. More recently, the intra-articular administration of a wild type IKK-β adenoviral construct was shown to cause paw swelling while intra-articular administration of dominant-negative IKKβ inhibited adjuvant-induced arthritis in rat. See Tak et al. *Arthritis and Rheumatism* 2001, 44:1897-1907.

The NF-κB/Rel and IκB proteins are also likely to play a key role in neoplastic transformation and metastasis. Family members are associated with cell transformation in vitro and in vivo as a result of over expression, gene amplification, gene rearrangements or translocations. In addition, rearrangement and/or amplification of the genes encoding these proteins are seen in 20-25% of certain human lymphoid tumors. Further, NF-κB is activated by oncogenic ras, the most common defect in human tumors and blockade of NF-κB activation inhibits ras mediated cell transformation. In addition, a role for NF-κB in the regulation of apoptosis has been reported strengthening the role of this transcription factor in the regulation of tumor cell proliferation. TNF, ionizing radiation and DNA damaging agents have all been shown to activate NF-κB which in turn leads to the upregulated expression of several anti-apoptotic proteins. Conversely, inhibition of NF-κB has been shown to enhance apoptotic-killing by these agents in several tumor cell types. As this likely represents a major mechanism of tumor cell resistance to chemotherapy, inhibitors of NF-κB activation may be useful chemotherapeutic agents as either single agents or adjunct therapy. Recent reports have implicated NF-κB as an inhibitor of skeletal cell differentiation as well as a regulator of cytokine-induced muscle wasting (Guttridge et al. *Science;* 2000; 289: 2363-2365) further supporting the potential of NF-κB inhibitors as novel cancer therapies.

Several NF-κB inhibitors are described in C. Wahl, et al. *J. Clin. Invest.* 101 (5), 1163-1174 (1998), R. W. Sullivan, et al. *J. Med. Chem.* 41, 413-419 (1998), J. W. Pierce, et al. *J. Biol. Chem.* 272, 21096-21103 (1997).

The marine natural product hymenialdisine is known to inhibit NF-☐B. Roshak, A., et al., *JPET*, 283, 955-961 (1997). Breton, J. J and Chabot-Fletcher, M. C., *JPET*, 282, 459-466 (1997).

Additionally, patent applications have been filed on aminothiophene inhibitors of the IKK2, see Callahan, et al., WO 2002030353; Baxter, et al., WO 2001058890, Faull, et al., WO 2003010158; Griffiths, et al., WO 2003010163; Fancelli, et al., WO 200198290; imidazole inhibitors of IKK2, see Callahan, et al., WO 200230423; anilinophenylpyrimidine inhibitors of IKK2, see Kois, et al., WO 2002046171; β-carboline inhibitors of IKK2, see Ritzeler, et al, WO 2001068648, Ritzeler, et al., EP 1134221; Nielsch, et al. *DE* 19807993; Ritzeler, et al., EP 1209158; indole inhibitors of IKK2, see Ritzeler, et al., WO 2001030774; benzimidazole inhibitors of the IKK2, see Ritzeler, et al., *DE* 19928424; Ritzeler et al., WO 2001000610; Ritzeler, et al., WO 2004022553; aminopyridine inhibitors of IKK2, see Lowinger, et al, WO 2002024679; Murata, et al., WO 2002024693; Murata, et al., WO 2002044153; pyrazolaquinazoline inhibitors of IKK2, see Beaulieu, et al., WO 2002028860; Burke et al., WO 2002060386, Burke, et al. US 20030022898; quinoline inhibitors of IKK2, Browner, et al., WO 2002041843, Browner, et al., US 20020161004 and pyridylcyanoguanidine inhibitors of IKK2, see Bjorkling, et al., WO 2002094813, Binderup et al., WO 2002094322 and Madsen, et al., WO 200294265; pyrazole inhibitors of IKK2, see Lennon, et al., WO 2003095430, Geng, et al., WO 2003027075, Xu, et al., WO 2003070706, Bermanis, et al., WO 2003024935. The natural products staurosporine, quercetin, K252a and K252b have been shown to be IKK2 inhibitors, see Peet, G. W. and Li, J. J. *Biol. Chem.*, 274, 32655-32661 (1999) and Wisniewski, D., et al., *Analytical Biochem.* 274, 220-228 (1999). Synthetic inhibitors of IKK2 have also been described, see Burke, et al. *J. Biol. Chem.*, 278, 1450-1456 (2003), Baxter, et al., *Bioorg. Med. Chem. Lett.*, 14, 2817-2822 (2004), and Murata, et al., *Bioorg. Med. Chem. Lett.*, 13, 913-198 (2003) have described IKK2 inhibitors.

Thus, attempts have been made to prepare compounds that inhibit IKK2 activity and a number of such compounds have been disclosed in the art. However, in view of the number of pathological responses that are mediated by IKK2, there remains a continuing need for inhibitors of IKK2 which can be used in the treatment of a variety of conditions.

SUMMARY OF THE INVENTION

The invention is directed to novel indazole carboxamide derivatives. Specifically, the invention is directed to compounds according to Formula I:

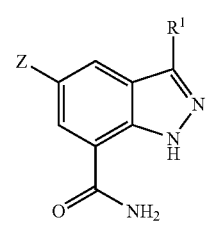

wherein R1 and Z are defined below, and to pharmaceutically-acceptable salts thereof.

The compounds of the invention are inhibitors of IKK2 and can be useful in the treatment of disorders associated with inappropriate IKK2 (also known as IKKβ) activity, such as rheumatoid arthritis, asthma, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

DETAILED DESCRIPTION OF THE INVENTION

In describing the invention, chemical elements are identified in accordance with the Periodic Table of the Elements. Abbreviations and symbols utilized herein are in accordance with the common usage of such abbreviations and symbols by those skilled in the chemical and biological arts. Specifically, the following abbreviations may be used in the examples and throughout the specification:

g (grams); mg (milligrams);
L (liters); mL (milliliters);
µL (microliters); psi (pounds per square inch);
M (molar); mM (millimolar);
i. v. (intravenous); Hz (Hertz);
MHz (megahertz); mol (moles);
mmol (millimoles); rt (room temperature);
min (minutes); h (hours);
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid;
EDC (1-[3-dimethylamino)propyl]-3-ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluroniumhexafluoro phosphate).
HEPES (4-(2-hydroxyethyl)-1-piperazine ethane sulfonic acid);
DPPA (diphenylphosphoryl azide);
fHNO$_3$ (fuming HNO$_3$); and
EDTA (ethylenediaminetetraacetic acid).
TMEDA (N,N,N',N'-tetramethyl-1,2-ethanediamine)
NBS (N-bromosuccinimide)
HATU (O-(7azabenzobenzotriazol-1-yl)-N,N N',N'-tetramethyluronium hexa-fluorophosphate)
DIPEA (diisopropylethylamine)
dppf (1,1'-bis(diphenylphosphino)ferrocene)
NIS (N-iodsuccinimide)

All references to ether are to diethyl ether and brine refers to a saturated aqueous solution of NaCl.

Terms and Definitions

"Alkyl" refers to a saturated hydrocarbon chain having the specified number of member atoms. For example, $C_1$-$C_6$ alkyl refers to an alkyl group having from 1 to 6 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkylene" refers to a saturated divalent hydrocarbon chain having the specified number of member atoms. For example, $C_1$-$C_6$ alkylene refers to an alkylene group having from 1 to 6 member atoms. Alkylene groups may be optionally substituted with one or more substituents as defined herein. Alkylene groups may be straight or branched. Representative branched alkylene groups have one, two, or three branches. Alkylene includes methylene, ethylene, propylene (n-propylene and isopropylene), butylene (n-butylene, isobutylene, and t-butylene), pentylene (n-pentylene, isopentylene, and neopentylene), and hexylene.

"Alkenyl" refers to an unsaturated hydrocarbon chain having the specified number of member atoms and having one or more carbon-carbon double bond within the chain. For example, $C_2$-$C_6$ alkenyl refers to an alkenyl group having from 2 to 6 member atoms. In certain embodiments alkenyl groups have one carbon-carbon double bond within the chain. In other embodiments, alkenyl groups have more than one carbon-carbon double bond within the chain. Alkenyl groups may be optionally substituted with one or more substituents as defined herein. Alkenyl groups may be straight or branched. Representative branched alkenyl groups have one, two, or three branches. Alkenyl includes ethylenyl, propenyl, butenyl, pentenyl, and hexenyl.

"Alkenylene" refers to an unsaturated divalent hydrocarbon chain having the specified number of member atoms and having one or more carbon-carbon double bond within the chain. For example, $C_2$-$C_6$ alkenylene refers to an alkenylene group having from 2 to 6 member atoms. In certain embodiments alkenylene groups have one carbon-carbon double bond within the chain. In other embodiments, alkenylene groups have more than one carbon-carbon double bond within the chain. Alkenylene groups may be optionally substituted with one or more substituents as defined herein. Alkenylene groups may be straight or branched. Representative branched alkenylene groups have one, two, or three branches. Alkenyl includes ethylenylene, propenylene, butenylene, pentenylene, and hexenylene.

"Alkynylene" refers to an unsaturated divalent hydrocarbon chain having the specified number of member atoms and having one or more carbon-carbon triple bond within the chain. For example, $C_2$-$C_6$ alkynylene refers to an alkynylene group having from 2 to 6 member atoms. In certain embodiments alkynylene groups have one carbon-carbon triple bond within the chain. In other embodiments, alkynylene groups have more than one carbon-carbon triple bond within the chain. For the sake of clarity, unsaturated divalent hydrocarbon chains having one or more carbon-carbon triple bond within the chain and one or more carbon-carbon double bond within the chain are alkynylene groups. Alkynylene groups may be optionally substituted with one or more substituents as defined herein. Alkynylene groups may be straight or branched. Representative branched alkynylene groups have one, two, or three branches. Alkynyl includes ethylynylene, propynylene, butynylene, pentynylene, and hexynylene.

"Aryl" refers to an aromatic hydrocarbon ring. Aryl groups are monocyclic ring systems or bicyclic ring systems. Monocyclic aryl ring refers to phenyl. Bicyclic aryl rings refer to napthyl and rings wherein phenyl is fused to a cycloalkyl or cycloalkenyl ring having 5, 6, or 7 member atoms. Aryl groups may be optionally substituted with one or more substituents as defined herein.

"Cycloalkyl" refers to a saturated hydrocarbon ring having the specified number of member atoms. Cycloalkyl groups are monocyclic ring systems. For example, $C_3$-$C_6$ cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

"Cycloalkenyl" refers to an unsaturated hydrocarbon ring having the specified number of member atoms and having a carbon-carbon double bond within the ring. For example, $C_3$-$C_6$ cycloalkenyl refers to a cycloalkenyl group having from 3 to 6 member atoms. In certain embodiments cycloalkenyl groups have one carbon-carbon double bond within the ring. In other embodiments, cycloalkenyl groups have more than one carbon-carbon double bond within the ring. However, cycloalkenyl rings are not aromatic. Cycloalkenyl groups are monocyclic ring systems. Cycloalkenyl groups may be optionally substituted with one or more substituents as defined herein. Cycloalkenyl includes cyclopropenyl, cyclobutenyl, cyclopentenyl, and cyclohexenyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct specie in vitro or in vivo.

"Halo" refers to the halogen radical fluoro, chloro, bromo, or iodo.

"Haloalkyl" refers to an alkyl group wherein at least one hydrogen atom attached to a member atom within the alkyl group is replaced with halo. Haloalkyl includes trifluoromethyl.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benopyranyl, benzoxazolyl, benzofuranyl, isobenzofuranyl, benzothiazolyl, benzothienyl, furopyridinyl, and napthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems having from 4 to 7 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, and azetidinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Compounds

The invention is directed to compounds according to Formula I:

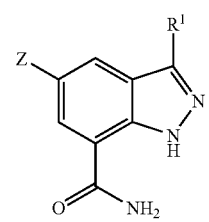

wherein:

Z is optionally substituted aryl or optionally substituted heteroaryl, wherein said aryl and heteroaryl are optionally substituted with one or more substituent independently selected from the group consisting of: halo, optionally substituted $C_1$-$C_6$ alkyl, optionally substituted $C_1$-$C_6$ haloalkyl, optionally substituted heterocycloalkyl, CN, N(Rb)SO$_2$Re, N(Rb)C(O)Ra, C(O)NRaRb, C(O)NRxRy, SO$_2$NRaRb, SO$_2$NRxRy, ORc, N(Rb)C(O)NRaRb, N(Rb)C(O)NRxRy, N(Rb)C(O)ORd, where said $C_1$-$C_6$ alkyl and $C_1$-$C_6$ haloalkyl are optionally substituted with one or more substituent selected from the group consisting of: NRaRb, $C_3$-$C_6$ cycloalkyl, ORc, phenyl, and heterocycloalkyl optionally substituted with one or two $C_1$-$C_6$ alkyl groups;

R1 is H, halo, or —WX;

W is a bond or $C_1$-$C_6$ alkylene;

X is optionally substituted aryl, optionally substituted heteroaryl, optionally substituted heterocycloalkyl, optionally substituted $C_4$-$C_7$ cycloalkyl, optionally substituted $C_5$-$C_7$ cycloalkenyl, N(Rb)SO$_2$Re, N(Rb)C(O)Re, N(Rb)C(O)ORd, N(Rb)C(O)NRaRb, or N(Rb)C(O)NRxRy, wherein said aryl, heteroaryl, heterocycloalkyl, $C_4$-$C_7$ cycloalkyl, and $C_5$-$C_7$ cycloalkenyl are optionally substituted with one or more substituent independently selected from the group consisting of: halo, optionally substituted $C_1$-$C_6$ alkyl, optionally substituted $C_1$-$C_6$ haloalkyl, ORc, C(O)Rg, C(O)ORf, N(Rb)SO$_2$Re, N(Rb)C(O)Ra, C(O)NRaRb, SO$_2$NRaRb, SO$_2$Re, and heterocycloalkyl, where said $C_1$-$C_6$ alkyl and $C_1$-$C_6$ haloalkyl are optionally substituted with one phenyl group;

each Ra is independently selected from the group consisting of: H, optionally substituted $C_1$-$C_3$ alkyl, optionally substituted phenyl, optionally substituted heteroaryl, optionally substituted $C_3$-$C_7$ cycloalkyl, and optionally substituted heterocycloalkyl, where said $C_1$-$C_3$ alkyl is optionally substituted with one or more substituent selected from the group consisting of: halo, ORc, $C_1$-$C_6$ haloalkyl, phenyl, and heteroaryl; and where said phenyl, heteroaryl, $C_3$-$C_7$ cycloalkyl, and heterocycloalkyl are optionally substituted with one or more substituent selected from the group consisting of: halo, ORc, $C_1$-$C_6$ alkyl, and $C_1$-$C_6$ haloalkyl;

each Rb is independently selected from the group consisting of: H and optionally substituted $C_1$-$C_3$ alkyl, where said $C_1$-$C_3$ alkyl is optionally substituted with one or more ORc groups;

each Rc is independently selected from the group consisting of: H, optionally substituted $C_1$-$C_6$ alkyl, optionally substituted $C_1$-$C_6$ haloalkyl, optionally substituted $C_3$-$C_7$ cycloalkyl, optionally substituted heterocycloalkyl, and optionally substituted aryl, optionally substituted heteroaryl, where said $C_1$-$C_6$ alkyl and $C_1$-$C_6$ haloalkyl are optionally substituted with one or more substituent selected from the group consisting of: $C_3$-$C_6$ cycloalkyl, phenyl, heterocycloalkyl, and heteroaryl; and where said aryl and heteroaryl are optionally substituted with one or more substituent selected from the group consisting of: halo, $C_1$-$C_3$ alkyl, $C_1$-$C_3$ haloalkyl and OH; and where said $C_3$-$C_7$ cycloalkyl and heterocycloalkyl are optionally substituted with one or more $C_1$-$C_3$ alkyl groups;

each Rd is independently optionally substituted $C_1$-$C_3$ alkyl, where said $C_1$-$C_3$ alkyl is optionally substituted with one or more substituent selected from the group consisting of: $C_3$-$C_6$ cycloalkyl; phenyl optionally substituted with one or more substituent selected from the group consisting of: halo, $C_1$-$C_6$ alkyl, and $C_3$-$C_6$ cycloalkyl; and heteroaryl optionally substituted with one or more substituent selected from the group consisting of: halo, $C_1$-$C_6$ alkyl, and $C_3$-$C_6$ cycloalkyl;

each Re is independently selected from the group consisting of: optionally substituted $C_1$-$C_6$ alkyl, optionally substituted phenyl, optionally substituted heteroaryl, optionally substituted $C_5$-$C_7$ cycloalkyl, and optionally substituted heterocycloalkyl, where said $C_1$-$C_6$ alkyl is optionally substituted with one substituent selected from the group consisting of: ORc, trifluoromethyl, phenyl, heteroaryl, heterocycloalkyl optionally substituted with ORc or heterocycloalkyl, and NRaRb; where said phenyl and heteroaryl are optionally substituted with one or more substituent selected from the group consisting of: halo, CN, $C_1$-$C_6$ alkyl, $C_1$-$C_6$ haloalkyl, N(Rb)C(O)Ra, and ORh; and where said $C_5$-$C_7$ cycloalkyl and heterocycloalkyl are optionally substituted with one or more substituent selected from the group consisting of: halo, $C_1$-$C_6$ alkyl optionally substituted with ORc, and $C_3$-$C_6$ cycloalkyl;

each Rf is independently selected from the group consisting of: H and optionally substituted $C_1$-$C_4$ alkyl, where said $C_1$-$C_4$ alkyl is optionally substituted with one or more substituent selected from the group consisting of: $C_3$-$C_6$ cycloalkyl; phenyl optionally substituted with one or more substituent selected from the group consisting of: halo, $C_1$-$C_6$ alkyl, and $C_3$-$C_6$ cycloalkyl; and heteroaryl optionally substituted with one or more substituent selected from the group consisting of: halo, $C_1$-$C_6$ alkyl, and $C_3$-$C_6$ cycloalkyl;

each Rg is independently selected from the group consisting of: optionally substituted $C_1$-$C_3$ alkyl, optionally substituted phenyl, optionally substituted heteroaryl, optionally substituted $C_3$-$C_7$ cycloalkyl, and optionally substituted heterocycloalkyl, where said $C_1$-$C_3$ alkyl is optionally substituted with one or more substituent selected from the group consisting of: halo and $C_{1-6}$ haloalkyl; and where said phenyl, heteroaryl, $C_3$-$C_7$ cycloalkyl, and heterocycloalkyl are optionally substituted with one or more substituent selected from the group consisting of: halo, $C_{1-6}$ alkyl, and $C_1$-$C_6$ haloalkyl;

each Rh is independently selected from the group consisting of: H, $C_1$-$C_6$ alkyl, and $C_1$-$C_6$ haloalkyl; and Rx and Ry taken together with the nitrogen atom to which they are attached form a ring having from 5 to 7 member atoms wherein said ring optionally contains one additional heteroatom as a member atom, said ring is saturated or unsaturated but not aromatic, and said ring is optionally substituted with one or two $C_1$-$C_3$ alkyl substituent.

The meaning of any functional group or substituent thereon at any one occurrence in Formula I, or any subformula thereof, is independent of its meaning, or any other functional group's or substituent's meaning, at any other occurrence, unless stated otherwise.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass any stereoisomer and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzamatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

The skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts impart greater stability or solubility to the molecule thereby facilitating formulation into a dosage form. Accordingly, the invention is further directed to pharmaceutically-acceptable salts of the compounds according to Formula I.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to Formula I may contain an acidic functional group. Suitable pharmaceutically-acceptable salts include salts of such acidic functional groups. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula I may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

As used herein, the terms "compounds" and "compounds of the invention" means both the compounds according to Formula I and the pharmaceutically-acceptable salts thereof. The terms "compound" and "a compound of the invention" also appears herein and refer to both a compound according to Formula I and its pharmaceutically-acceptable salts.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Representative Embodiments

As defined above, Z is optionally substituted aryl or optionally substituted heteroaryl. In one embodiment, Z is optionally substituted phenyl. In one embodiment, Z is unsubstituted phenyl. In another embodiment, Z is phenyl substituted with one or more substituent selected from the group consisting of: halo, N(Rb)SO$_2$Re, N(Rb)C(O)Ra, C(O)NRaRb, C(O)NRxRy, ORc, NRaRb, optionally substituted C$_1$-C$_6$ alkyl, optionally substituted C$_1$-C$_6$ haloalkyl, and optionally substituted heterocycloalkyl. In a yet another embodiment, Z is phenyl substituted with halo, di-halo, N(Rb)SO$_2$Re, N(Rb)C(O)Ra, ORc, or optionally substituted C$_1$-C$_6$ alkyl. In one embodiment wherein Z is phenyl substituted with optionally substituted C$_1$-C$_6$ alkyl, said C$_1$-C$_6$ alkyl is substituted with ORc, NRaRb, or heterocycloalkyl. In another embodiment wherein Z is phenyl substituted with optionally substituted C$_1$-C$_6$ alkyl, said C$_1$-C$_6$ alkyl is substituted with ORc or NRaRb.

In another embodiment, Z is optionally substituted heteroaryl. In one embodiment, Z is unsubstituted heteroaryl. In a further embodiment thereof, Z is monocyclic heteroaryl. In yet a further embodiment thereof, Z is pyrazolyl, thienyl, or pyrimidinyl optionally substituted with $C_1$-$C_6$ alkyl where said $C_1$-$C_6$ alkyl is optionally substituted with ORc, NRaRb or heterocycloalkyl. In yet a further embodiment thereof, Z is unsubstituted pyrazolyl, thienyl, or pyrimidinyl.

As defined above, R1 is H, halo, or —WX. In one embodiment R1 is —WX.

As defined above, —WX is a bond or $C_1$-$C_6$ alkylene. In one embodiment, R1 is —WX and W is a bond.

As defined above, X is optionally substituted aryl, optionally substituted heteroaryl, optionally substituted heterocycloalkyl, optionally substituted $C_4$-$C_7$ cycloalkyl, optionally substituted $C_5$-$C_7$ cycloalkenyl, N(Rb)SO$_2$Re, N(Rb)C(O)Re, N(Rb)C(O)ORd, N(Rb)C(O)NRaRb, or N(Rb)C(O)NRxRy.

In one embodiment, X is optionally substituted heterocycloalkyl. In a further embodiment thereof, X is optionally substituted piperidinyl. In one embodiment, X is unsubstituted piperidinyl. In another embodiment, X is piperidinyl substituted with C(O)Rg, C(O)ORf, or SO$_2$Re.

In one embodiment wherein X is piperidinyl substituted with C(O)Rg, Rg is optionally substituted $C_1$-$C_3$ alkyl or optionally substituted phenyl. In a further embodiment thereof, Rg is unsubstituted $C_1$-$C_3$ alkyl or unsubstituted phenyl. In yet another embodiment thereof wherein Rg is unsubstituted $C_1$-$C_3$ alkyl, Rg is methyl.

In one embodiment wherein X is piperidinyl substituted with C(O)ORf, Rf is optionally substituted $C_1$-$C_4$ alkyl. In a further embodiment thereof, Rf is t-butyl.

In one embodiment wherein X is piperidinyl substituted with SO$_2$Re, Re is optionally substituted $C_1$-$C_6$ alkyl, optionally substituted phenyl, or optionally substituted heteroaryl. In one embodiment, Re is unsubstituted $C_1$-$C_6$ alkyl. In another embodiment, Re is $C_1$-$C_6$ alkyl substituted with NRaRb or heterocycloalkyl. In one embodiment, Re is unsubstituted phenyl. In another embodiment, Re is phenyl substituted with one or more substituent selected from the group consisting of: halo, CN, N(Rb)C(O)Ra, and ORh. In one embodiment, Re is unsubstituted heteroaryl. In a further embodiment thereof, Re is thienyl. In another embodiment thereof, Re is unsubstituted imidazolyl. In yet another embodiment thereof, Re is imidazolyl substituted with $C_1$-$C_6$ alkyl.

In another embodiment wherein X is piperidinyl substituted with SO$_2$Re, Re is optionally substituted $C_1$-$C_3$ alkyl. In one embodiment, Re is unsubstituted $C_1$-$C_3$ alkyl. In another embodiment, Re is $C_1$-$C_3$ alkyl substituted with NRaRb. In a further embodiment thereof, Ra is H, optionally substituted $C_1$-$C_3$ alkyl, or optionally substituted $C_3$-$C_7$ cycloalkyl. In yet a further embodiment thereof, Ra is H, unsubstituted $C_1$-$C_3$ alkyl, or unsubstituted $C_3$-$C_7$ cycloalkyl. In yet further embodiment thereof, Ra is $C_1$-$C_3$ alkyl substituted with one or more ORc group or $C_3$-$C_7$ cycloalkyl substituted with one or more ORc group. In another embodiment, Re is $C_1$-$C_3$ alkyl substituted with heterocycloalkyl optionally substituted with ORc or heterocycloalkyl. In a further embodiment thereof, heterocycloalkyl is pyrrolidinyl, piperidinyl, piperazinyl, or morpholinyl optionally substituted with ORc or heterocycloalkyl. In yet a further embodiment thereof, heterocycloalkyl is pyrrolidinyl, piperidinyl, piperazinyl, or morpholinyl optionally substituted with OH or piperadinyl.

Specific examples of compounds of the present invention include the following:

1,1-dimethylethyl 4-[7-(aminocarbonyl)-5-phenyl-1H-indazol-3-yl]-1-piperidinecarboxylate;

5-phenyl-3-(4-piperidinyl)-1H-indazole-7-carboxamide;

3-[1-(ethylsulfonyl)-4-piperidinyl]-5-phenyl-1H-indazole-7-carboxamide;

5-phenyl-3-[1-(phenylcarbonyl)-4-piperidinyl]-1H-indazole-7-carboxamide;

3-{1-[(1-methyl-1H-imidazol-4-yl)sulfonyl]-4-piperidinyl}-5-phenyl-1H-indazole-7-carboxamide;

3-{1-[(4-fluorophenyl)sulfonyl]-4-piperidinyl}-5-phenyl-1H-indazole-7-carboxamide;

3-[1-(methylsulfonyl)-4-piperidinyl]-5-phenyl-1H-indazole-7-carboxamide;

3-(1-acetyl-4-piperidinyl)-5-phenyl-1H-indazole-7-carboxamide;

5-phenyl-3-[1-(phenylsulfonyl)-4-piperidinyl]-1H-indazole-7-carboxamide;

3-{1-[(1-methylethyl)sulfonyl]-4-piperidinyl}-5-phenyl-1H-indazole-7-carboxamide;

3-{1-[(1,2-dimethyl-1H-imidazol-4-yl)sulfonyl]-4-piperidinyl}-5-phenyl-1H-indazole-7-carboxamide;

3-{1-[(2-aminoethyl)sulfonyl]-4-piperidinyl}-5-phenyl-1H-indazole-7-carboxamide;

3-(1-{[4-(acetylamino)phenyl]sulfonyl}-4-piperidinyl)-5-phenyl-1H-indazole-7-carboxamide;

3-{1-[(4-cyanophenyl)sulfonyl]-4-piperidinyl}-5-phenyl-1H-indazole-7-carboxamide;

3-(1-{[3-(dimethylamino)propyl]sulfonyl}-4-piperidinyl)-5-phenyl-1H-indazole-7-carboxamide;

3-(1-{[2-(dimethylamino)ethyl]sulfonyl}-4-piperidinyl)-5-phenyl-1H-indazole-7-carboxamide;

3-{1-[(1,2-dimethyl-1H-imidazol-4-yl)sulfonyl]-4-piperidinyl}-5-{3-[(methylsulfonyl)amino]phenyl}-1H-indazole-7-carboxamide;

5-[3-(acetylamino)phenyl]-3-{1-[(1,2-dimethyl-1H-imidazol-4-yl)sulfonyl]-4-piperidinyl}-1H-indazole-7-carboxamide;

5-[4-(acetylamino)phenyl]-3-{1-[(1,2-dimethyl-1H-imidazol-4-yl)sulfonyl]-4-piperidinyl}-1H-indazole-7-carboxamide;

3-{1-[(1,2-dimethyl-1H-imidazol-4-yl)sulfonyl]-4-piperidinyl}-5-[4-(hydroxymethyl)phenyl]-1H-indazole-7-carboxamide;

3-{1-[(1,2-dimethyl-1H-imidazol-4-yl)sulfonyl]-4-piperidinyl}-5-(1H-pyrazol-4-yl)-1H-indazole-7-carboxamide;

3-(1-{[3-(dimethylamino)propyl]sulfonyl}-4-piperidinyl)-5-{4-[(trifluoromethyl)oxy]phenyl}-1H-indazole-7-carboxamide;

5-bromo-3-(1-{[3-(1-pyrrolidinyl)propyl]sulfonyl}-4-piperidinyl)-1H-indazole-7-carboxamide;

5-(1H-pyrazol-4-yl)-3-(1-{[3-(1-pyrrolidinyl)propyl]sulfonyl}-4-piperidinyl)-1H-indazole-7-carboxamide;

5-{4-[(methylsulfonyl)amino]phenyl}-3-(1-{[3-(1-pyrrolidinyl)propyl]sulfonyl}-4-piperidinyl)-1H-indazole-7-carboxamide;

5-{3-[(methylsulfonyl)amino]phenyl}-3-(1-{[3-(1-pyrrolidinyl)propyl]sulfonyl}-4-piperidinyl)-1H-indazole-7-carboxamide;

5-[4-(hydroxymethyl)phenyl]-3-(1-{[3-(1-pyrrolidinyl)propyl]sulfonyl}-4-piperidinyl)-1H-indazole-7-carboxamide;

5-[3-(hydroxymethyl)phenyl]-3-(1-{[3-(1-pyrrolidinyl)propyl]sulfonyl}-4-piperidinyl)-1H-indazole-7-carboxamide;

5-(3,4-difluorophenyl)-3-[1-(ethylsulfonyl)-4-piperidinyl]-1H-indazole-7-carboxamide;

5-(3,5-difluorophenyl)-3-[1-(ethylsulfonyl)-4-piperidinyl]-1H-indazole-7-carboxamide;

3-[1-(ethylsulfonyl)-4-piperidinyl]-5-(4-fluorophenyl)-1H-indazole-7-carboxamide;

3-[1-(ethylsulfonyl)-4-piperidinyl]-5-(2-fluorophenyl)-1H-indazole-7-carboxamide;
3-[1-(ethylsulfonyl)-4-piperidinyl]-5-(3-fluorophenyl)-1H-indazole-7-carboxamide;
5-(3-fluorophenyl)-3-(1-{[2-(1-pyrrolidinyl)ethyl]sulfonyl}-4-piperidinyl)-1H-indazole-7-carboxamide;
3-(1-{[2-(diethylamino)ethyl]sulfonyl}-4-piperidinyl)-5-(3-fluorophenyl)-1H-indazole-7-carboxamide;
3-(1-{[2-(cyclopentylamino)ethyl]sulfonyl}-4-piperidinyl)-5-(3-fluorophenyl)-1H-indazole-7-carboxamide;
3-(1-{[2-(1,4'-bipiperidin-1'-yl)ethyl]sulfonyl}-4-piperidinyl)-5-(3-fluorophenyl)-1H-indazole-7-carboxamide;
5-(3-fluorophenyl)-3-(1-{[2-(4-hydroxy-1-piperidinyl)ethyl]sulfonyl}-4-piperidinyl)-1H-indazole-7-carboxamide;
3-(1-{[3-(diethylamino)propyl]sulfonyl}-4-piperidinyl)-5-(3-fluorophenyl)-1H-indazole-7-carboxamide;
5-(3-fluorophenyl)-3-(1-{[3-(1-pyrrolidinyl)propyl]sulfonyl}-4-piperidinyl)-1H-indazole-7-carboxamide;
3-(1-{[3-(cyclopentylamino)propyl]sulfonyl}-4-piperidinyl)-5-(3-fluorophenyl)-1H-indazole-7-carboxamide;
3-(1-{[3-(1,4'-bipiperidin-1'-yl)propyl]sulfonyl}-4-piperidinyl)-5-(3-fluorophenyl)-1H-indazole-7-carboxamide;
5-(3-fluorophenyl)-3-(1-{[3-(4-hydroxy-1-piperidinyl)propyl]sulfonyl}-4-piperidinyl)-1H-indazole-7-carboxamide;
5-(3-fluorophenyl)-3-(1-{[3-(4-morpholinyl)propyl]sulfonyl}-4-piperidinyl)-1H-indazole-7-carboxamide;
3-[1-(ethylsulfonyl)-4-piperidinyl]-5-(2-thienyl)-1H-indazole-7-carboxamide;
3-[1-(ethylsulfonyl)-4-piperidinyl]-5-(3-thienyl)-1H-indazole-7-carboxamide;
3-(1-{[3-(1-pyrrolidinyl)propyl]sulfonyl}-4-piperidinyl)-5-(2-thienyl)-1H-indazole-7-carboxamide;
3-(1-{[3-(dimethylamino)propyl]sulfonyl}-4-piperidinyl)-5-(2-thienyl)-1H-indazole-7-carboxamide;
3-(1-{[3-(1-pyrrolidinyl)propyl]sulfonyl}-4-piperidinyl)-5-(3-thienyl)-1H-indazole-7-carboxamide;
3-(1-{[3-(dimethylamino)propyl]sulfonyl}-4-piperidinyl)-5-(3-thienyl)-1H-indazole-7-carboxamide;
3-[1-(ethylsulfonyl)-4-piperidinyl]-5-(3-pyridinyl)-1H-indazole-7-carboxamide;
3-(1-{[3-(4-morpholinyl)propyl]sulfonyl}-4-piperidinyl)-5-(2-thienyl)-1H-indazole-7-carboxamide;
3-(1-{[3-(4-morpholinyl)propyl]sulfonyl}-4-piperidinyl)-5-(3-thienyl)-1H-indazole-7-carboxamide;
3-(1-{[4-(methyloxy)phenyl]sulfonyl}-4-piperidinyl)-5-phenyl-1H-indazole-7-carboxamide;
5-phenyl-3-[1-(2-thienylsulfonyl)-4-piperidinyl]-1H-indazole-7-carboxamide;
5-phenyl-3-(1-{[3-(1-pyrrolidinyl)propyl]sulfonyl}-4-piperidinyl)-1H-indazole-7-carboxamide;
3-(1-{[3-(cyclobutylamino)propyl]sulfonyl}-4-piperidinyl)-5-phenyl-1H-indazole-7-carboxamide;
3-(1-{[3-(4-morpholinyl)propyl]sulfonyl}-4-piperidinyl)-5-phenyl-1H-indazole-7-carboxamide;
5-phenyl-3-(1-{[3-(1-piperazinyl)propyl]sulfonyl}-4-piperidinyl)-1H-indazole-7-carboxamide;
3-[1-({3-[3-(2-hydroxyethyl)-1-piperazinyl]propyl}sulfonyl)-4-piperidinyl]-5-phenyl-1H-indazole-7-carboxamide;
3-(1-{[3-(cyclopentylamino)propyl]sulfonyl}-4-piperidinyl)-5-phenyl-1H-indazole-7-carboxamide;
3-[1-({3-[(4-hydroxycyclohexyl)amino]propyl}sulfonyl)-4-piperidinyl]-5-phenyl-1H-indazole-7-carboxamide;
3-{1-[(3-{[2-hydroxy-1-(hydroxymethyl)ethyl]amino}propyl)sulfonyl]-4-piperidinyl}-5-phenyl-1H-indazole-7-carboxamide;
3-[1-(ethylsulfonyl)-4-piperidinyl]-5-{3-[(methylamino)methyl]phenyl}-1H-indazole-7-carboxamide;
5-{3-[(ethylamino)methyl]phenyl}-3-[1-(ethylsulfonyl)-4-piperidinyl]-1H-indazole-7-carboxamide and
5-[(methylamino)methyl]-3-(1-{[3-(methyloxy)propyl]sulfonyl}-4-piperidinyl)-1H-indazole-7-carboxamide.

Compound Preparation

The compounds of the invention are prepared using conventional organic syntheses. Suitable synthetic routes are depicted in the following general reaction schemes:

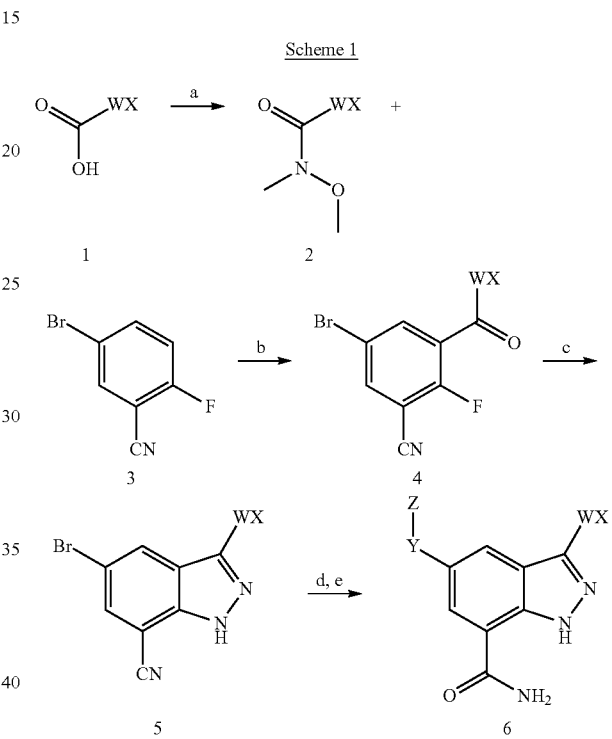

Conditions: a) N,O-dimethylhydroxylamine, HATU, DMF b) LDA, THF, -78° C., c) Hydrazine hydrate, EtOH, reflux d) Pd(dppf)Cl₂, ZYB(OR)₂, Cs₂CO₃, 1,4-dioxane; e) NaOH, EtOH, 80-100° C.

Scheme 1 represents a general scheme for the preparation of compounds according to Formula (I) wherein R1 is —WX except wherein W is a bond and X is aryl, heteroaryl, heterocycloalkyl, $C_4$-$C_7$ cycloalkyl, and $C_5$-$C_7$ cycloalkenyl. A general reaction scheme for preparing compounds according to Formula (I) wherein W is a bond and X is N(Rb)SO₂Re, N(Rb)C(O)Re, N(Rb)C(O)ORd, N(Rb)C(O)NRaRb, or N(Rb)C(O)NRxRy is depicted in Scheme 3 below. In Scheme 1, Y and Z are as defined above unless defined otherwise. The carboxylic acid 1 depicted as starting material is commercially available or made from commercially available starting materials using methods known to those skilled in the art. Reaction conditions are as described above in the scheme; however, the skilled artisan will appreciate that certain modifications in the reaction conditions and/or reagents used are possible.

The carboxylic acid 1, is converted to the Weinreb amide 2 via coupling with N,O-dimethylhydroxylamine in the presence of HATU. Subsequent conversion to intermediate 4 can be accomplished via lithiation of 5-bromo-2-fluorobenzonitrile with LDA and reaction with the Weinreb amide 2. With intermediate 4 in hand, reaction with hydrazine hydrate in refluxing ethanol effects hydrazone formation and cyclization to produce indazole intermediate 5. Installation of the substituent YZ can be accomplished via a transition metal mediated coupling using an appropriate catalyst and coupling partner. As an example of such a transformation, for the case in Scheme 1 condition "d", a Suzuki cross-coupling reaction can be completed using a boronic ester or acid in the presence of Pd(dppf)Cl$_2$, and Cs$_2$CO$_3$ in 1,4-dioxane. Further transformation of the nitrile to the primary carboxamide 6 is accomplished via reaction with sodium hydroxide in ethanol. In the case where WX and/or YZ contains a suitable protecting group, removal of the protecting group under the appropriate conditions and further transformation to other desired products may be accomplished.

nium salt is converted to the arylazosulfide via reaction with sodium benzenethiolate. Cyclization and ring closure to the indazole is then accomplished upon treatment with potassium t-buotxide in DMSO. Installation of the substituent YZ can be accomplished via a transition metal mediated coupling using an appropriate catalyst and coupling partner. As an example of such a transformation, for the case in Scheme 2 condition "d", a Suzuki cross-coupling reaction can be completed using a boronic ester or acid in the presence of Pd(dppf)Cl$_2$, and Cs$_2$CO$_3$ in 1,4-dioxane. Conversion of the methylester to the primary carboxamide 11 can be completed via hydrolysis of the ester with sodium hydroxide followed by coupling of the resultant acid with ammonia in the presence of HATU. Compound 11 may be converted to the C3 halide via treatment with an electrophilic halogenation reagent such as N-chlorosuccinimide.

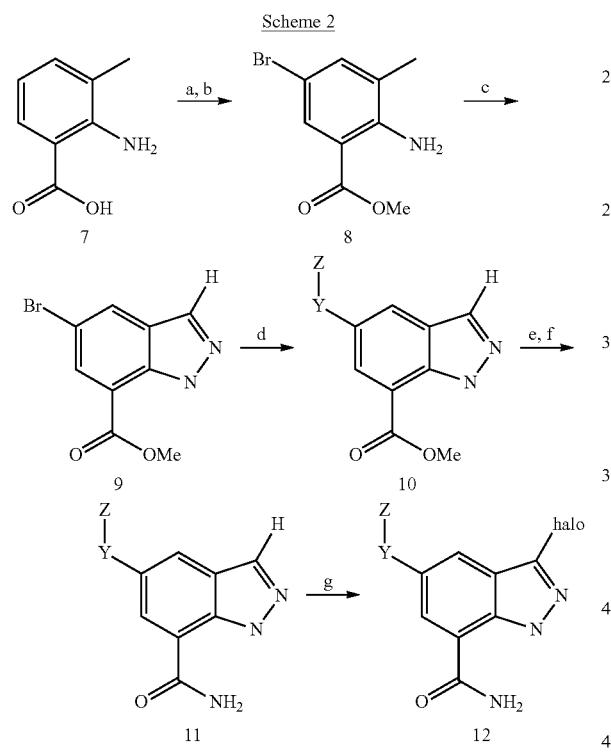

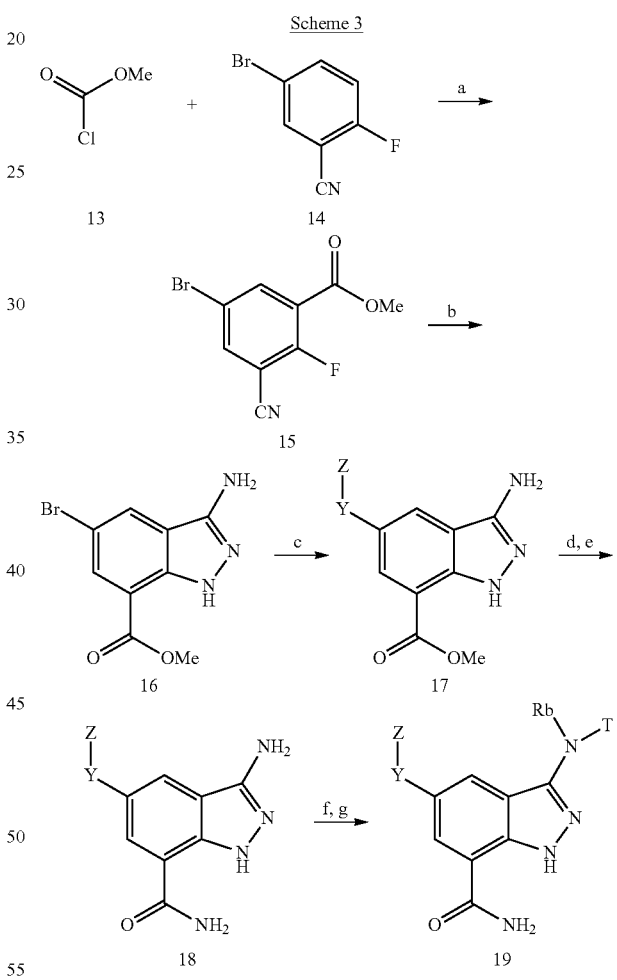

Conditions: a) H$_2$SO$_4$, MeOH b) 1,3-dibromo-5,5-dimethylhydantoin, H$_2$SO$_4$; c) i. i-amylnitrite, PhSNa; ii. t-BuOK, DMSO d) Pd(dppf)Cl$_2$, ZYB(OR)$_2$, Cs$_2$CO$_3$, 1,4-dioxane; e) NaOH, EtOH, 80-100° C.; f) NH$_3$, HATU, DMF; g) N-halosuccinimide, CH$_2$Cl$_2$.

Scheme 2 represents a general scheme for the preparation of compounds according to Formula (I) wherein R1 is H or halo. In Scheme 2, Y and Z are as defined above unless defined otherwise. The 2-methyl-3-aminobenzoic acid (7) depicted as starting material is commercially available. Reaction conditions are as described above in the scheme; however, the skilled artisan will appreciate that certain modifications in the reaction conditions and/or reagents used are possible.

Treatment of 2-methyl-3-aminobenzoic acid (7) with sulfuric acid in methanol produces the desired methyl ester. This is further reacted with 1,3-dibromo-5,5-dimethylhydantoin to produce the desired bromide 8. Formation of the indazole can then be accomplished via diazotization and cyclization. One illustrative method for the formation of the indazole ring is that described by Dell'Erba and co-workers (Tetrahedron 50 (11), 1994, 3529-3536) whereby the intermediate diazo- Conditions: a) LDA, THF, -78° C.; b) Hydrazine hydrate, EtOH, reflux; c) Pd(dppf)Cl$_2$, ZYB(OR)$_2$, Cs$_2$CO$_3$, 1,4-dioxane; d) NaOH, EtOH, 80-100 C.; e) NH3, HATU, DMF; f) RCHO, NaCNBH3, HOAc, MeOH; g) TCl, TEA, CH$_2$Cl$_2$ Scheme 3 represents a general scheme for the preparation of compounds according to Formula (I) wherein R1 is —WX, and W is a bond and X is N(Rb)T, where "T" represents: —SO$_2$Re, —C(O)Re, —C(O)ORd, —C(O)NRaRb, or —C(O)NRxRy. In Scheme 3, Y and Z are as defined above unless defined otherwise. The 5-bromo-2-fluorobenzonitrile depicted as starting material is commercially available. Reaction conditions are as described above in the scheme; however, the skilled artisan will appreciate that certain modifications in the reaction conditions and/or reagents used are possible.

Treatment of 5-bromo-2-fluorobenzonitrile (14) with LDA followed by reaction with methylchloroformate (7) gives rise to ester 15. Aminoindazole formation producing 16 can then be accomplished via reaction with hydrazine hydrate in ethanol. Installation of the substituent YZ can be accomplished via a transition metal mediated coupling using an appropriate catalyst and coupling partner. As an example of such a transformation, for the case in Scheme 3 condition "c", a Suzuki cross-coupling reaction can be completed using a boronic ester or acid in the presence of Pd(dppf)Cl$_2$, and Cs$_2$CO$_3$ in 1,4-dioxane. Conversion of the methylester to the primary carboxamide 18 can be completed via hydrolysis of the ester with sodium hydroxide followed by coupling of the resultant acid with ammonia in the presence of HATU. In the case where Rb is C1-C3 alkyl, the alkyl group may be incorporated via a reductive amination using the appropriate aldehyde. For the case where Rb is H, it will be appreciated by those skilled in the art that step "f" of Scheme 3 can be omitted. Subsequent transformation via reaction with the appropriate precursor to T then produces the desired product 19.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Methods of Use

The compounds of the invention are inhibitors of IKK2. These compounds can be useful in the treatment of disorders wherein the underlying pathology is (at least in part) attributable to inappropriate IKK2 (also known as IKKβ) activity such as rheumatoid arthritis, inflammatory bowel disease, asthma, and COPD (chronic obstructive pulmonary disease). "Inappropriate IKK2 activity" refers to any IKK2 activity that deviates from the normal IKK2 activity expected in a particular patient. Inappropriate IKK2 activity may take the form of, for instance, an abnormal increase in activity, or an aberration in the timing and or control of IKK2 activity. Such inappropriate activity may result then, for example, from overexpression or mutation of the protein kinase leading to inappropriate or uncontrolled activation. Accordingly, in another aspect the invention is directed to methods of treating such disorders.

Such disorders include inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restonosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia.

The methods of treatment of the invention comprise administering a safe and effective amount of a compound according to Formula I or a pharmaceutically-acceptable salt thereof to a patient in need thereof. Individual embodiments of the invention include methods of treating any one of the above-mentioned disorders by administering a safe and effective amount of a compound according to Formula I or a pharmaceutically-acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also provides a compound of the invention for use in medical therapy, and particularly in the treatment of disorders mediated by IKK2 activity. Thus, in a further aspect, the invention is directed to the use of a compound according to Formula I or a pharmaceutically-acceptable salt thereof in the preparation of a medicament for the treatment of a disorder characterized by inappropriate IKK2 activity.

Particular disorders characterized by inappropriate IKK2 activity include inflammatory and tissue repair disorders, particularly rheumatoid arthritis, inflammatory bowel disease, asthma and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia as a result of inhibition of the protein kinase IKK2.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically may contain, for example, from 0.5 mg to 1 g, or from 1 mg to 700 mg, or from 5 mg to 100 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethyl-aspartamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of the invention.

Aerosols may be formed by suspending or dissolving a compound of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3 (6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions may be applied as a topical ointment or cream. When formulated in an ointment, the compound of the invention may be employed with either a paraffinic or a water-miscible ointment base. Alternatively, the compound of the invention may be formulated in a cream with an oil-in-water cream base or a water-in-oil base.

Pharmaceutical compositions adapted for nasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of the invention.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at room temperature.

Compounds were purified by preparative HPLC or by silica chromatography. Preparative HPLC refers to methods where the material was purified by high pressure liquid chromatography. Preparative HPLC was carried out on a C18-reverse-phase column (10 cm×2.1 cm i.d Genesis column with 7 um particle size), eluting with a gradient of acetonitrile (containing 0.1% trifluoroacetic acid) in water (containing 0.1% trifluoroacetic acid) at a flow rate of 5 ml/min. UV detection at 230 nm was used unless otherwise stated. Unless otherwise stated, silica flash column chromatography refers to the purification of material using Redisep™ pre-packed silica flash columns on an ISCO sq16× machine with the stated solvent systems.

Mass spectra were recorded on the following equipment:
(1) Platform LCT with electrospray source operating in positive ion mode. Waters 1525 Ic pump running at 2.0 ml/min, HTS PAL autosampler, 200 ul/min split to the ESI source with inline Waters UV2488 Dual Wavelength UV detector at 254 nm and Sedex ELS detection. Column—Higgins Clipeus C18 5 um 100×3.0 mm, or
(2) Finnigan TSQ700 with electrospray source operating in positive or negative ion mode. HP1050 system running at 2.0 mL/min, 200 uL/min split to the ESI source with inline HP1050 Single Wavelength UV detector at 254 nm. Column—Higgins Clipeus C18, 5 micron, 100×3.0 mm, or

| (3) PE Sciex Single Quadrupole LC/MS API-150: Liquid Chromatograph: | |
|---|---|
| System: | Shimadzu LC system with SCL-10A Controller and dual UV detector |
| Autosampler: | Leap CTC with a Valco six port injector |
| Column: | Aquasil/Aquasil (C18 40 × 1 mm) |
| Inj. Volume (µL): | 2.0 |
| Solvent A: | H2O, 0.02% TFA |
| Solvent B: | MeCN, 0.018% TFA |
| Gradient: | linear |
| Channel A: | UV 214 nm |
| Channel B: | ELS |

| Step | Time (min) | Dura. (min) | Flow (µL/min) | Sol. A | Sol. B |
|---|---|---|---|---|---|
| 0 | 0.00 | 0.00 | 300.00 | 95.00 | 5.00 |
| 1 | 0.00 | 0.01 | 300.00 | 95.00 | 5.00 |
| 2 | 0.01 | 3.20 | 300.00 | 10.00 | 90.00 |

| | | | | | |
|---|---|---|---|---|---|
| 3 | 3.21 | 1.00 | 300.00 | 10.00 | 90.00 |
| 4 | 4.21 | 0.10 | 300.00 | 95.00 | 5.00 |
| 5 | 4.31 | 0.40 | 300.00 | 95.00 | 5.00 |

(3) PE Sciex Single Quadrupole LC/MS API-150:
Liquid Chromatograph:

Mass Spectrometer: PE Sciex Single Quadrupole LC/MS API-150
Polarity: Positive
Acquisition mode: Profile $^1$H NMR spectra were recorded on a Varian Unity Inova 400 or Bruker AC 400 spectrometer, which operates at 400 MHz for $^1$H. CDCl$_3$ is deuteriochloroform, DMSO-6 is hexadeuteriodimethylsulfoxide, and CD$_3$OD is tetradeuterimethanol. Chemical shifts are reported in parts per million (δ) downfield from the internal standard teramethylsilane. Abbreviations for NMR data are as follows: s=singlet, d=doublet, t=triplet, q=quarter, m=multiplet, dd=doublet or doublets, dt=doublet of triplets, app=apparent, br=broad. J indicates the NMR coupling constant measured in Hertz.

Unless otherwise stated, silica flash column chromatography and Combiflash refers to the purification of material using Redisep™ pre-packed silica flash columns on an ISCO sq16× machine with the stated solvent systems.

Intermediates

Intermediate 1

1,1-dimethylethyl 4-{[methyl(methyloxy)amino]carbonyl}-1-piperidine-carboxylate

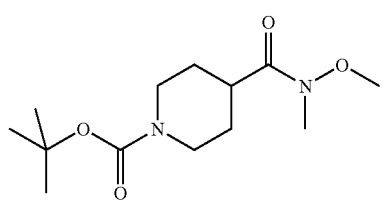 [SMILES: CON(C)C(=O)C1CCN(C(=O)OC(C)(C)C)CC1]

N,O-Dimethylhydroxylamine hydrochloride (4.26 g, 43.7 mmols), di-isopropylethylamine (33.88 g, 45.66 mL, 262.2 mmols) and HATU (19.94 g, 52.4 mmols) were added to a solution of N-Boc-piperidine-4-carboxylic acid (11.03 g, 48.1 mmols) in dry DMF (250 mL). The reaction mixture was stirred at room temperature for 72 hrs. The DMF was removed in vacuo and the residue was partitioned between ethyl acetate (200 mL) and saturated aqueous sodium bicarbonate (200 mL). The organic phase was separated, washed with saturated aqueous sodium bicarbonate (200 mL) and brine (200 mL), and dried over MgSO$_4$. Evaporation of the solvent afforded a dark oil (21.0 g) that was purified by flash chromatography (Silica, gradient elution with pentane/ethyl acetate 9:1 v/v to 3:2 v/v) to give the title compound 12.5 g (95%) as a gum.

LC/MS-M+H 273

Intermediate 2

1,1-dimethylethyl 4-[(5-bromo-3-cyano-2-fluorophenyl)carbonyl]-1-piperidinecarboxylate

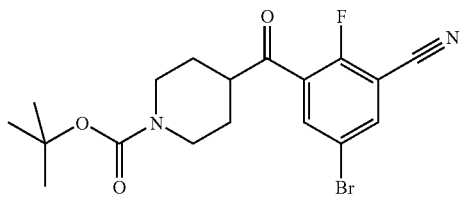 [SMILES: CC(C)(C)OC(=O)N1CCC(C(=O)c2cc(Br)cc(C#N)c2F)CC1]

A solution of 5-bromo-2-fluorobenzonitrile (7.34 g, 36.7 mmols) in dry THF (90 mL) was cooled to −78° C. under a nitrogen atmosphere. A 2M solution of LDA in THF (21.48 mL, 43.0 mmols) was added during 15 mins and the mixture was stirred at −78° C. for 2 h giving a deep blue solution. 1,1-dimethylethyl 4{[methyl(methyloxy)amino]carbonyl}-1-piperidinecarboxylate (12.5 g, 45.9 mmols) in dry THF (45 mL) was added and the reaction mixture was allowed to warm to room temperature and stirred for 16 hrs (overnight). Saturated aqueous ammonium chloride (200 mL) was added followed by ethyl acetate (200 mL). The mixture was treated with charcoal to decolorize, filtered and the organic phase separated. The organic layer was washed with saturated aqueous ammonium chloride and dried over MgSO$_4$. Evaporation of the solvent afforded a green solid (16.8 g). The solid was purified by flash chromatography (Dry loaded onto silica, gradient elution with pentane/ethyl acetate 9:1 v/v to 3:2 v/v) to give the title compound (1.35 g) as a green gum (9%).

LC/MS-M−H 407

Intermediate 3

1,1-dimethylethyl 4-(5-bromo-7-cyano-1H-indazol-3-yl)-1-piperidine-carboxylate

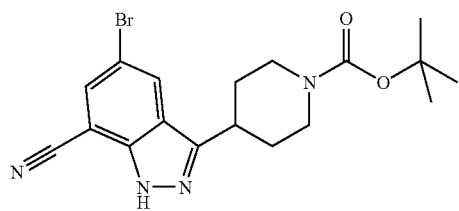 [SMILES: CC(C)(C)OC(=O)N1CCC(c2n[nH]c3c(C#N)cc(Br)cc23)CC1]

A mixture of 1,1-dimethylethyl 4-[(5-bromo-3-cyano-2-fluorophenyl)carbonyl]-1-piperidinecarboxylate (1.35 g, 3.3 mmols) and hydrazine hydrate (0.21 ml, 6.9 mmols) in ethanol (30 mL) was heated at reflux overnight. After cooling, the solvent was evaporated and the residue was purified by flash chromatography eluting with pentane/ethyl acetate 4:1 v/v to give the title compound (0.78 g) as a yellow solid (59%).

LC/MS-M+H 405

Intermediate 4

1,1-dimethylethyl 4-(7-cyano-5-phenyl-1H-indazol-3-yl)-1-piperidine-carboxylate

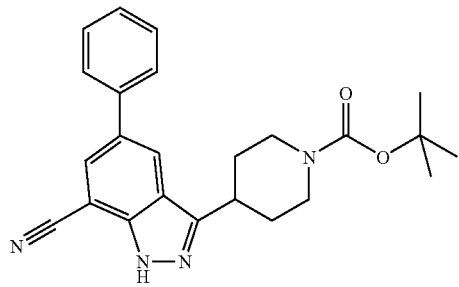 [SMILES: CC(C)(C)OC(=O)N1CCC(c2n[nH]c3c(C#N)cc(-c4ccccc4)cc23)CC1]

A mixture of 1,1-dimethylethyl 4-(5-bromo-7-cyano-1H-indazol-3-yl)-1-piperidine-carboxylate (0.78 g, 1.9 mmols), phenyl boronic acid (0.26 g, 2.1 mmols), aqueous cesium carbonate (4 mL, 2M), and Pd(dppf)Cl$_2$ (0.16 g, 0.19 mmols) in dioxane (12 mL) was split equally between 4, 5 mL microwave reaction vessels. One was heated at 100° C. for 1800 seconds while the other was heated at 100° C. for 2700 seconds. The contents of the vials were combined and partitioned between ethyl acetate and water. The organic phase was washed with water, dried over MgSO$_4$, filtered, and concentrated to give 0.62 g of a yellow solid. 1H NMR indicated a mixture of desired product, phenyl boronic acid, and starting bromide. The mixture, along with Pd(dppf)Cl$_2$ (0.03 g, 0.034 mmols), 2M cesium carbonate solution (0.68 mL, 1.4 mmols) and dioxane (2 mL), was re-subjected to the reaction conditions (microwave irradiation, 100° C., 1800 secs). The resulting mixture was partitioned between ethyl acetate and water. The organic layer was dried over MgSO$_4$, filtered, and concentrated to give a dark gum. This was purified via silica gel chromatography using 20% ethyl acetate/pentane as the mobile phase to give 0.24 g of a yellow solid.

LC/MS-M+H 403

Intermediate 5

1,1-dimethylethyl 4-[7-(aminocarbonyl)-5-bromo-1H-indazol-3-yl]-1-piperidinecarboxylate

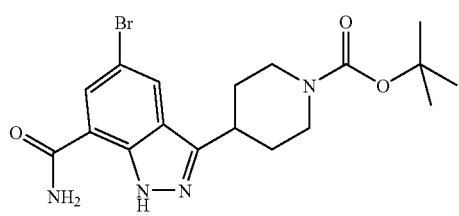 [SMILES: CC(C)(C)OC(=O)N1CCC(c2n[nH]c3c(C(N)=O)cc(Br)cc23)CC1]

To 4-(5-bromo-7-cyano-1H-indazol-3-yl)-1-piperidine-carboxylate (0.30 g, 0.74 mmols) in 2-methyl-2-propanol (30 mL) was added KOH (0.45 g, 7.4 mmol). The reaction mixture was heated at reflux overnight. After cooling, the solvent was evaporated and the residue was redissovled in ethyl acetate (150 mL) and filtered through a pad of silica gel to give the title compound (300 mg) as a yellow solid (99%).

LC/MS (ESI) 423.2 [M+H]$^+$ Rt 2.10 min

Intermediate 6

5-bromo-3-(4-piperidinyl)-1H-indazole-7-carboxamide

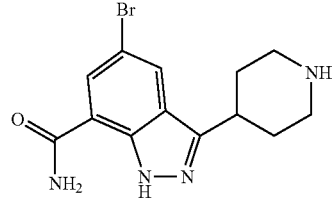 [SMILES: NC(=O)c1cc(Br)cc2c(C3CCNCC3)n[nH]c12]

A solution of 1,1-dimethylethyl 4-[7-(aminocarbonyl)-5-bromo-1H-indazol-3-yl]-1-piperidinecarboxylate (Intermediate 5) (1 g, 2.36 mmols) and concentrated HCl (3 mL) in methanol (75 mL) was heated to 50° C. for 2 hrs. The solution was cooled and the solvent removed in vacuo to give the crude amine hydrochloride salt (0.8 g, 94%), which was used in the next step without further purification.

LC/MS: 323 Rt. 1.28 min.

Intermediate 7

5-bromo-3-{1-[(3-chloropropyl)sulfonyl]-4-piperidinyl}-1H-indazole-7-carboxamide

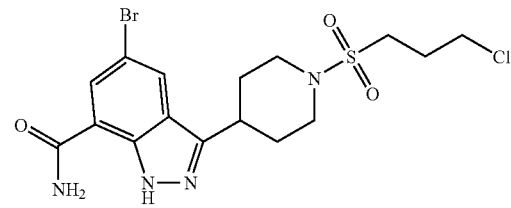 [SMILES: NC(=O)c1cc(Br)cc2c(C3CCN(S(=O)(=O)CCCCl)CC3)n[nH]c12]

This compound was prepared in a fashion analogous to the procedure described in Example 3. Thus, 5-bromo-3-(4-piperidinyl)-1H-indazole-7-carboxamide hydrochloride (100 mg, 0.31 mmol) was reacted with 3-chloro-1-propanesulfonyl chloride (63 uL, 0.46 mmol) in the presence of diisopropylethylamine (0.24 mL, 1.38 mmol) in methylene chloride (5 mL) to give the crude title compound (140 mg, 98%), which was used in the next step without further purification.

LC/MS: 463.2 Rt. 2.02 min.

Intermediate 8

5-bromo-3-(1-{[3-(dimethylamino)propyl]sulfonyl}-4-piperidinyl)-1H-indazole-7-carboxamide

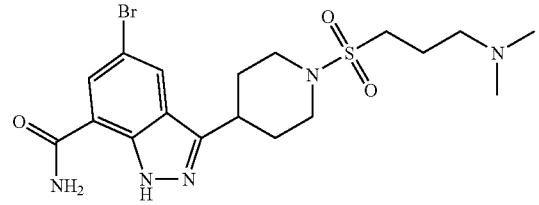 [SMILES: CN(C)CCCS(=O)(=O)N1CCC(c2n[nH]c3c(C(N)=O)cc(Br)cc23)CC1]

To a solution of 5-bromo-3-{1-[(3-chloropropyl)sulfonyl]-4-piperidinyl}-1H-indazole-7-carboxamide (Intermediate 7) (200 mg, 0.432 mmol) in DMF (5 mL) was added K$_2$CO$_3$ (250 mg), sodium iodide (10 mg), and 2M dimethyl amine in DMF (1 mL) The reaction mixture was heated to 60° C. overnight. The solution was filtered. The filtrate was purified by using a Gilson semi-preparative HPLC system with a YMC ODS-A (C-18) column 50 mm by 20 mm ID, eluting with 40% B to 80% B in 3.2 min, hold for 1 min where A=H₂O (0.1% trifluoroacetic acid) and B=CH₃CN (0.1% trifluoroacetic acid) pumped at 25 mL/min to afford the title compound (100 mg, 49%)

LC/MS: 473.0 Rt: 1.54 min.

Intermediate 9

5-bromo-3-(4-piperidinyl)-1H-indazole-7-carbonitrile

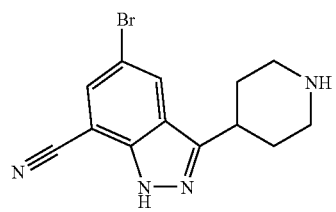 [SMILES: N#Cc1cc(Br)cc2c(C3CCNCC3)n[nH]c12]

A solution of 1,1-dimethylethyl 4-(5-bromo-7-cyano-1H-indazol-3-yl)-1-piperidine-carboxylate (Intermediate 3) (0.200 g, 0.493 mmols) and trifluoroacetic acid (0.25 mL) in dichloromethane (5 mL) was stirred at room temperature for 2 hrs. The solution was cooled and the solvent removed in vacuo to give the crude amine (222 mg) trifluoroacetate salt, which was used in the next step without further purification.

LC/MS: 305.0 Rt: 1.33 min.

Intermediate 10

5-bromo-3-[1-(ethylsulfonyl)-4-piperidinyl]-1H-indazole-7-carbonitrile

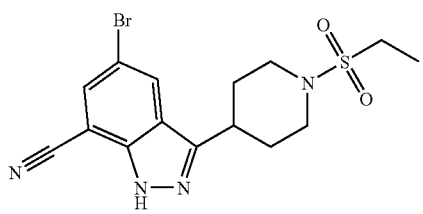 [SMILES: CCS(=O)(=O)N1CCC(c2n[nH]c3c(C#N)cc(Br)cc23)CC1]

The crude 5-bromo-3-(4-piperidinyl)-1H-indazole-7-carbonitrile (Intermediate 9) (0.222 g, 0.493 mmol) was suspended in dichloromethane (5 mL) and treated with diisopropylethyl amine (0.257 mL, 1.48 mmols), and ethane sulfonyl chloride (0.070 mL, 0.74 mmols) at ambient temperature. After 2 hrs, the mixture was concentrated to dryness in vacuo at ambient temperature, treated with water (25 mL), and extracted with dichloromethane (100 mL). The organic phase was washed with water, dried over MgSO₄, filtered, and concentrated to give a light brown solid. This was purified by combiflash (column 10 g, eluting with 100% dichloromethane, 5% ethyl acetate/dichloromethane, 30% ethyl acetate/dichloromethane) to give the title compound (0.083 g, 24%).

LC/MS: 397.0 Rt: 2.16 min.

Intermediate 11

3-[1-(ethylsulfonyl)-4-piperidinyl]-5-(4-fluorophenyl)-1H-indazole-7-carbonitrile

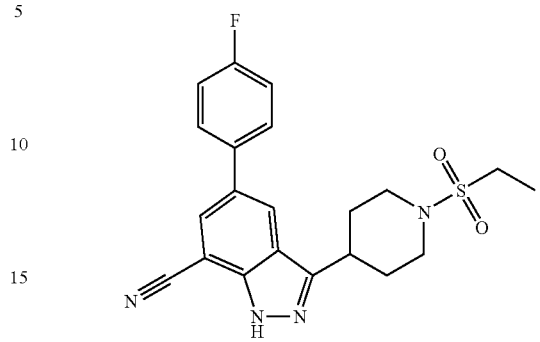

Following the general procedure of Example 65, a mixture of 5-bromo-3-[1-(ethylsulfonyl)-4-piperidinyl]-1H-indazole-7-carbonitrile (Intermediate 10) (50 mg, 0.102 mmols), 4-fluorophenyl boronic acid (42 mg, 0.306 mmols), potassium carbonate (84 mg, 0.612 mmol), and Pd(PPh₃)₄ (10 mg) in dioxane/water (6/1, 3.5 mL) were reacted to give the crude title compound.

LC/MS: 414.4 Rt. 1.89 min.

Intermediate 12

3-[1-(ethylsulfonyl)-4-piperidinyl]-5-(2-fluorophenyl)-1H-indazole-7-carbonitrile

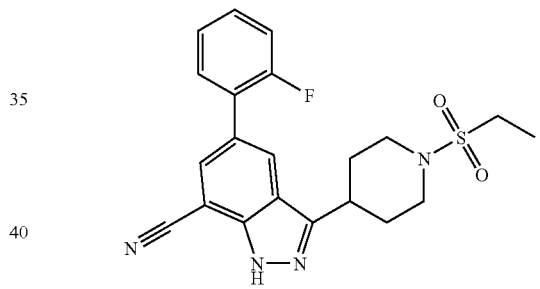

Following the general procedure of Example 65, a mixture of 5-bromo-3-[1-(ethylsulfonyl)-4-piperidinyl]-1H-indazole-7-carbonitrile (Intermediate 10) (50 mg, 0.102 mmols), 2-fluorophenyl boronic acid (42 mg, 0.306 mmols), potassium hydroxide (84 mg, 0.612 mmol), and Pd(PPh₃)₄ (10 mg) in dioxane/water (6/1, 3.5 mL) were reacted to give the crude title compound.

LC/MS: 414.4 Rt. 1.93 min.

Intermediate 13

5-bromo-3-[1-(ethylsulfonyl)-4-piperidinyl]-1H-indazole-7-carboxamide

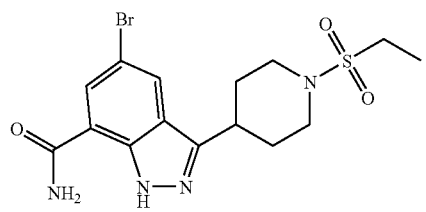 [SMILES: CCS(=O)(=O)N1CCC(c2n[nH]c3c(C(N)=O)cc(Br)cc23)CC1]

The crude 5-bromo-3-(4-piperidinyl)-1H-indazole-7-carboxamide (Intermediate 6) (1.23 mmol) was suspended in dichloromethane (20 mL) and treated with triethyl amine (0.856 mL, 6.15 mmols), and ethane sulfonyl chloride (0.175 mL, 1.85 mmols) at 0° C. After 2 hrs, the mixture was concentrated to dryness in vacuo at ambient temperature, treated with water (25 mL), and extracted with dichloromethane (100 mL). The organic phase was washed with water, dried over MgSO$_4$, filtered, and concentrated to give a light brown solid. This was purified by combiflash (column 10 g, eluting with 100% dichloromethane, 5% ethyl acetate/dichloromethane, 30% ethyl acetate/dichloromethane) to give the title compound (0.161 g, 32%).

LC/MS: 417.0 Rt: 1.71 min.

Intermediate 14

1,1-dimethylethyl 4-[7-(aminocarbonyl)-5-(3-fluorophenyl)-1H-indazol-3-yl]-1-piperidinecarboxylate

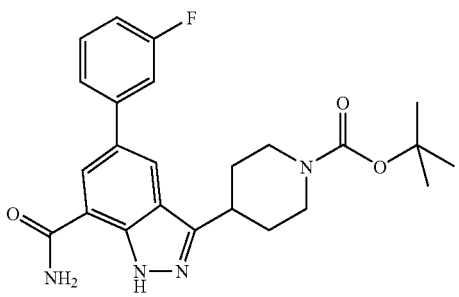 [SMILES: CC(C)(C)OC(=O)N1CCC(c2n[nH]c3c(C(N)=O)cc(-c4cccc(F)c4)cc23)CC1]

Following the general procedure of Example 65, a mixture of 1,1-dimethylethyl 4-[7-(aminocarbonyl)-5-bromo-1H-indazol-3-yl]-1-piperidine carboxylate (Intermediate 5) (400 mg, 0.545 mmols), 3-fluorophenyl boronic acid (397 mg, 2.84 mmols), potassium carbonate (782 mg, 5.67 mmol), and Pd(PPh$_3$)$_4$ (218 mg, 0.189 mmol) in dioxane/water (7 mL/1 mL) were reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (280 mg, 68%)

LC/MS: 439.4 Rt. 2.46 min.

Intermediate 15

5-(3-fluorophenyl)-3-(4-piperidinyl)-1H-indazole-7-carboxamide

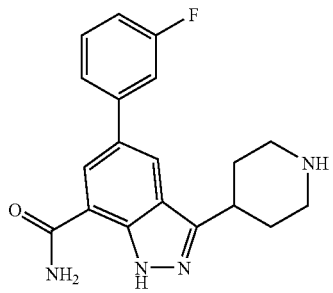 [SMILES: NC(=O)c1cc(-c2cccc(F)c2)cc2c(C3CCNCC3)n[nH]c12]

A solution of 1,1-dimethylethyl 4-[7-(aminocarbonyl)-5-(3-fluorophenyl)-1H-indazol-3-yl]-1-piperidinecarboxylate (Intermediate 14) (1.057 g, 2.41 mmols) and 4M HCl in dioxane (30 mL) was bubbled HCl (gas) for 3 mins and stirred at room temperature overnight. The solvent removed in vacuo to give the crude amine hydrochloride salt (1.10 g, 94%), which was used in the next step without further purification.

LC/MS: 339.4 Rt. 1.59 min.

Intermediate 16

1,1-dimethylethyl 4-[7-(aminocarbonyl)-5-(2-thienyl)-1H-indazol-3-yl]-1-piperidinecarboxylate

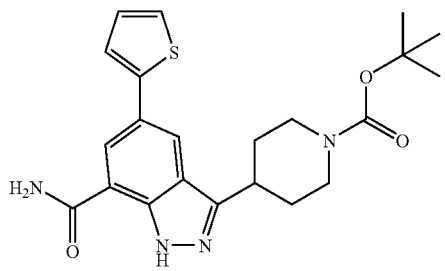 [SMILES: CC(C)(C)OC(=O)N1CCC(c2n[nH]c3c(C(N)=O)cc(-c4cccs4)cc23)CC1]

Following the general procedure of Example 65, a mixture of 1,1-dimethylethyl 4-[7-(aminocarbonyl)-5-bromo-1H-indazol-3-yl]-1-piperidinecarboxylate (Intermediate 5) (100 mg, 0.24 mmols), 2-thienylboronic acid (92 mg, 0.72 mmols), potassium carbonate (197 mg), and Pd(PPh$_3$)$_4$ (28 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (56 mg, 55%)

LC/MS: 427.4 Rt. 2.24 min.

Intermediate 17

3-(4-piperidinyl)-5-(2-thienyl)-1H-indazole-7-carboxamide

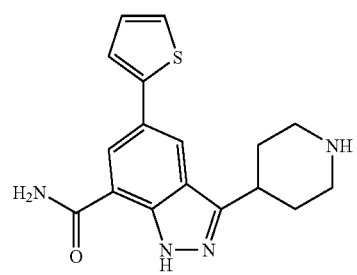 [SMILES: NC(=O)c1cc(-c2cccs2)cc2c(C3CCNCC3)n[nH]c12]

A solution of 1,1-dimethylethyl 4-[7-(aminocarbonyl)-5-(2-thienyl)-1H-indazol-3-yl]-1-piperidinecarboxylate (Intermediate 16) (56 mg, 0.131 mmols) and 4M HCl in dioxane (1.1 mL) in methanol (2 mL) was stirred at room temperature for 2 hrs. The solution was cooled and the solvent removed in vacuo to give the crude amine hydrochloride salt, which was used in the next step without further purification.

LC/MS: 327.0 Rt. 1.32 min.

Intermediate 18

1,1-dimethylethyl 4-[7-(aminocarbonyl)-5-(3-thienyl)-1H-indazol-3-yl]-1-piperidinecarboxylate

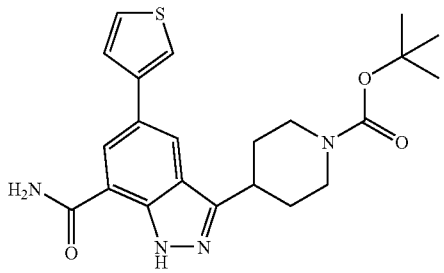 [SMILES: CC(C)(C)OC(=O)N1CCC(c2n[nH]c3c(C(N)=O)cc(-c4ccsc4)cc23)CC1]

Following the general procedure of Example 65, a mixture of 1,1-dimethylethyl 4-[7-(aminocarbonyl)-5-bromo-1H-indazol-3-yl]-1-piperidinecarboxylate (Intermediate 5) (100 mg, 0.24 mmols), 3-thienylboronic acid (92 mg, 0.72 mmols), potassium carbonate (197 mg), and Pd(PPh$_3$)$_4$ (28 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (57 mg, 55%)

LC/MS: 427.0 Rt. 2.19 min.

Intermediate 19

3-(4-piperidinyl)-5-(3-thienyl)-1H-indazole-7-carboxamide

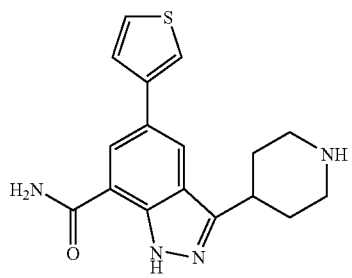 [SMILES: NC(=O)c1cc(-c2ccsc2)cc2c(C3CCNCC3)n[nH]c12]

A solution of 1,1-dimethylethyl 4-[7-(aminocarbonyl)-5-(3-thienyl)-1H-indazol-3-yl]-1-piperidinecarboxylate (Intermediate 18) (56 mg, 0.131 mmols) and 4M HCl in dioxane (1.1 mL) in methanol (2 mL) was stirred at room temperature for 2 hrs. The solution was cooled and the solvent removed in vacuo to give the crude amine hydrochloride salt, which was used in the next step without further purification.

LC/MS: 327.0 Rt. 1.56 min.

Intermediate 20

1,1-dimethylethyl 4-[7-(aminocarbonyl)-5-(3-pyridinyl)-1H-indazol-3-yl]-1-piperidinecarboxylate

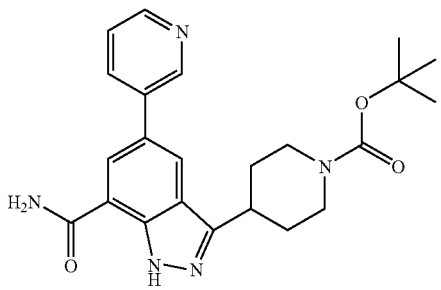 [SMILES: CC(C)(C)OC(=O)N1CCC(c2n[nH]c3c(C(N)=O)cc(-c4cccnc4)cc23)CC1]

Following the general procedure of Example 65, a mixture of 1,1-dimethylethyl 4-[7-(aminocarbonyl)-5-bromo-1H-indazol-3-yl]-1-piperidinecarboxylate (Intermediate 5) (100 mg, 0.24 mmols), 3-pyridinylboronic acid (88.5 mg, 0.72 mmols), potassium carbonate (197 mg), and Pd(PPh$_3$)$_4$ (28 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (33 mg, 38%)

LC/MS: 366.4 Rt. 1.52 min.

Intermediate 21

3-(4-piperidinyl)-5-(3-pyridinyl)-1H-indazole-7-carboxamide

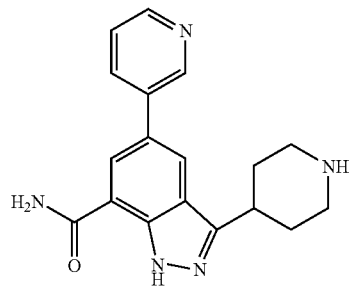

A solution of 1,1-dimethylethyl 4-[7-(aminocarbonyl)-5-(3-pyridinyl)-1H-indazol-3-yl]-1-piperidinecarboxylate (Intermediate 20) (33 mg, 0.09 mmols) and 4M HCl in dioxane (0.8 mL) in methanol (2 mL) was stirred at room temperature for 2 hrs. The solution was cooled and the solvent removed in vacuo to give the crude amine hydrochloride salt, which was used in the next step without further purification.

LC/MS: 322.2 Rt. 0.81 min.

Intermediate 22

3-{1-[(3-chloropropyl)sulfonyl]-4-piperidinyl}-5-phenyl-1H-indazole-7-carboxamide

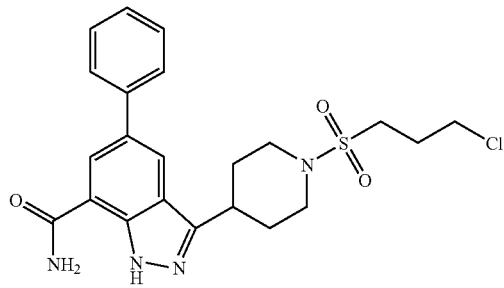 [SMILES: NC(=O)c1cc(-c2ccccc2)cc2c(C3CCN(S(=O)(=O)CCCCl)CC3)n[nH]c12]

This compound was prepared in a fashion analogous to the procedure described in Example 3. Thus, 5-phenyl-3-(4-piperidinyl)-1H-indazole-7-carboxamide hydrochloride (Example 2) (140 mg, 0.437 mmol) was reacted with 3-chloropropane sulfonyl chloride (58 uL, 0.480 mmol) in the presence of diisopropylethyl amine (305 uL, 1.75 mmol) and DMAP (53 mg, 0.437 mmol) in dichloromethane (5 mL) to give the title compound (134 mg, 77%)

LC/MS: 461.2 Rt. 2.12 min.

Intermediate 23

3-[1-(ethylsulfonyl)-4-piperidinyl]-5-[3-(hydroxymethyl)phenyl]-1H-indazole-7-carboxamide

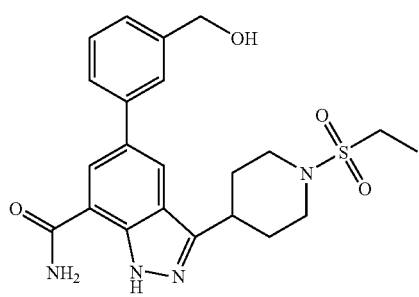 [SMILES: CCS(=O)(=O)N1CCC(c2n[nH]c3c(C(N)=O)cc(-c4cccc(CO)c4)cc23)CC1]

Following the general procedure of Example 65, a mixture of 5-bromo-3-[1-(ethylsulfonyl)-4-piperidinyl]-1H-indazole-7-carboxamide (Intermediate 13) (180 mg, 0.4337 mmols), [3-(hydroxymethyl)phenyl]boronic acid (264 mg, 1.74 mmols), cesium carbonate (282 mg, 0.868 mmol), and Pd(PPh$_3$)$_4$ (22 mg, 0.021 mmol) in dioxane/water (2 mL/0.7 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (130 mg, 68%)

LC/MS: 443.4 Rt. 1.65 min.

Intermediate 24

3-[1-(ethylsulfonyl)-4-piperidinyl]-5-(3-formylphenyl)-1H-indazole-7-carboxamide

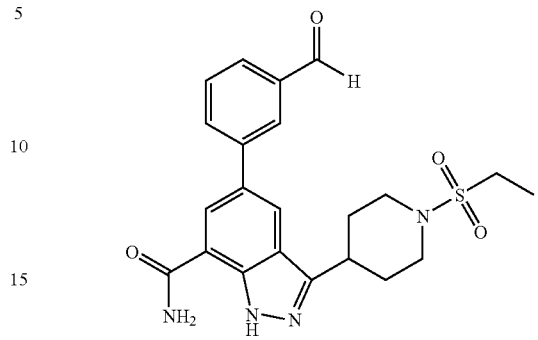

To a solution of 3-[1-(ethylsulfonyl)-4-piperidinyl]-5-[3-(hydroxymethyl)phenyl]-1H-indazole-7-carboxamide (Intermediate 23) (130 mg, 0.294 mmol) in THF (50 mL) was added MnO$_2$ (900 mg, 8.8 mmol). The reaction mixture was stirred at room temperature overnight and filtered. The filtrate was concentrated at reduced pressure to give the crude title compound, which was used in the next step without further purification.

LC/MS: 441.4 Rt. 1.81 min.

Intermediate 25

5-bromo-3-(1-{[3-(methyloxy)propyl]sulfonyl}-4-piperidinyl)-1H-indazole-7-carboxamide

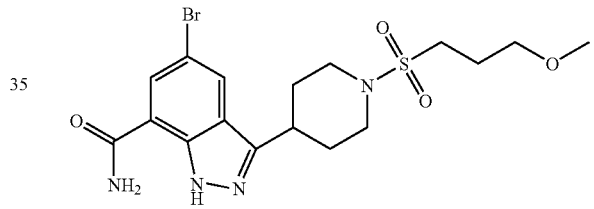

To a solution of 5-bromo-3-{1-[(3-chloropropyl)sulfonyl]-4-piperidinyl}-1H-indazole-7-carboxamide (Intermediate 7) in MeOH (1.5 mL) were added 3.8 M sodium methoxide in MeOH (1 mL) and sodium iodide (5.0 mg). The reaction mixture was stirred at 80° C. overnight and concentrated under reduced pressure. The residue was dissolved in ethyl acetate (15 mL) and washed with water (5 mL). The organic phase was collected, dried over MgSO$_4$, filtered and concentrated to give the crude title compound (30 mg), which was used in the next step without further purification.

LC/MS: 459.2 Rt. 1.80 min.

Intermediate 26

5-(hydroxymethyl)-3-(1-{[3-(methyloxy)propyl]sulfonyl}-4-piperidinyl)-1H-indazole-7-carboxamide

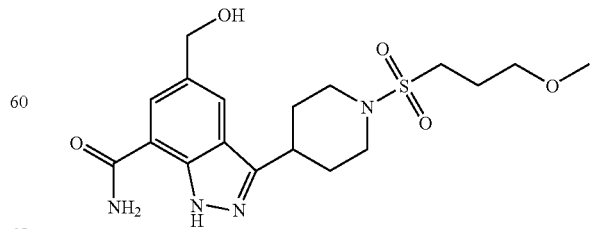

Following the general procedure of Example 65, a mixture of 5-bromo-3-(1-{[3-(methyloxy)propyl]sulfonyl}-4-piperidinyl)-1H-indazole-7-carboxamide (Intermediate 25) (30 mg, 0.065 mmol), [3-(hydroxymethyl)phenyl]boronic acid (40 mg, 0.26 mmols), cesium carbonate (42.5 mg, 0.13 mmol), and Pd(PPh$_3$)$_4$ (22 mg) in dioxane/water (2 mL/0.7 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (18.0 mg, 14%)

LC/MS: 487.4 Rt. 1.69 min.

Intermediate 27

5-bromo-3-(1-{[3-(1-pyrrolidinyl)propyl]sulfonyl}-4-piperidinyl)-1H-indazole-7-carboxamide

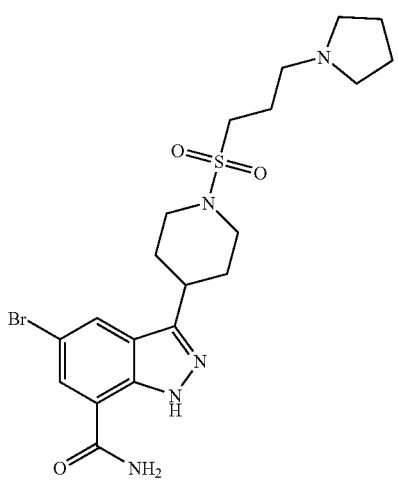 [SMILES: NC(=O)c1cc(Br)cc2c(C3CCN(S(=O)(=O)CCCN4CCCC4)CC3)n[nH]c12]

To a solution of 5-bromo-3-{1-[(3-chloropropyl)sulfonyl]-4-piperidinyl}-1H-indazole-7-carboxamide (Intermediate 7) (200 mg, 0.432 mmol) in DMF (5 mL) was added K$_2$CO$_3$ (120 mg), sodium iodide (2 mg), and pyrrolidine (0.15 mL). The reaction mixture was heated to 60° C. for 2 hrs. The solution was filtered. The filtrate was purified by using a Gilson semi-preparative HPLC system with a YMC ODS-A (C-18) column 50 mm by 20 mm ID, eluting with 40% B to 80% B in 3.2 min, hold for 1 min where A=H$_2$O (0.1% trifluoroacetic acid) and B=CH$_3$CN (0.1% trifluoroacetic acid) pumped at 25 mL/min to afford the title compound (40 mg, 46%)

LC/MS: 499.0 Rt: 1.55 min.

Example 1

1,1-dimethylethyl 4-[7-(aminocarbonyl)-5-phenyl-1H-indazol-3-yl]-1-piperidinecarboxylate

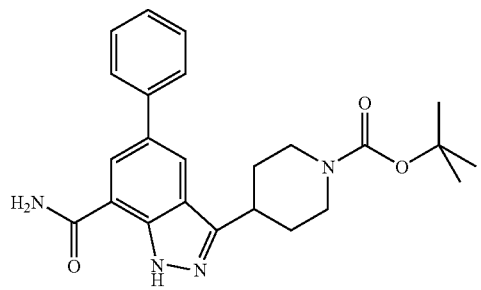 [SMILES: CC(C)(C)OC(=O)N1CCC(c2n[nH]c3c(C(N)=O)cc(-c4ccccc4)cc23)CC1]

A mixture of 1,1-dimethylethyl 4-(7-cyano-5-phenyl-1H-indazol-3-yl)-1-piperidine-carboxylate (Intermediate 4) (1.1 g, 2.7 mmols), and potassium hydroxide (1.53 g, 27.3 mmols) in n-butanol (100 mL) was heated at 85° C. for 2-3 days then at reflux overnight. The solution was cooled and the solvent removed in vacuo. The resulting residue was purified via silica gel chromatography eluting with 50% ethyl acetate/pentane, 100% ethyl acetate, and 30% methanol/ethyl acetate to give 0.68 g of a yellow solid. LC/MS M+H 421

Example 2

5-phenyl-3-(4-piperidinyl)-1H-indazole-7-carboxamide hydrochloride

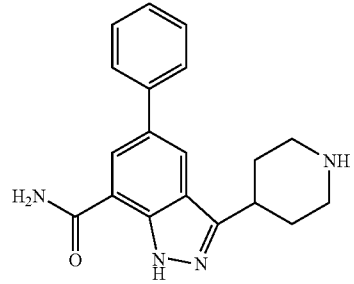 [SMILES: NC(=O)c1cc(-c2ccccc2)cc2c(C3CCNCC3)n[nH]c12]

A solution of 1,1-dimethylethyl 4-[7-(aminocarbonyl)-5-phenyl-1H-indazol-3-yl]-1-piperidinecarboxylate (Example 1) (0.200 g, 0.48 mmols) and concentrated HCl (1 mL) in methanol (8 mL) was heated to 40° C. until no starting material remained (TLC). The solution was cooled and the solvent removed in vacuo to give the crude amine hydrochloride salt, which was used in the next step without further purification.

LC/MS-M+H 321

Example 3

3-[1-(ethylsulfonyl)-4-piperidinyl]-5-phenyl-1H-indazole-7-carboxamide

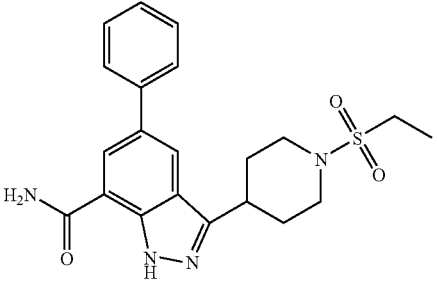 [SMILES: CCS(=O)(=O)N1CCC(c2n[nH]c3c(C(N)=O)cc(-c4ccccc4)cc23)CC1]

The crude 5-phenyl-3-(4-piperidinyl)-1H-indazole-7-carboxamide hydrochloride (Example 2) was suspended in DMF (8 mL) and treated with triethylamine (0.3 mL, 2.2 mmols), DMAP (0.0056 g, 0.065 mmol), and ethane sulfonyl chloride (0.044 mL, 0.47 mmols) at ambient temperature. After 12 hrs, the mixture was concentrated to dryness in vacuo at ambient temperature, treated with water (10 mL), and extracted with ethyl acetate (3×25 mL). The organic phase was washed with water, dried over MgSO$_4$, filtered, and concentrated to give a light brown solid. This was purified via preparative HPL, eluting with 10% B to 80% B, where A=H$_2$O (0.1% trifluoroacetic acid) and B=CH$_3$CN (0.1% trifluoroacetic acid) to give 0.080 g of a white solid.

LC/MS-M+H 413

Example 4

5-phenyl-3-[1-(phenylcarbonyl)-4-piperidinyl]-1H-indazole-7-carboxamide

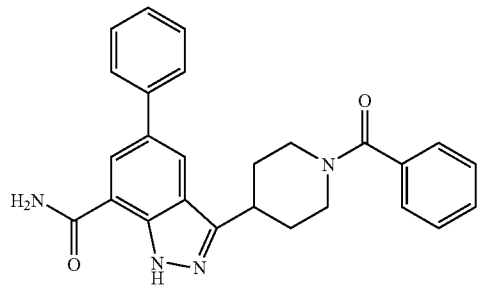 [SMILES: NC(=O)c1cc(-c2ccccc2)cc2c(C3CCN(C(=O)c4ccccc4)CC3)n[nH]c12]

A mixture of 5-phenyl-3-(4-piperidinyl)-1H-indazole-7-carboxamide hydrochloride (0.051 g, 0.17 mmols), triethylamine (0.1 mL, 0.71 mmols), DMAP (0.0021 g, 0.017 mmols), and benzoylchloride (0.020 mL, 0.17 mmols) in DMF (3 mL) was kept at ambient temperature overnight. The mixture was concentrated in vacuo and the resulting residue purified via preparative HPLC, eluting with 10% B to 80% B, where A=H$_2$O (0.1% trifluoroacetic acid) and B=CH$_3$CN (0.1% trifluoroacetic acid) to give 0.036 g of a white solid. LC/MS-M+H 425

Example 5

3-{1-[(1-methyl-1H-imidazol-4-yl)sulfonyl]-4-piperidinyl}-5-phenyl-1H-indazole-7-carboxamide

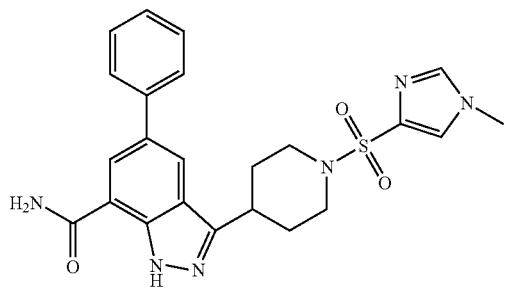 [SMILES: Cn1cnc(S(=O)(=O)N2CCC(c3n[nH]c4c(C(N)=O)cc(-c5ccccc5)cc34)CC2)c1]

This compound was prepared in a fashion analogous to the procedure described in Example 3. Thus, 5-phenyl-3-(4-piperidinyl)-1H-indazole-7-carboxamide hydrochloride (0.057 g, 0.17 mmol) was reacted with 1-methylimidazole-4-sulfonyl chloride (0.031 g, 0.17 mmol) in the presence of triethylamine (0.1 mL, 0.71 mmol) and DMAP (0.0021 g, 0.017 mmol) in DMF (3 mL) to give 0.048 g of white solid.
LC/MS-M+H 465

Example 6

3-{1-[(4-fluorophenyl)sulfonyl]-4-piperidinyl}-5-phenyl-1H-indazole-7-carboxamide

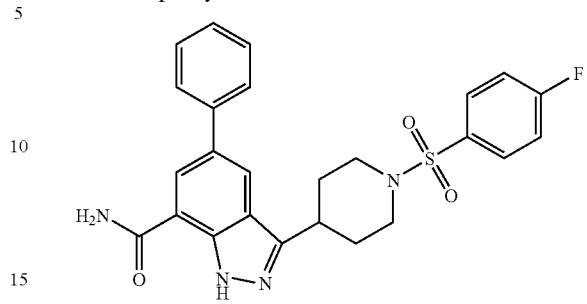

This compound was prepared in a fashion analogous to the procedure described in Example 3. Thus, 5-phenyl-3-(4-piperidinyl)-1H-indazole-7-carboxamide hydrochloride (0.057 g, 0.17 mmol) was reacted with 4-fluorophenyl sulfonyl chloride (0.033 g, 0.17 mmol) in the presence of triethylamine (0.1 mL, 0.71 mmol) and DMAP (0.0021 g, 0.017 mmol) in DMF (3 mL) to give 0.048 g of white solid.
LC/MS-M+H 475

Example 7

3-[1-(methylsulfonyl)-4-piperidinyl]-5-phenyl-1H-indazole-7-carboxamide

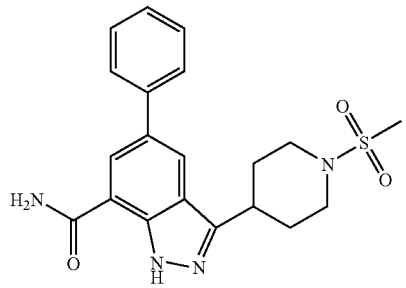 [SMILES: CS(=O)(=O)N1CCC(c2n[nH]c3c(C(N)=O)cc(-c4ccccc4)cc23)CC1]

This compound was prepared in a fashion analogous to the procedure described in Example 3. Thus, 5-phenyl-3-(4-piperidinyl)-1H-indazole-7-carboxamide hydrochloride (0.057 g, 0.17 mmol) was reacted with methanesulfonyl chloride (0.013 mL, 0.17 mmol) in the presence of triethylamine (0.1 mL, 0.71 mmol) and DMAP (0.0021 g, 0.017 mmol) in DMF (3 mL) to give 0.009 g of white solid.
LC/MS-M+H 399

Example 8

3-(1-acetyl-4-piperidinyl)-5-phenyl-1H-indazole-7-carboxamide

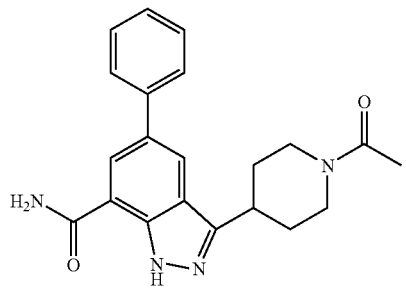 [SMILES: CC(=O)N1CCC(c2n[nH]c3c(C(N)=O)cc(-c4ccccc4)cc23)CC1]

This compound was prepared in a fashion analogous to the procedure described in Example 4. Thus, 5-phenyl-3-(4-piperidinyl)-1H-indazole-7-carboxamide hydrochloride (0.057 g, 0.17 mmol) was reacted with acetyl chloride (0.012 mL, 0.17 mmol) in the presence of triethylamine (0.1 mL, 0.71 mmol) and DMAP (0.0021 g, 0.017 mmol) in DMF (3 mL) to give 0.030 g of a white solid.

LC/MS-M+H 363

Example 9

5-phenyl-3-[1-(phenylsulfonyl)-4-piperidinyl]-1H-indazole-7-carboxamide

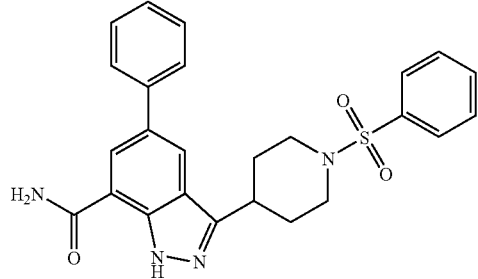 [SMILES: NC(=O)c1cc(-c2ccccc2)cc2c(C3CCN(S(=O)(=O)c4ccccc4)CC3)n[nH]c12]

This compound was prepared in a fashion analogous to the procedure described in Example 3. Thus, 5-phenyl-3-(4-piperidinyl)-1H-indazole-7-carboxamide hydrochloride (0.057 g, 0.17 mmol) was reacted with phenylsulfonyl chloride (0.022 mL, 0.17 mmol) in the presence of triethylamine (0.1 mL, 0.71 mmol) and DMAP (0.0021 g, 0.017 mmol) in DMF (3 mL) to give 0.007 g of pale yellow solid.

LC/MS-M+H 461

Example 10

3-{1-[(1-methylethyl)sulfonyl]-4-piperidinyl}-5-phenyl-1H-indazole-7-carboxamide

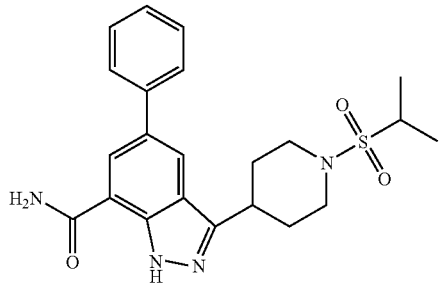 [SMILES: CC(C)S(=O)(=O)N1CCC(c2n[nH]c3c(C(N)=O)cc(-c4ccccc4)cc23)CC1]

This compound was prepared in a fashion analogous to the procedure described in Example 3. Thus, 5-phenyl-3-(4-piperidinyl)-1H-indazole-7-carboxamide hydrochloride (0.057 g, 0.17 mmol) was reacted with isopropylsulfonyl chloride (0.02 mL, 0.17 mmol) in the presence of triethylamine (0.1 mL, 0.71 mmol) and DMAP (0.0021 g, 0.017 mmol) in DMF (3 mL) to give 0.015 g of a white solid.

LC/MS-M+H 427

Example 11

3-{1-[(1,2-dimethyl-1H-imidazol-4-yl)sulfonyl]-4-piperidinyl}-5-phenyl-1H-indazole-7-carboxamide

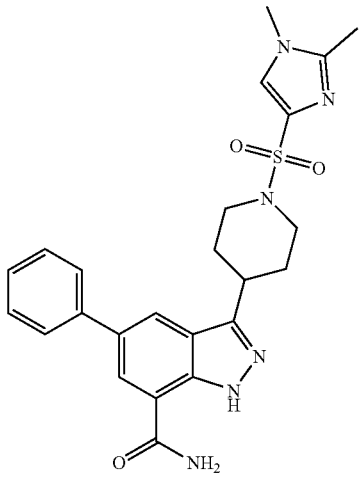 [SMILES: Cc1nc(S(=O)(=O)N2CCC(c3n[nH]c4c(C(N)=O)cc(-c5ccccc5)cc34)CC2)cn1C]

To a solution of 5-phenyl-3-(4-piperidinyl)-1H-indazole-7-carboxamide hydrochloride (Example 2) (50 mg, 0.14 mmol) in DMF (3 mL) was added diisopropylethylamine (100 uL, 0.56 mmol), DMAP (20 mg, 0.014 mmol) and 1,2-dimethyl-1H-imidazole-4-sulfonyl chloride (33 mg, 0.168 mmol). The reaction mixture was stirred at room temperature overnight. The solution was filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to afford the title compound (25 mg, 37%)

LC/MS (ESI) 479.2 [M+H]$^+$ Rt 2.28 min

Example 12

3-{1-[(2-aminoethyl)sulfonyl]4-piperidinyl}-5-phenyl-1H-indazole-7-carboxamide

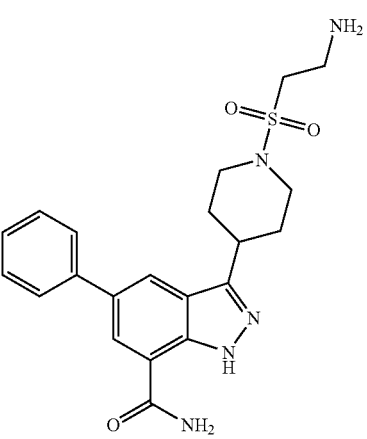 [SMILES: NCCS(=O)(=O)N1CCC(c2n[nH]c3c(C(N)=O)cc(-c4ccccc4)cc23)CC1]

To a solution of 5-phenyl-3-(4-piperidinyl)-1H-indazole-7-carboxamide hydrochloride (Example 2) (50 mg, 0.14 mmol)

in DMF (3 mL) was added diisopropylethylamine (100 uL, 0.56 mmol), DMAP (25 mg, 0.014 mmol) and 2-(2,5-dioxo-1-pyrrolidinyl)ethanesulfonyl chloride (53 mg, 0.168 mmol). After the reaction mixture was stirred at room temperature overnight, hydrazine (4 eq) was added. The reaction mixture was stirred for 4 hrs. The solution was filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to afford the title compound (10 mg, 17%)

LC/MS: 428.0 Rt: 1.54 min.

Example 13

3-(1-{[4-(acetylamino)phenyl]sulfonyl}-4-piperidinyl)-5-phenyl-1H-indazole-7-carboxamide

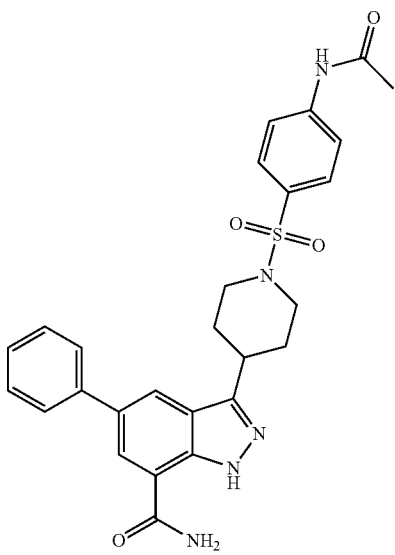 [SMILES: CC(=O)Nc1ccc(S(=O)(=O)N2CCC(c3n[nH]c4c(C(N)=O)cc(-c5ccccc5)cc34)CC2)cc1]

Following the general procedure of Example 11, 5-phenyl-3-(4-piperidinyl)-1H-indazole-7-carboxamide hydrochloride (Example 2) (50 mg, 0.14 mmol), diisopropylethylamine (100 uL, 0.56 mmol), DMAP (25 mg, 0.014 mmol) and 4-(acetylamino)benzenesulfonyl chloride (44 mg, 0.168 mmol) were reacted to give the title compound (20 mg, 28%).

LC/MS: 518.2 Rt: 2.25 min.

Example 14

3-{1-[(4-cyanophenyl)sulfonyl]-4-piperidinyl}-5-phenyl-1H-indazole-7-carboxamide

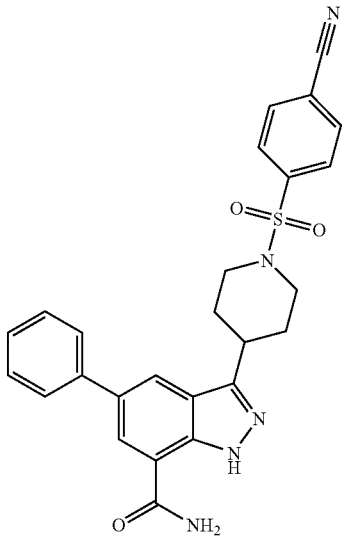 [SMILES: N#Cc1ccc(S(=O)(=O)N2CCC(c3n[nH]c4c(C(N)=O)cc(-c5ccccc5)cc34)CC2)cc1]

Following the general procedure of Example 11, 5-phenyl-3-(4-piperidinyl)-1H-indazole-7-carboxamide hydrochloride (Example 2) (50 mg, 0.14 mmol), diisopropylethylamine (100 uL, 0.56 mmol), DMAP (25 mg, 0.014 mmol) and 4-cyanobenzenesulfonyl chloride (34 mg, 0.168 mmol) were reacted to give the title compound (28 mg, 41%).

LC/MS: 486.2 Rt. 2.12 min.

Example 15

3-(1-{[3-(dimethylamino)propyl]sulfonyl}-4-piperidinyl)-5-phenyl-1H-indazole-7-carboxamide

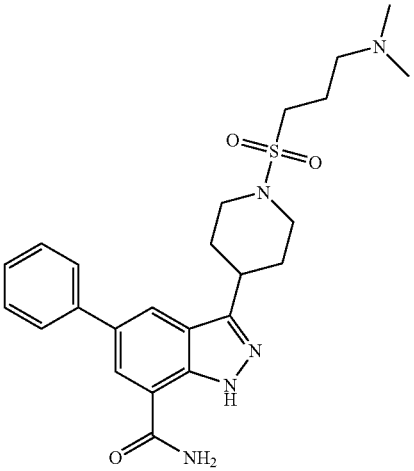 [SMILES: CN(C)CCCS(=O)(=O)N1CCC(c2n[nH]c3c(C(N)=O)cc(-c4ccccc4)cc23)CC1]

To a solution of 5-phenyl-3-(4-piperidinyl)-1H-indazole-7-carboxamide hydrochloride (Example 2) (50 mg, 0.14 mmol) in DMF (3 mL) was added diisopropylethylamine (100 uL, 0.56 mmol), DMAP (25 mg, 0.014 mmol) and 3-chloro-1-propanesulfonyl chloride (28 uL, 0.21 mmol). After the reaction mixture was stirred at room temperature for 2 hrs, sodium iodide (20 mg), K$_2$CO$_3$ (40 mg) and 2M dimethyl amine in DMF (0.32 mL) were added. The reaction mixture was stirred for 4 hrs. The solution was filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to afford the title compound (30 mg, 46%)

LC/MS: 470.4 Rt: 1.60 min.

Example 16

3-(1-{[2-(dimethylamino)ethyl]sulfonyl}-4-piperidinyl)-5-phenyl-1H-indazole-7-carboxamide

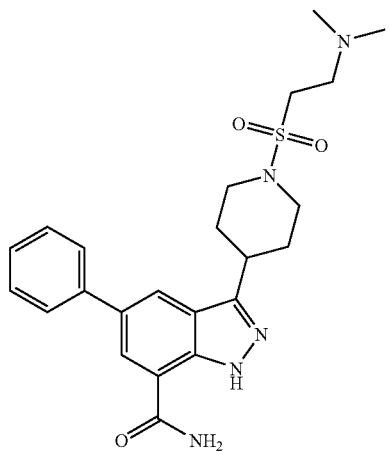 [SMILES: CN(C)CCS(=O)(=O)N1CCC(c2n[nH]c3c(C(N)=O)cc(-c4ccccc4)cc23)CC1]

To a solution 5-phenyl-3-(4-piperidinyl)-1H-indazole-7-carboxamide hydrochloride (Example 2) (50 mg, 0.14 mmol) in DMF (3 mL) was added diisopropylethylamine (100 uL, 0.56 mmol), DMAP (25 mg, 0.014 mmol) and 2-chloroethanesulfonyl chloride (25 uL, 0.21 mmol). After the reaction mixture was stirred at room temperature for 2 hrs, sodium iodide (20 mg), K₂CO₃ (40 mg) and 2M dimethyl amine in DMF (0.32 mL) were added. The reaction mixture was stirred for 4 hrs. The solution was filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to afford the title compound (10 mg, 16%)

LC/MS: 456.2 Rt: 1.51 min.

Example 17

3-{1-[(1,2-dimethyl-1H-imidazol-4-yl)sulfonyl]-4-piperidinyl}-5-{3-[(methylsulfonyl)amino]phenyl}-1H-indazole-7-carboxamide

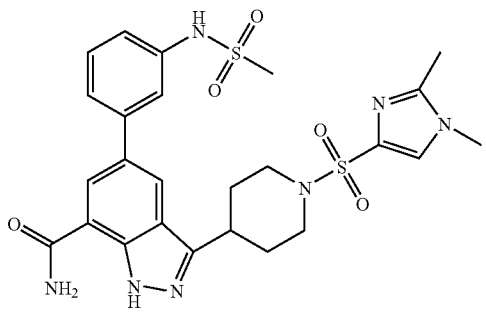 [SMILES: Cc1nc(S(=O)(=O)N2CCC(c3n[nH]c4c(C(N)=O)cc(-c5cccc(NS(C)(=O)=O)c5)cc34)CC2)cn1C]

Following the general procedure of Example 11, 5-{3-[(methylsulfonyl)-amino]phenyl}-3-(4-piperidinyl)-1H-indazole-7-carboxamide (Example 67) (0.07 mmol), diisopropylethylamine (100 uL, 0.56 mmol), DMAP (25 mg, 0.014 mmol) and 1,2-dimethyl-1H-imidazole-4-sulfonyl chloride (33 mg, 0.17 mmol) were reacted to give the title compound (5 mg, 13% for 3 steps).

LC/MS: 572.2 Rt: 1.64 min.

Example 18

5-[3-(acetylamino)phenyl]-3-{1-[(1,2-dimethyl-1H-imidazol-4-yl)sulfonyl]-4-piperidinyl}-1H-indazole-7-carboxamide

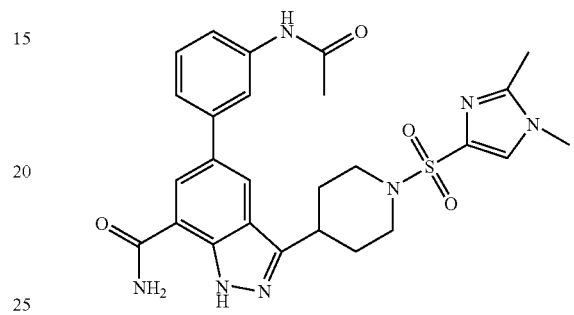

Following the general procedure of Example 11, 5-[3-(acetylamino)phenyl]-3-(4-piperidinyl)-1H-indazole-7-carboxamide (Example 69) (0.07 mmol), diisopropylethylamine (100 uL, 0.56 mmol), DMAP (25 mg, 0.014 mmol) and 1,2-dimethyl-1H-imidazole-4-sulfonyl chloride (33 mg, 0.17 mmol) were reacted to give the title compound (10 mg, 27% for 3 steps).

LC/MS: 536.4 Rt: 1.51 min.

Example 19

5-[4-(acetylamino)phenyl]-3-{1-[(1,2-dimethyl-1H-imidazol-4-yl)sulfonyl]-4-piperidinyl}-1H-indazole-7-carboxamide

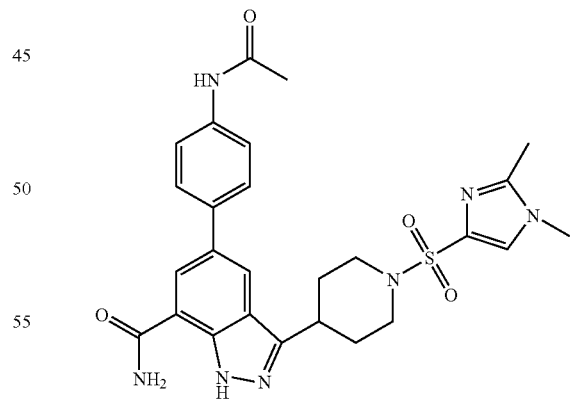

Following the general procedure of Example 11, 5-[4-(acetylamino)phenyl]-3-(4-piperidinyl)-1H-indazole-7-carboxamide (Example 71) (0.07 mmol), diisopropylethylamine (100 uL, 0.56 mmol), DMAP (25 mg, 0.014 mmol) and 1,2-dimethyl-1H-imidazole-4-sulfonyl chloride (33 mg, 0.17 mmol) were reacted to give the title compound (5 mg, 13% for 3 steps).

LC/MS: 536.4 Rt: 1.52 min.

Example 20

3-{1-[(1,2-dimethyl-1H-imidazol-4-yl)sulfonyl]-4-piperidinyl}-5-[4-(hydroxymethyl)phenyl]-1H-indazole-7-carboxamide

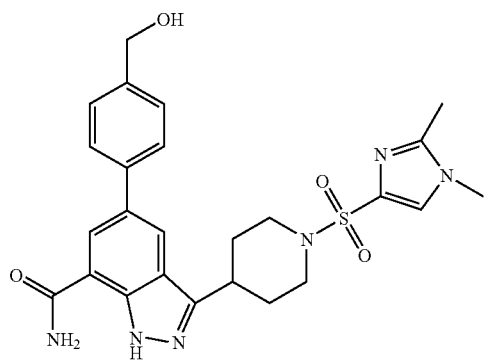 [SMILES: Cc1nc(S(=O)(=O)N2CCC(c3n[nH]c4c(C(N)=O)cc(-c5ccc(CO)cc5)cc34)CC2)cn1C]

Following the general procedure of Example 11, 5-[4-(hydroxymethyl)phenyl]-3-(4-piperidinyl)-1H-indazole-7-carboxamide (Example 73) (0.07 mmol), diisopropylethylamine (100 uL, 0.56 mmol), DMAP (25 mg, 0.014 mmol) and 1,2-dimethyl-1H-imidazole-4-sulfonyl chloride (33 mg, 0.17 mmol) were reacted to give the title compound (11 mg, 31% for 3 steps).

LC/MS: 509.2 Rt: 1.42 min.

Example 21

3-{1-[(1,2-dimethyl-1H-imidazol-4-yl)sulfonyl]-4-piperidinyl}-5-(1H-pyrazol-4-yl)-1H-indazole-7-carboxamide

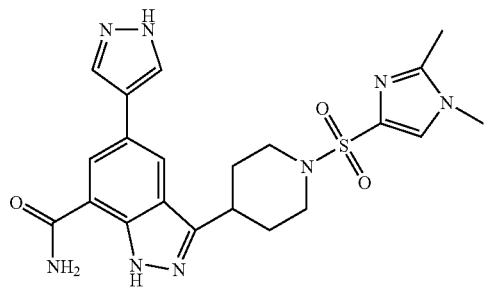 [SMILES: Cc1nc(S(=O)(=O)N2CCC(c3n[nH]c4c(C(N)=O)cc(-c5cn[nH]c5)cc34)CC2)cn1C]

Following the general procedure of Example 11, 3-(4-piperidinyl)-5-(1H-pyrazol-4-yl)-1H-indazole-7-carboxamide (Example 75) (0.07 mmol), diisopropyl-ethylamine (100 uL, 0.56 mmol), DMAP (25 mg, 0.014 mmol) and 1,2-dimethyl-1H-imidazole-4-sulfonyl chloride (33 mg, 0.17 mmol) were reacted to give the title compound (9 mg, 27% for 3 steps).
LC/MS: 469.4 Rt: 1.33 min.

Example 22

3-(1-{[3-(dimethylamino)propyl]sulfonyl}-4-piperidinyl)-5-{4-[(trifluoromethyl)oxy]phenyl}-1H-indazole-7-carboxamide

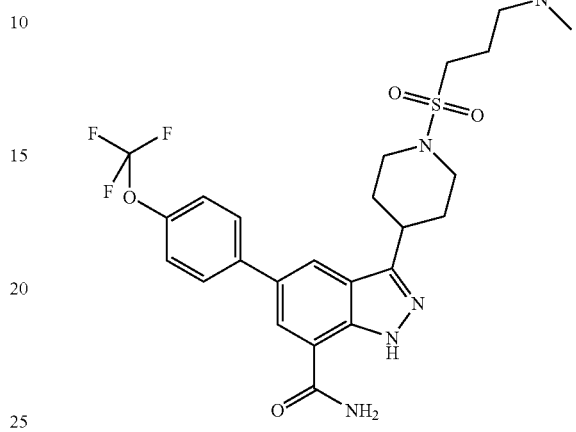

To a solution 5-bromo-3-(1-{[3-(dimethylamino)propyl]sulfonyl}-4-piperidinyl)-1H-indazole-7-carboxamide (Intermediate 8) (20 mg, 0.04 mmol) in dioxane/water (1:1, 5 mL) was added {4-[(trifluoromethyl)oxy]phenyl}boronic acid (30 mg, 0.12 mmol), potassium carbonate (40 mg), and Pd(dppf)Cl$_2$ (8 mg). The reaction mixture was heated at 100° C. for 1800 seconds. The contents of the vial were partitioned between ethyl acetate and water. The organic phase was washed with water, dried over MgSO$_4$, filtered, and concentrated to give 0.62 g of a yellow solid. This was purified via silica gel chromatography using 20% ethyl acetate/pentane as the mobile phase to give the title compound (5 mg, 23%).

LC/MS: 554.6 Rt: 1.77 min.

Example 23

5-(1H-pyrazol-4-yl)-3-(1-{[3-(1-pyrrolidinyl)propyl]sulfonyl}-4-piperidinyl)-1H-indazole-7-carboxamide

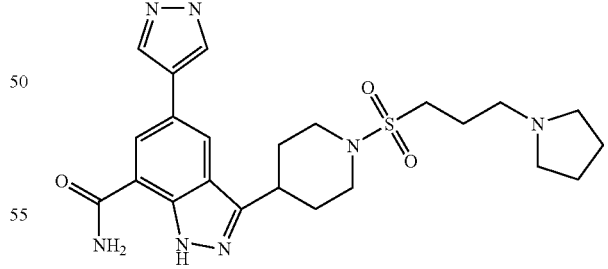

Following the general procedure of Example 66, a mixture of 5-bromo-3-(1-{[3-(1-pyrrolidinyl)propyl]sulfonyl}-4-piperidinyl)-1H-indazole-7-carboxamide (Intermediate 27) (24 mg, 0.048 mmols), 4-(4,4,5,5-tetramethyl-1,3,2-dioxaborolan-2-yl)-1H-pyrazole (28 mg, 0.144 mmols), potassium carbonate (40 mg), and Pd(PPh$_3$)$_4$ (3 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (10 mg, 43%)

LC/MS: 486.2 Rt. 1.24 min.

Example 24

5-{4-[(methylsulfonyl)amino]phenyl}-3-(1-{[3-(1-pyrrolidinyl)propyl]sulfonyl}-4-piperidinyl)-1H-indazole-7-carboxamide

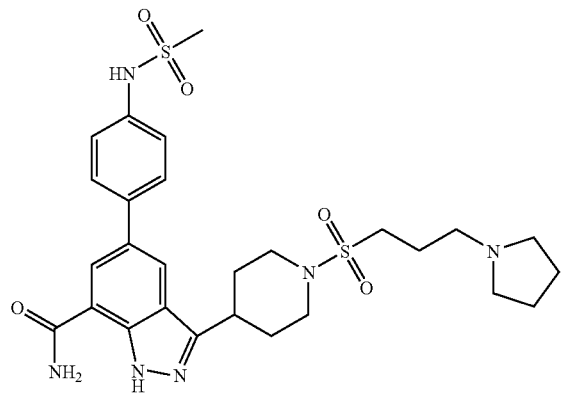 [SMILES: CS(=O)(=O)Nc1ccc(-c2cc(C(N)=O)c3[nH]nc(C4CCN(S(=O)(=O)CCCN5CCCC5)CC4)c3c2)cc1]

Following the general procedure of Example 66, a mixture of 5-bromo-3-(1-{[3-(1-pyrrolidinyl)propyl]sulfonyl}-4-piperidinyl)-1H-indazole-7-carboxamide (Intermediate 27) (24 mg, 0.048 mmols), {4-[(methylsulfonyl)amino]phenyl}boronic acid (31 mg, 0.144 mmols), potassium carbonate (40 mg), and Pd(PPh₃)₄ (3 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (15 mg, 53%)

LC/MS: 589.2 Rt. 1.39 min.

Example 25

5-{3-[(methylsulfonyl)amino]phenyl}-3-(1-{[3-(1-pyrrolidinyl)propyl]sulfonyl}-4-piperidinyl)-1H-indazole-7-carboxamide

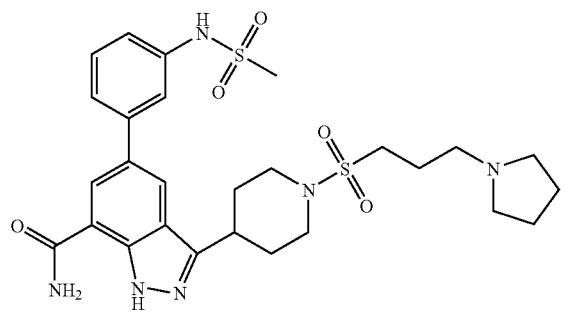 [SMILES: CS(=O)(=O)Nc1cccc(-c2cc(C(N)=O)c3[nH]nc(C4CCN(S(=O)(=O)CCCN5CCCC5)CC4)c3c2)c1]

Following the general procedure of Example 66, a mixture of 5-bromo-3-(1-{[3-(1-pyrrolidinyl)propyl]sulfonyl}-4-piperidinyl)-1H-indazole-7-carboxamide (Intermediate 27) (24 mg, 0.048 mmols), {3-[(methylsulfonyl)amino]phenyl}boronic acid (31 mg, 0.144 mmols), potassium carbonate (40 mg), and Pd(PPh₃)₄ (3 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (5 mg, 18%)

LC/MS: 589.2 Rt. 1.41 min.

Example 26

5-[4-(hydroxymethyl)phenyl]-3-(1-{[3-(1-pyrrolidinyl)propyl]sulfonyl}-4-piperidinyl)-1H-indazole-7-carboxamide

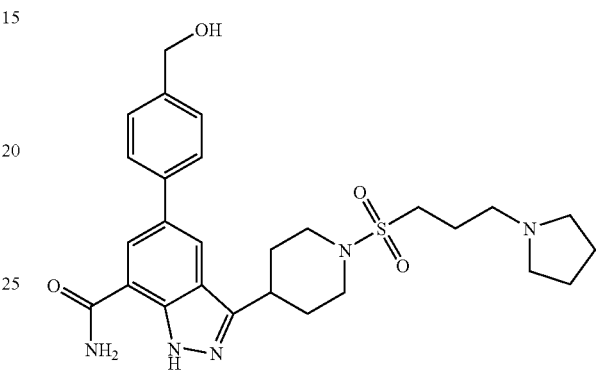

Following the general procedure of Example 66, a mixture of 5-bromo-3-(1-{[3-(1-pyrrolidinyl)propyl]sulfonyl}-4-piperidinyl)-1H-indazole-7-carboxamide (Intermediate 27) (50 mg, 0.10 mmols), [4-(hydroxymethyl)phenyl]boronic acid (50 mg, 0.30 mmols), cesium carbonate (200 mg), and Pd(PPh₃)₄ (5 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (15 mg, 29%)

LC/MS: 526.6 Rt. 1.46 min.

Example 27

5-[3-(hydroxymethyl)phenyl]-3-(1-{[3-(1-pyrrolidinyl)propyl]sulfonyl}-4-piperidinyl)-1H-indazole-7-carboxamide

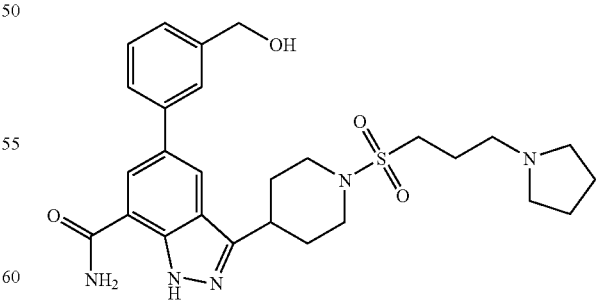

Following the general procedure of Example 66, a mixture of 5-bromo-3-(1-{[3-(1-pyrrolidinyl)propyl]sulfonyl}-4-piperidinyl)-1H-indazole-7-carboxamide (Intermediate 27) (100 mg, 0.20 mmols), [3-(hydroxymethyl)phenyl]boronic acid (91 mg, 0.60 mmols), cesium carbonate (400 mg), and Pd(PPh$_3$)$_4$ (10 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (20 mg, 19%)

LC/MS: 526.6 Rt. 1.46 min.

Example 28

5-(3,4-difluorophenyl)-3-[1-(ethylsulfonyl)-4-piperidinyl]-1H-indazole-7-carboxamide

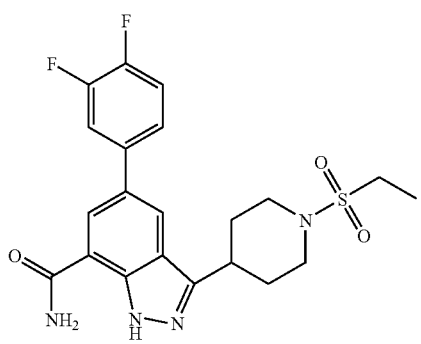 [SMILES: CCS(=O)(=O)N1CCC(c2n[nH]c3c(C(N)=O)cc(-c4ccc(F)c(F)c4)cc23)CC1]

Following the general procedure of Example 66, a mixture of 5-bromo-3-[1-(ethylsulfonyl)-4-piperidinyl]-1H-indazole-7-carbonitrile (Intermediate 10) (50 mg, 0.102 mmols), 3,4-difluorophenyl boronic acid (48 mg, 0.306 mmols), potassium carbonate (84 mg, 0.612 mmol), and chloro(di-2-norbonylphosphino)-(2-dimethylaminomethyl-ferrocen-1-yl)paladium (3 mg) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (11 mg, 24%)

LC/MS: 449.0 Rt. 2.06 min.

Example 29

5-(3,5-difluorophenyl)-3-[1-(ethylsulfonyl)-4-piperidinyl]-1H-indazole-7-carboxamide

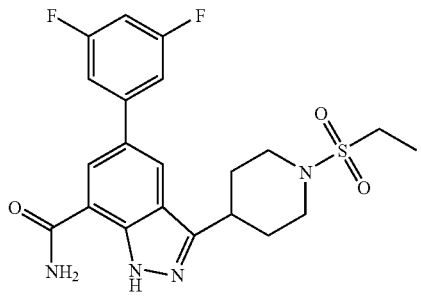 [SMILES: CCS(=O)(=O)N1CCC(c2n[nH]c3c(C(N)=O)cc(-c4cc(F)cc(F)c4)cc23)CC1]

Following the general procedure of Example 66, a mixture of 5-bromo-3-[1-(ethylsulfonyl)-4-piperidinyl]-1H-indazole-7-carbonitrile (Intermediate 10) (61.3 mg, 0.125 mmols), 3,5-difluorophenyl boronic acid (59 mg, 0.375 mmols), potassium carbonate (104 mg, 0.75 mmol), and chloro(di-2-norbonylphosphine)-(2-dimethylaminomethyl-forrocen-1-yl)palladium (15 mg, 0.025 mmol) in dioxane/water (3/1, 4 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H$_2$O (0.1% trifluoroacetic acid) and B=CH$_3$CN (0.1% trifluoroacetic acid) pumped at 25 mL/min to give the title compound (15 mg, 33%)

LC/MS: 449.0 Rt. 2.07 min.

Example 30

3-[1-(ethylsulfonyl)-4-piperidinyl]-5-(4-fluorophenyl)-1H-indazole-7-carboxamide

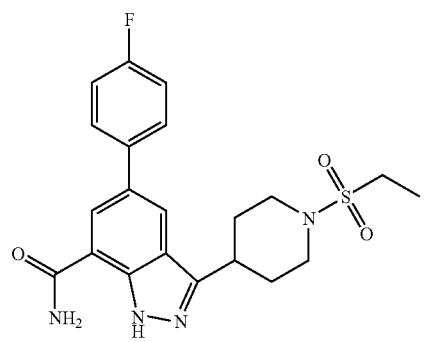 [SMILES: CCS(=O)(=O)N1CCC(c2n[nH]c3c(C(N)=O)cc(-c4ccc(F)cc4)cc23)CC1]

The mixture of 3-[1-(ethylsulfonyl)-4-piperidinyl]-5-(4-fluorophenyl)-1H-indazole-7-carbonitrile (Intermediate 11) (0.102 mmols) and potassium hydroxide (26 mg, 0.51 mmol) in 2-methyl-2-propanol (4 mL) was heated overnight. The reaction mixture was concentrated and purified by using a Gilson semi-preparative HPLC system with a YMC ODS-A (C-18) column 50 mm by 20 mm ID, eluting with 10% B to 70% B in 3.2 min, hold for 1 min where A=H$_2$O (0.1% trifluoroacetic acid) and B=CH$_3$CN (0.1% trifluoroacetic acid) pumped at 25 mL/min to afford the title compound (21 mg, 48% for 2 steps)

LC/MS: 431.0 Rt. 1.94 min.

Example 31

3-[1-(ethylsulfonyl)-4-piperidinyl]-5-(2-fluorophenyl)-1H-indazole-7-carboxamide

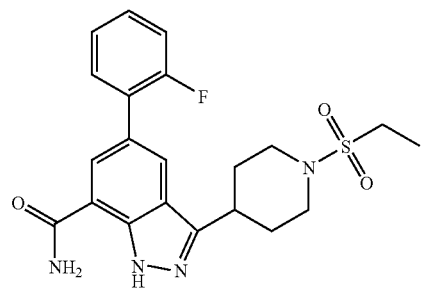 [SMILES: CCS(=O)(=O)N1CCC(c2n[nH]c3c(C(N)=O)cc(-c4ccccc4F)cc23)CC1]

The mixture of 3-[1-(ethylsulfonyl)-4-piperidinyl]-5-(2-fluorophenyl)-1H-indazole-7-carbonitrile (Intermediate 12) (0.102 mmols) and potassium hydroxide (26 mg, 0.51 mmol) in 2-methyl-2-propanol (4 mL) was heated overnight. The reaction mixture was concentrated. The residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to afford the title compound (11 mg, 25% for 2 steps)

LC/MS: 431.0 Rt. 1.95 min.

Example 32

3-[1-(ethylsulfonyl)-4-piperidinyl]-5-(3-fluorophenyl)-1H-indazole-7-carboxamide

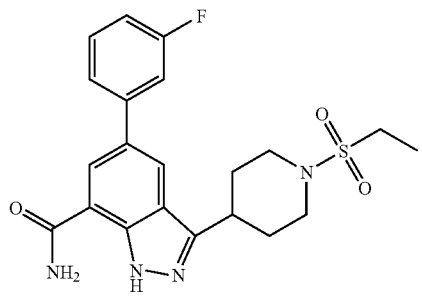 [SMILES: CCS(=O)(=O)N1CCC(c2n[nH]c3c(C(N)=O)cc(-c4cccc(F)c4)cc23)CC1]

Following the general procedure of Example 66, a mixture of 5-bromo-3-[1-(ethylsulfonyl)-4-piperidinyl]-1H-indazole-7-carboxamide (Intermediate 13) (30 mg, 0.072 mmols), 3-fluorophenyl boronic acid (30 mg, 0.216 mmols), potassium carbonate (60 mg, 0.433 mmol), and Pd(PPh₃)₄ (8 mg, 0.0072 mmol) in dioxane (2 mL) and water (1 mL) was reacted. The reaction mixture was concentrated, redissolved in methylene chloride and filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to give the title compound (6.57 mg, 21%)

LC/MS: 431.2 Rt. 1.96 min.

Example 33

5-(3-fluorophenyl)-3-(1-{[2-(1-pyrrolidinyl)ethyl]sulfonyl}-4-piperidinyl)-1H-indazole-7-carboxamide

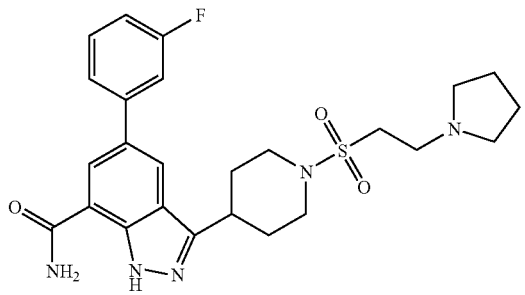 [SMILES: NC(=O)c1cc(-c2cccc(F)c2)cc2c(C3CCN(S(=O)(=O)CCN4CCCC4)CC3)n[nH]c12]

This compound was prepared in a fashion analogous to the procedure described in Example 16. Thus, 5-(3-fluorophenyl)-3-(4-piperidinyl)-1H-indazole-7-carboxamide (Intermediate 15) (75 mg, 0.167 mmol) was reacted with 2-chloro-1-ethanesulfonyl chloride (17 uL, 0.167 mmol) in the presence of triethyl amine (93 uL, 0.665 mmol) in DMF (2 mL) at 0° C. After 10 mins, K₂CO₃ (46 mg, 0.334 mmol) and pyrrolidine (41 uL, 0.501 mmol) were added. The reaction mixture was heated to 100° C. overnight. The resulting suspension was filtered. The filtrate was concentrated and the residue was purified by using a Gilson semi-preparative HPLC system, eluting with 10% B to 80% B, where A=H₂O (0.1% trifluoroacetic acid) and B=CH₃CN (0.1% trifluoroacetic acid) pumped at 25 mL/min to afford the title compound (12.6 mg, 15% for 2 steps).

LC/MS: 500.6 Rt: 1.51 min.

Example 34

3-(1-{[2-(diethylamino)ethyl]sulfonyl}-4-piperidinyl)-5-(3-fluorophenyl)-1H-indazole-7-carboxamide

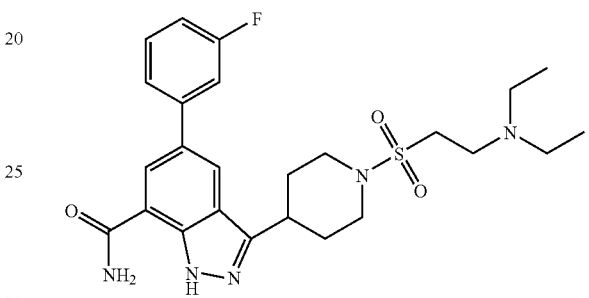

The title compound was prepared according to the procedure described in Example 33. Thus, 5-(3-fluorophenyl)-3-(4-piperidinyl)-1H-indazole-7-carboxamide (Intermediate 15) (75 mg, 0.167 mmol) was reacted with 2-chloro-1-ethanesulfonyl chloride (17 uL, 0.167 mmol) in the presence of triethyl amine (93 uL, 0.665 mmol) in DMF (2 mL) at 0° C. After 10 mins., K₂CO₃ (46 mg, 0.334 mmol) and diethyl amine (52 uL, 0.501 mmol) were added to afford the title compound (12.1 mg, 14% for 2 steps).

LC/MS: 502.4 Rt: 1.63 min.

Example 35

3-(1-{[2-(cyclopentylamino)ethyl]sulfonyl}-4-piperidinyl)-5-(3-fluorophenyl)-1H-indazole-7-carboxamide

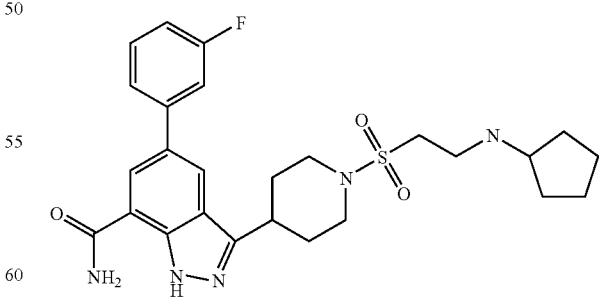

The title compound was prepared according to the procedure described in Example 33. Thus, 5-(3-fluorophenyl)-3-(4-piperidinyl)-1H-indazole-7-carboxamide (Intermediate 15) (75 mg, 0.167 mmol) was reacted with 2-chloro-1-ethanesulfonyl chloride (17 uL, 0.167 mmol) in the presence of triethyl amine (93 uL, 0.665 mmol) in DMF (2 mL) at 0° C. After 10 mins., K₂CO₃ (46 mg, 0.334 mmol) and cyclopentyl amine (49 uL, 0.501 mmol) were added to afford the title compound (4.9 mg, 8.1% for 2 steps).
LC/MS: 514.4 Rt: 1.64 min.

Example 36

3-(1-{[2-(1,4'-bipiperidin-1'-yl)ethyl]sulfonyl}-4-piperidinyl)-5-(3-fluorophenyl)-1H-indazole-7-carboxamide

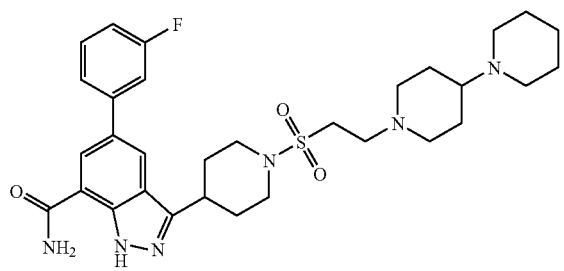 [SMILES: NC(=O)c1cc(-c2cccc(F)c2)cc2c(C3CCN(S(=O)(=O)CCN4CCC(N5CCCCC5)CC4)CC3)n[nH]c12]

The title compound was prepared according to the procedure described in Example 33. Thus, 5-(3-fluorophenyl)-3-(4-piperidinyl)-1H-indazole-7-carboxamide (Intermediate 15) (75 mg, 0.167 mmol) was reacted with 2-chloro-1-ethanesulfonyl chloride (17 uL, 0.167 mmol) in the presence of triethyl amine (93 uL, 0.665 mmol) in DMF (2 mL) at 0° C. After 10 mins., K₂CO₃ (46 mg, 0.334 mmol) and 4-piperidino-piperidine (84 mg, 0.501 mmol) were added to afford the title compound (22.6 mg, 23% for 2 steps).
LC/MS: 597.2 Rt: 1.44 min Example 37

5-(3-fluorophenyl)-3-(1-{[2-(4-hydroxy-1-piperidinyl)ethyl]sulfonyl}-4-piperidinyl)-1H-indazole-7-carboxamide

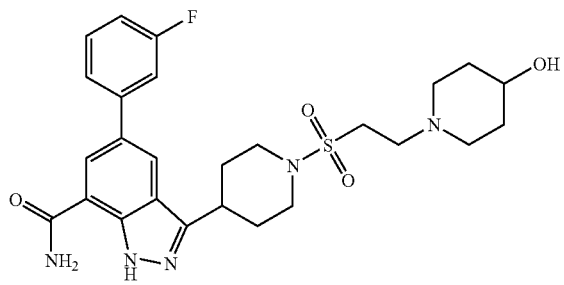 [SMILES: NC(=O)c1cc(-c2cccc(F)c2)cc2c(C3CCN(S(=O)(=O)CCN4CCC(O)CC4)CC3)n[nH]c12]

The title compound was prepared according to the procedure described in Example 33. Thus, 5-(3-fluorophenyl)-3-(4-piperidinyl)-1H-indazole-7-carboxamide (Intermediate 15) (75 mg, 0.167 mmol) was reacted with 2-chloro-1-ethanesulfonyl chloride (17 uL, 0.167 mmol) in the presence of triethyl amine (93 uL, 0.665 mmol) in DMF (2 mL) at 0° C. After 10 mins., K₂CO₃ (46 mg, 0.334 mmol) and 4-piperidinol (51 mg, 0.501 mmol) were added to afford the title compound (17.9 mg, 20% for 2 steps).
LC/MS: 530.0 Rt: 1.44 min Example 38

3-(1-{[3-(diethylamino)propyl]sulfonyl}-4-piperidinyl)-5-(3-fluorophenyl)-1H-indazole-7-carboxamide

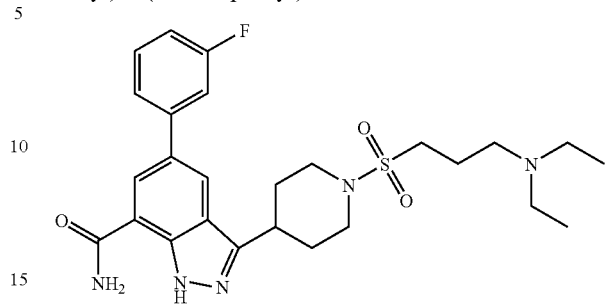

38a) 3-{1-[(3-chloropropyl)sulfonyl]-4-piperidinyl}-5-(3-fluorophenyl)-1H-indazole-7-carboxamide This compound was prepared in a fashion analogous to the procedure described in Example 3. Thus, 5-(3-fluorophenyl)-3-(4-piperidinyl)-1H-indazole-7-carboxamide (Intermediate 15) (106 mg, 0.222 mmol) was reacted with 3-chloropropane sulfonyl chloride (34 uL, 0.275 mmol) in the presence of triethyl amine (124 uL, 0.888 mmol) in DMF (4 mL) to give 3-{1-[(3-chloropropyl)sulfonyl]-4-piperidinyl}-5-(3-fluorophenyl)-1H-indazole-7-carboxamide, which was used in the next step without further purification.

38b) 3-(1-{[3-(diethylamino)propyl]sulfonyl}-4-piperidinyl)-5-(3-fluorophenyl)-1H-indazole-7-carboxamide To a solution of 3-{1-[(3-chloropropyl)sulfonyl]-4-piperidinyl}-5-(3-fluorophenyl)-1H-indazole-7-carboxamide (0.222 mmol) in DMF (4 mL) was added K₂CO₃ (61 mg, 0.444 mmol) and diethyl amine (115 uL, 1.11 mmol). The reaction mixture was heated to 100° C. overnight. The solution was filtered and the filtrate was purified by using a Gilson semi-preparative HPLC system with a YMC ODS-A (C-18) column 50 mm by 20 mm ID, eluting with 10% B to 80% B in 10 min, hold for 1 min where A=H₂O (0.1% trifluoroacetic acid) and B=CH₃CN (0.1% trifluoroacetic acid) pumped at 25 mL/min to afford the title compound (24.7 mg, 22% for 2 steps).
LC/MS: 516.4 Rt: 1.71 min.

Example 39

5-(3-fluorophenyl)-3-(1-{[3-(1-pyrrolidinyl)propyl]sulfonyl}-4-piperidinyl)-1H-indazole-7-carboxamide

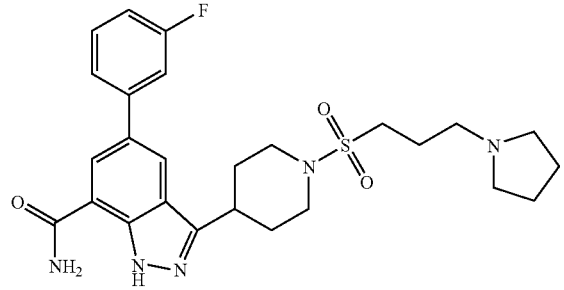 [SMILES: NC(=O)c1cc(-c2cccc(F)c2)cc2c(C3CCN(S(=O)(=O)CCCN4CCCC4)CC3)n[nH]c12]

The title compound was prepared according to the general procedure of Example 38b. Thus, 3-{1-[(3-chloropropyl)sulfonyl]-4-piperidinyl}-5-(3-fluorophenyl)-1H-indazole-7-carboxamide (Example 38a) (0.222 mmol) in DMF (4 mL) was reacted with K₂CO₃ (61 mg, 0.444 mmol) and pyrrolidine (92 uL, 1.11 mmol) to afford the title compound (23.5 mg, 21% for 2 steps).

LC/MS: 514.4 Rt: 1.61 min

Example 40

3-(1-{[3-(cyclopentylamino)propyl]sulfonyl}-4-piperidinyl)-5-(3-fluorophenyl)-1H-indazole-7-carboxamide

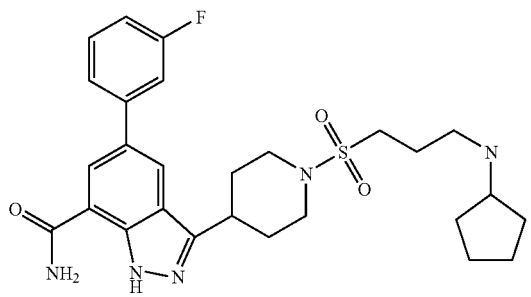 [SMILES: NC(=O)c1cc(-c2cccc(F)c2)cc2c(C3CCN(S(=O)(=O)CCCNC4CCCC4)CC3)n[nH]c12]

The title compound was prepared according to the general procedure of Example 38b. Thus, 3-{1-[(3-Chloropropyl)sulfonyl]-4-piperidinyl}-5-(3-fluorophenyl)-1H-indazole-7-carboxamide (Example 38a) (0.222 mmol) in DMF (4 mL) was reacted with K₂CO₃ (61 mg, 0.444 mmol) and cyclopentyl amine (110 uL, 1.11 mmol) to afford the title compound (8 mg, 7% for 2 steps).

LC/MS: 528.4 Rt: 1.75 min

Example 41

3-(1-{[3-(1,4'-bipiperidin-1'-yl)propyl]sulfonyl}-4-piperidinyl)-5-(3-fluorophenyl)-1H-indazole-7-carboxamide

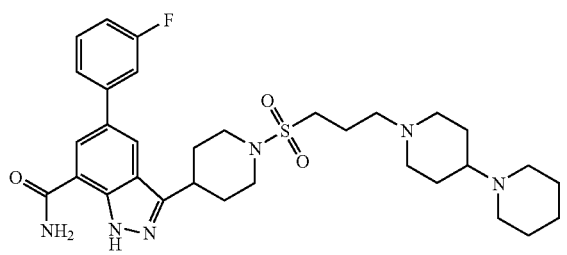 [SMILES: NC(=O)c1cc(-c2cccc(F)c2)cc2c(C3CCN(S(=O)(=O)CCCN4CCC(N5CCCCC5)CC4)CC3)n[nH]c12]

The title compound was prepared according to the general procedure of Example 38b. Thus, 3-{1-[(3-Chloropropyl)sulfonyl]-4-piperidinyl}-5-(3-fluorophenyl)-1H-indazole-7-carboxamide (Example 38a) (0.222 mmol) in DMF (4 mL) was reacted with K₂CO₃ (61 mg, 0.444 mmol) and 4-piperidino-piperidine (187 mg, 1.11 mmol) to afford the title compound (53.14 mg, 39% for 2 steps).

LC/MS: 611.2 Rt: 1.53 min

Example 42

5-(3-fluorophenyl)-3-(1-{[3-(4-hydroxy-1-piperidinyl)propyl]sulfonyl}-4-piperidinyl)-1H-indazole-7-carboxamide

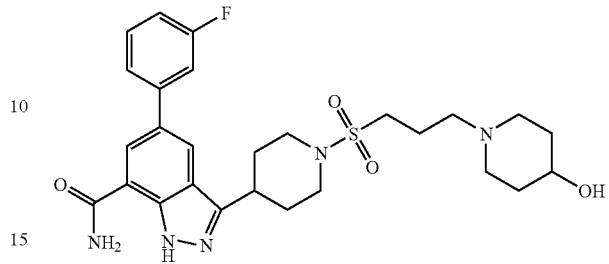

The title compound was prepared according to the general procedure of Example 38b. Thus, 3-{1-[(3-Chloropropyl)sulfonyl]-4-piperidinyl}-5-(3-fluorophenyl)-1H-indazole-7-carboxamide (Example 38a) (0.222 mmol) in DMF (4 mL) was reacted with K₂CO₃ (61 mg, 0.444 mmol) and 4-hydroxy piperidine (112 mg, 1.11 mmol) to afford the title compound (32.07 mg, 27% for 2 steps).

LC/MS: 544.4 Rt: 1.49 min

Example 43

5-(3-fluorophenyl)-3-(1-{[3-(4-morpholinyl)propyl]sulfonyl}-4-piperidinyl)-1H-indazole-7-carboxamide

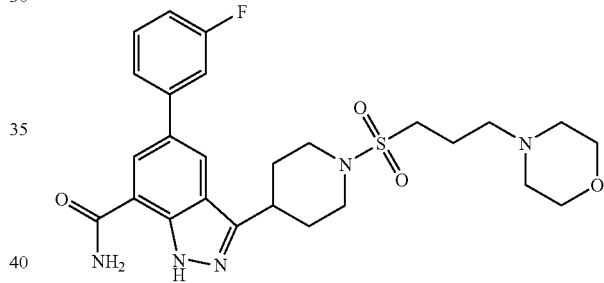

The title compound was prepared according to the general procedure of Example 38b. Thus, 3-{1-[(3-Chloropropyl)sulfonyl]-4-piperidinyl}-5-(3-fluorophenyl)-1H-indazole-7-carboxamide (Example 38a) (0.222 mmol) in DMF (4 mL) was reacted with K₂CO₃ (61 mg, 0.444 mmol) and morpholine (97 uL, 1.11 mmol) to afford the title compound (37.73 mg, 32% for 2 steps).

LC/MS: 530.2 Rt: 1.45 min

Example 44

3-[1-(ethylsulfonyl)-4-piperidinyl]-5-(2-thienyl)-1H-indazole-7-carboxamide

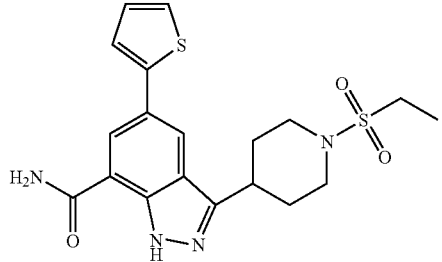 [SMILES: CCS(=O)(=O)N1CCC(c2n[nH]c3c(C(N)=O)cc(-c4cccs4)cc23)CC1]

This compound was prepared in a fashion analogous to the procedure described in Example 3. Thus, 3-(4-piperidinyl)-

5-(2-thienyl)-1H-indazole-7-carboxamide hydrochloride (Intermediate 17) (0.117 mmol) was reacted with ethane sulfonyl chloride (0.02 mL, 0.234 mmol) in the presence of triethylamine (0.04 mL, 0.468 mmol) in methylene chloride (10 mL) to give the title compound (4.9 mg, 10% for the last two steps)
LC/MS: 419.4 Rt: 1.92 min

Example 45

3-[1-(ethylsulfonyl)-4-piperidinyl]-5-(3-thienyl)-1H-indazole-7-carboxamide

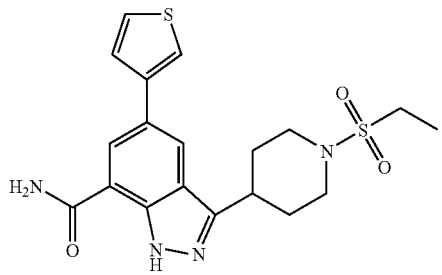 [SMILES: CCS(=O)(=O)N1CCC(c2n[nH]c3c(C(N)=O)cc(-c4ccsc4)cc23)CC1]

This compound was prepared in a fashion analogous to the procedure described in Example 3. Thus, 3-(4-piperidinyl)-5-(3-thienyl)-1H-indazole-7-carboxamide hydrochloride (Intermediate 19) (0.117 mmol) was reacted with ethane sulfonyl chloride (0.02 mL, 0.234 mmol) in the presence of triethylamine (0.04 mL, 0.468 mmol) in methylene chloride (10 mL) to give the title compound (9.4 mg, 19% for the last two steps)
LC/MS: 419.4 Rt: 1.85 min

Example 46

3-(1-{[3-(1-pyrrolidinyl)propyl]sulfonyl}-4-piperidinyl)-5-(2-thienyl)-1H-indazole-7-carboxamide

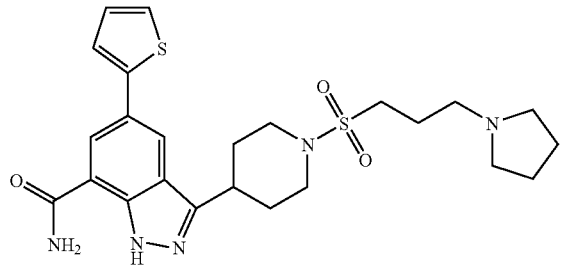 [SMILES: NC(=O)c1cc(-c2cccs2)cc2c(C3CCN(S(=O)(=O)CCCN4CCCC4)CC3)n[nH]c12]

46a) 3-{1-[(3-chloropropyl)sulfonyl]-4-piperidinyl}-5-(2-thienyl)-1H-indazole-7-carboxamide This compound was prepared in a fashion analogous to the procedure described in Example 38a. Thus, 3-(4-piperidinyl)-5-(2-thienyl)-1H-indazole-7-carboxamide hydrochloride (Intermediate 17) (25 mg, 0.076 mmol) was reacted with 3-chloropropane sulfonyl chloride (30 uL, 0.242 mmol) in DMF (4 mL) to give 3-{1-[(3-chloropropyl)sulfonyl]-4-piperidinyl}-5-(2-thienyl)-1H-indazole-7-carboxamide, which was used in the next step without further purification.

46b) 3-(1-{[3-(1-pyrrolidinyl)propyl]sulfonyl}-4-piperidinyl)-5-(2-thienyl)-1H-indazole-7-carboxamide The title compound was prepared according to the general procedure of Example 38b. Thus, 3-{1-[(3-chloropropyl)sulfonyl]-4-piperidinyl}-5-(2-thienyl)-1H-indazole-7-carboxamide (0.076 mmol) in DMF (4 mL) was reacted with $K_2CO_3$ (22 mg, 0.16 mmol), sodium iodide (2 mg) and pyrrolidine (26.98 mg, 0.4 mmol) to afford the title compound (16.2 mg, 42%).
LC/MS: 502.4 Rt: 1.58 min

Example 47

3-(1-{[3-(dimethylamino)propyl]sulfonyl}-4-piperidinyl)-5-(2-thienyl)-1H-indazole-7-carboxamide

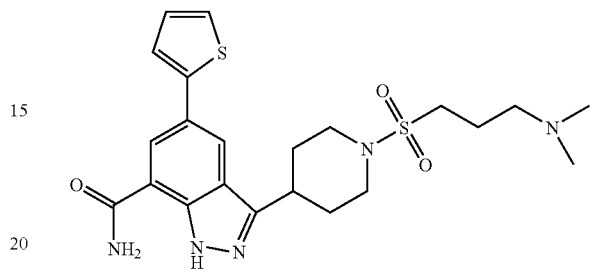

The title compound was prepared according to the general procedure of Example 38b. Thus, 3-{1-[(3-chloropropyl)sulfonyl]-4-piperidinyl}-5-(2-thienyl)-1H-indazole-7-carboxamide (Example 46a) (0.076 mmol) in DMF (4 mL) was reacted with $K_2CO_3$ (22 mg, 0.16 mmol), sodium iodide (2 mg) and dimethyl amine (0.2 mL, 0.4 mmol) to afford the title compound (13.9 mg, 38%).
LC/MS: 476.2 Rt: 1.52 min

Example 48

3-(1-{[3-(1-pyrrolidinyl)propyl]sulfonyl}-4-piperidinyl)-5-(3-thienyl)-1H-indazole-7-carboxamide

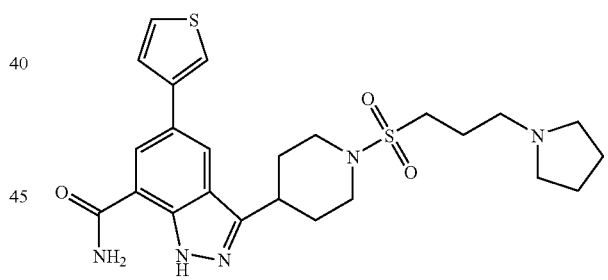

48a) 3-{1-[(3-chloropropyl)sulfonyl]-4-piperidinyl}-5-(3-thienyl)-1H-indazole-7-carboxamide This compound was prepared in a fashion analogous to the procedure described in Example 38a. Thus, 3-(4-piperidinyl)-5-(3-thienyl)-1H-indazole-7-carboxamide hydrochloride (Intermediate 19) (25 mg, 0.076 mmol) was reacted with 3-chloropropane sulfonyl chloride (30 uL, 0.242 mmol) in DMF (4 mL) to give 3-{1-[(3-chloropropyl)sulfonyl]-4-piperidinyl}-5-(3-thienyl)-1H-indazole-7-carboxamide, which was used in the next step without further purification.

48b) 3-(1-{[3-(1-pyrrolidinyl)propyl]sulfonyl}-4-piperidinyl)-5-(3-thienyl)-1H-indazole-7-carboxamide The title compound was prepared according to the general procedure of Example 38b. Thus, 3-{1-[(3-chloropropyl)sulfonyl]-4-piperidinyl}-5-(3-thienyl)-1H-indazole-7-carboxamide (0.076 mmol) in DMF (4 mL) was reacted with K₂CO₃ (22 mg, 0.16 mmol), sodium iodide (2 mg) and pyrrolidine (26.98 mL, 0.4 mmol) to afford the title compound (14.2 mg, 37%).

LC/MS: 502.4 Rt: 1.53 min

Example 49

3-(1-{[3-(dimethylamino)propyl]sulfonyl}-4-piperidinyl)-5-(3-thienyl)-1H-indazole-7-carboxamide

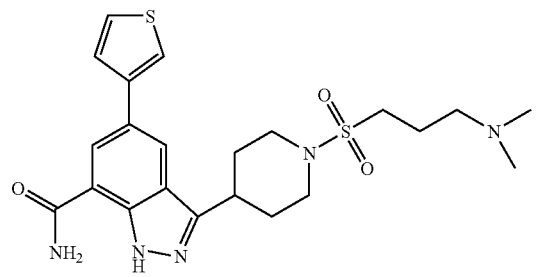 [SMILES: CN(C)CCCS(=O)(=O)N1CCC(c2n[nH]c3c(C(N)=O)cc(-c4ccsc4)cc23)CC1]

The title compound was prepared according to the general procedure of Example 38b. Thus, 3-{1-[(3-chloropropyl)sulfonyl]-4-piperidinyl}-5-(3-thienyl)-1H-indazole-7-carboxamide (Example 48a) (0.076 mmol) in DMF (4 mL) was reacted with K₂CO₃ (22 mg, 0.16 mmol), sodium iodide (2 mg) and dimethyl amine (0.2 mL, 0.4 mmol) to afford the title compound (16.9 mg, 47%).

LC/MS: 476.4 Rt: 1.51 min

Example 50

3-[1-(ethylsulfonyl)-4-piperidinyl]-5-(3-pyridinyl)-1H-indazole-7-carboxamide

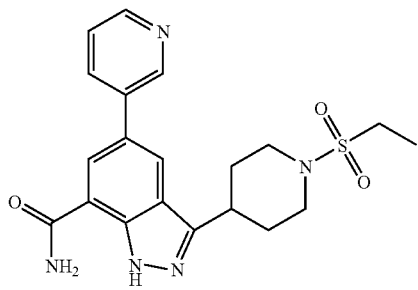 [SMILES: CCS(=O)(=O)N1CCC(c2n[nH]c3c(C(N)=O)cc(-c4cccnc4)cc23)CC1]

This compound was prepared in a fashion analogous to the procedure described in Example 3. Thus 3-(4-piperidinyl)-5-(3-pyridinyl)-1H-indazole-7-carboxamide hydrochloride (Intermediate 21) (0.09 mmol) was reacted with ethane sulfonyl chloride (0.01 mL, 0.217 mmol) in the presence of triethylamine (0.04 mL, 0.468 mmol) in methylene chloride (10 mL) to give the title compound (4.9 mg, 13% for the last two steps)

LC/MS: 414.4 Rt: 1.31 min

Example 51

3-(1-{[3-(4-morpholinyl)propyl]sulfonyl}-4-piperidinyl)-5-(2-thienyl)-1H-indazole-7-carboxamide

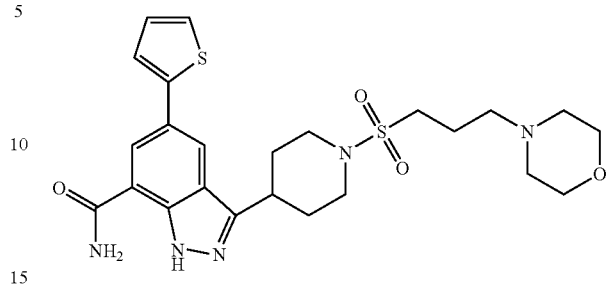

The title compound was prepared according to the general procedure of Example 38b. Thus, 3-{1-[(3-chloropropyl)sulfonyl]-4-piperidinyl}-5-(2-thienyl)-1H-indazole-7-carboxamide (Example 48a) (0.1 mmol) in DMF (2 mL) was reacted with K₂CO₃ (27.6 mg, 0.2 mmol), triethyl amine (83 uL, 0.6 mmol) and morpholine (43 uL, 0.5 mmol) to afford the title compound (29.4 mg, 57%).

LC/MS: 518.4 Rt: 1.58 min

Example 52

3-(1-{[3-(4-morpholinyl)propyl]sulfonyl}-4-piperidinyl)-5-(3-thienyl)-1H-indazole-7-carboxamide

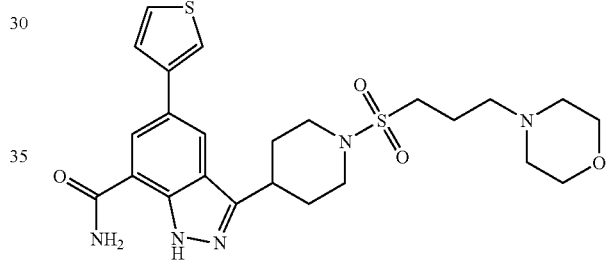

The title compound was prepared according to the general procedure of Example 38b. Thus, 3-{1-[(3-chloropropyl)sulfonyl]-4-piperidinyl}-5-(3-thienyl)-1H-indazole-7-carboxamide (Example 48a) (0.05 mmol) in DMF (2 mL) was reacted with K₂CO₃ (14 mg, 0.1 mmol), triethyl amine (42 uL, 0.3 mmol) and morpholine (22 uL, 0.25 mmol) to afford the title compound (2.3 mg, 8.8%).

LC/MS: 518.4 Rt: 1.57 min

Example 53

3-(1-{[4-(methyloxy)phenyl]sulfonyl}-4-piperidinyl)-5-phenyl-1H-indazole-7-carboxamide

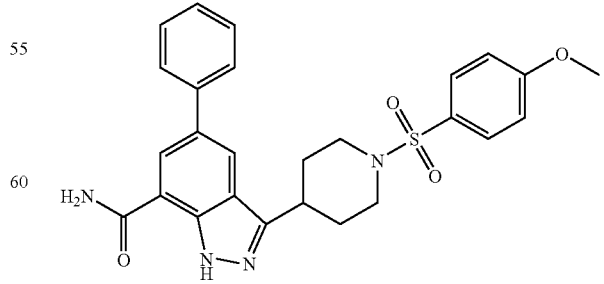

The crude 5-phenyl-3-(4-piperidinyl)-1H-indazole-7-carboxamide hydrochloride (21.1 mg, 0.066 mmol) (Example 2) was suspended in dichloromethane (8 mL) and treated with diisopropylethyl amine (46 uL, 0.264 mmols), DMAP (8 mg, 0.065 mmol), and 4-(methyloxy)benzenesulfonyl chloride (21 mg, 0.1 mmols) at 0° C. After 12 hrs, the mixture was concentrated to dryness in vacuo at ambient temperature, treated with water (10 mL), and extracted with ethyl acetate (3×25 mL). The organic phase was washed with water, dried over MgSO₄, filtered, and concentrated to give a light brown solid. This was purified via preparative HPLC eluting with 10% B to 80% B, where A=H₂O (0.1% trifluoroacetic acid) and B=CH₃CN (0.1% trifluoroacetic acid) to give the title compound (16 mg, 55%).

LC/MS: 491.2 Rt: 2.19 min

Example 54

5-phenyl-3-[1-(2-thienylsulfonyl)-4-piperidinyl]-1H-indazole-7-carbox-amide

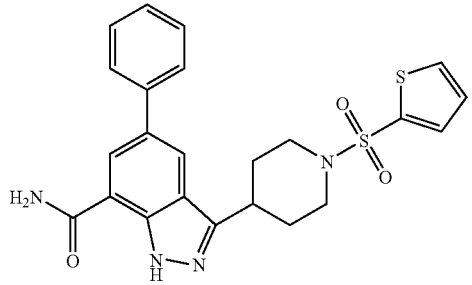 [SMILES: NC(=O)c1cc(-c2ccccc2)cc2c(C3CCN(S(=O)(=O)c4cccs4)CC3)n[nH]c12]

The crude 5-phenyl-3-(4-piperidinyl)-1H-indazole-7-carboxamide hydrochloride (20 mg, 0.06 mmol) (Example 2) was suspended in dichloromethane (2 mL) and treated with diisopropylethyl amine (46 uL, 0.24 mmols), DMAP (8 mg, 0.06 mmol), and 2-thiephenesulfonyl chloride (19 mg, 0.09 mmols) at 0° C. After 12 hrs, the mixture was concentrated to dryness in vacuo at ambient temperature, treated with water (10 mL), and extracted with ethyl acetate (3×25 mL). The organic phase was washed with water, dried over MgSO₄, filtered, and concentrated to give a light brown solid. This was purified via preparative HPLC eluting with 10% B to 80% B, where A=H₂O (0.1% trifluoroacetic acid) and B=CH₃CN (0.1% trifluoroacetic acid) to give the title compound (6.8 mg, 24%).

LC/MS: 467.2 Rt: 2.2 min

Example 55

5-phenyl-3-(1-{[3-(1-pyrrolidinyl)propyl]sulfonyl}-4-piperidinyl)-1H-indazole-7-carboxamide

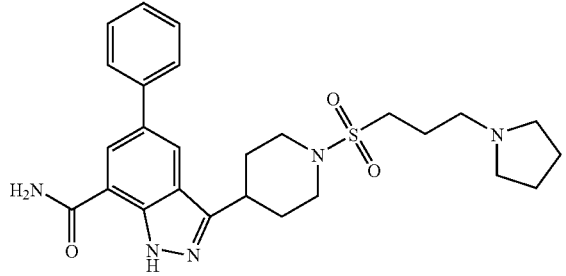 [SMILES: NC(=O)c1cc(-c2ccccc2)cc2c(C3CCN(S(=O)(=O)CCCN4CCCC4)CC3)n[nH]c12]

To a solution of 3-{1-[(3-chloropropyl)sulfonyl]-4-piperidinyl}-5-phenyl-1H-indazole-7-carboxamide (Intermediate 22) (18 mg, 0.039 mmol) in acetonitrile (2 mL) was added K₂CO₃ (25 mg, 0.156 mmol), pyrrolidine (19 uL, 0.196 mmol) and sodium iodide (0.7 mg, 0.0039 mmol). The reaction mixture was heated to 60° C. overnight. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 1 min where A=H₂O (0.1% trifluoroacetic acid) and B=CH₃CN (0.1% trifluoroacetic acid) pumped at 25 mL/min to afford the title compound (5.5 mg, 28%).

LC/MS: 496.4 Rt: 1.59 min.

Example 56

3-(1-{[3-(cyclobutylamino)propyl]sulfonyl}-4-piperidinyl)-5-phenyl-1H-indazole-7-carboxamide

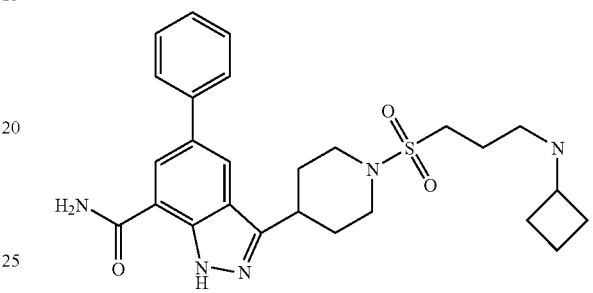

To a solution of 3-{1-[(3-chloropropyl)sulfonyl]-4-piperidinyl}-5-phenyl-1H-indazole-7-carboxamide (Intermediate 22) (20 mg, 0.0435 mmol) in DMF (1 mL) was added K₂CO₃ (27 mg, 0.174 mmol), cyclobutyl amine (18 uL, 0.217 mmol) and sodium iodide (0.8 mg, 0.00438 mmol). The reaction mixture was heated to 120° C. for 14 hrs. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 1 min where A=H₂O (0.1% trifluoroacetic acid) and B=CH₃CN (0.1% trifluoroacetic acid) pumped at 25 mL/min to afford the title compound (4.1 mg, 19%).

LC/MS: 496.4 Rt: 1.58 min.

Example 57

3-(1-{[3-(4-morpholinyl)propyl]sulfonyl}-4-piperidinyl)-5-phenyl-1H-indazole-7-carboxamide

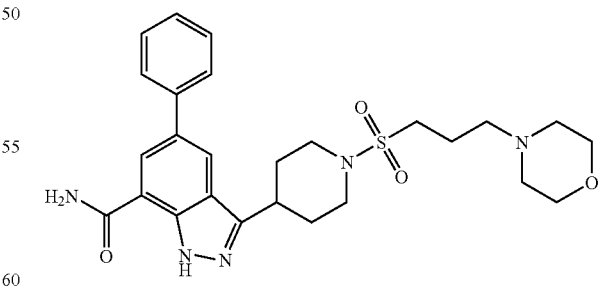

To a solution of 3-{1-[(3-chloropropyl)sulfonyl]-4-piperidinyl}-5-phenyl-1H-indazole-7-carboxamide (Intermediate 22) (20 mg, 0.0435 mmol) in acetonitrile (1 mL) was added K₂CO₃ (27 mg, 0.174 mmol), morpholine (19 uL, 0.219 mmol) and sodium iodide (0.8 mg, 0.00435 mmol). The reaction mixture was heated to 60° C. for 14 hrs. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 1 min where A=H₂O (0.1% trifluoroacetic acid) and B=CH₃CN (0.1% trifluoroacetic acid) pumped at 25 mL/min to afford the title compound (3.6 mg, 16%).

LC/MS: 512.4 Rt: 1.54 min.

Example 58

5-phenyl-3-(1-{[3-(1-piperazinyl)propyl]sulfonyl}-4-piperidinyl)-1H-indazole-7-carboxamide

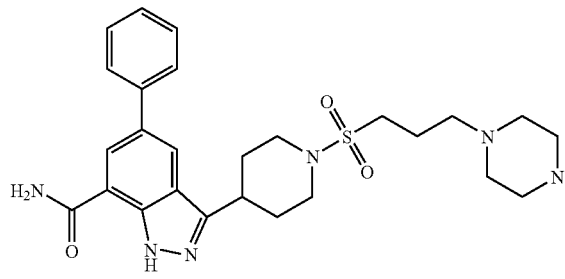 [SMILES: NC(=O)c1cc(-c2ccccc2)cc2c(C3CCN(S(=O)(=O)CCCN4CCNCC4)CC3)n[nH]c12]

To a solution of 3-{1-[(3-chloropropyl)sulfonyl]-4-piperidinyl}-5-phenyl-1H-indazole-7-carboxamide (Intermediate 22) (20 mg, 0.0435 mmol) in acetonitrile (1 mL) was added K₂CO₃ (27 mg, 0.174 mmol), piperazine (18.9 mg, 0.219 mmol) and sodium iodide (0.8 mg, 0.00435 mmol). The reaction mixture was heated to 60° C. for 14 hrs. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 0.1 min where A=H₂O (0.1% trifluoroacetic acid) and B=CH₃CN (0.1% trifluoroacetic acid) pumped at 25 mL/min to afford the title compound (11.0 mg, 49%).

LC/MS: 511.2 Rt: 1.25 min.

Example 59

3-[1-({3-[3-(2-hydroxyethyl)-1-piperazinyl]propyl}sulfonyl)-4-piperidinyl]-5-phenyl-1H-indazole-7-carboxamide

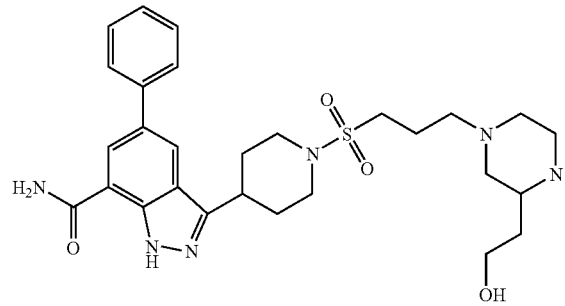 [SMILES: NC(=O)c1cc(-c2ccccc2)cc2c(C3CCN(S(=O)(=O)CCCN4CCNC(CCO)C4)CC3)n[nH]c12]

To a solution of 3-{1-[(3-chloropropyl)sulfonyl]-4-piperidinyl}-5-phenyl-1H-indazole-7-carboxamide (Intermediate 22) (20 mg, 0.0435 mmol) in acetonitrile (1 mL) was added K₂CO₃ (27 mg, 0.174 mmol), 2-(2-piperazinyl)ethanol (20 uL, 0.219 mmol) and sodium iodide (0.8 mg, 0.00435 mmol). The reaction mixture was heated to 60° C. for 14 hrs. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 1 min where A=H₂O (0.1% trifluoroacetic acid) and B=CH₃CN (0.1% trifluoroacetic acid) pumped at 25 mL/min to afford the title compound (7.0 mg, 30%).

LC/MS: 555.4 Rt: 1.38 min.

Example 60

3-(1-{[3-(cyclopentylamino)propyl]sulfonyl}-4-piperidinyl)-5-phenyl-1H-indazole-7-carboxamide

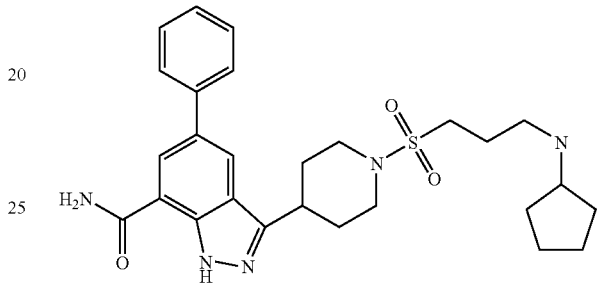

To a solution of 3-{1-[(3-chloropropyl)sulfonyl]-4-piperidinyl}-5-phenyl-1H-indazole-7-carboxamide (Intermediate 22) (19 mg, 0.0413 mmol) in DMF (1 mL) was added K₂CO₃ (25 mg, 0.165 mmol), cyclopentylamine (22 uL, 0.2065 mmol) and sodium iodide (1.0 mg). The reaction mixture was heated to 120° C. for 14 hrs. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 1 min where A=H₂O (0.1% trifluoroacetic acid) and B=CH₃CN (0.1% trifluoroacetic acid) pumped at 25 mL/min to afford the title compound (5.5 mg, 26%).

LC/MS: 510.4 Rt: 1.67 min.

Example 61

3-[1-({3-[(4-hydroxycyclohexyl)amino]propyl}sulfonyl)-4-piperidinyl]-5-phenyl-1H-indazole-7-carboxamide

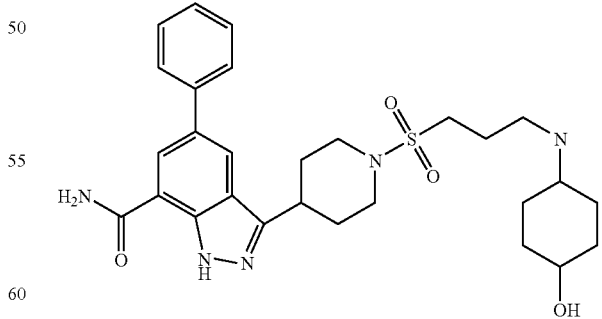

To a solution of 3-{1-[(3-chloropropyl)sulfonyl]-4-piperidinyl}-5-phenyl-1H-indazole-7-carboxamide (Intermediate 22) (19 mg, 0.0413 mmol) in DMF (1 mL) was added K₂CO₃ (25 mg, 0.165 mmol), 4-hydroxycyclohexylamine (33 mg, 0.2065 mmol) and sodium iodide (1.0 mg). The reaction mixture was heated to 120° C. for 14 hrs. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 1 min where A=$H_2O$ (0.1% trifluoroacetic acid) and B=$CH_3CN$ (0.1% trifluoroacetic acid) pumped at 25 mL/min to afford the title compound (12.2 mg, 55%).

LC/MS: 540.4 Rt: 1.40 min.

Example 62

3-{1-[(3-{[2-hydroxy-1-(hydroxymethyl)ethyl]amino}propyl)sulfonyl]-4-piperidinyl}-5-phenyl-1H-indazole-7-carboxamide

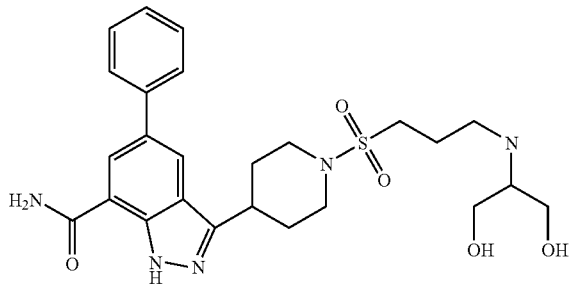 [SMILES: NC(=O)c1cc(-c2ccccc2)cc2c(C3CCN(S(=O)(=O)CCCNC(CO)CO)CC3)n[nH]c12]

To a solution of 3-{1-[(3-chloropropyl)sulfonyl]-4-piperidinyl}-5-phenyl-1H-indazole-7-carboxamide i (Intermediate 22) (19 mg, 0.0413 mmol) in DMF (1 mL) was added $K_2CO_3$ (25 mg, 0.165 mmol), 2-amino-1,3-propanediol (20 mg, 0.2065 mmol) and sodium iodide (1.0 mg). The reaction mixture was heated to 120° C. for 14 hrs. The solution was filtered and concentrated. The residue was purified by using a Gilson semi-preparative HPLC system with a YMC ODS-A (C-18) column 50 mm by 20 mm ID, eluting with 10% B to 80% B in 10 min, hold for 1 min where A=$H_2O$ (0.1% trifluoroacetic acid) and B=$CH_3CN$ (0.1% trifluoroacetic acid) pumped at 25 mL/min to afford the title compound (5.8 mg, 27%).

LC/MS: 516.4 Rt: 1.43 min.

Example 63

3-[1-(ethylsulfonyl)-4-piperidinyl]-5-{3-[(methylamino)methyl]phenyl}-1H-indazole-7-carboxamide

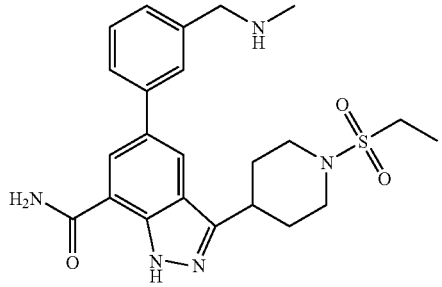 [SMILES: CCS(=O)(=O)N1CCC(c2n[nH]c3c(C(N)=O)cc(-c4cccc(CNC)c4)cc23)CC1]

To a solution of 3-[1-(ethylsulfonyl)-4-piperidinyl]-5-(3-formylphenyl)-1H-indazole-7-carboxamide (Intermediate 24) (30 mg, 0.068 mmol) in DCM/MeOH (1 mL/1 mL) was added 2.0 M in THF methyl amine (0.2 mL) and one drop of acetic acid. The reaction mixture was stirred at room temperature for 2 hrs before sodium borohydride (16 mg, 0.408 mmol) was added. The reaction mixture was stirred at room temperature for 1 hrs and concentrated. The residue was purified by using a Gilson semi-preparative HPLC system with a YMC ODS-A (C-18) column 50 mm by 20 mm ID, eluting with 10% B to 80% B in 10 min, hold for 1 min where A=$H_2O$ (0.1% trifluoroacetic acid) and B=$CH_3CN$ (0.1% trifluoroacetic acid) pumped at 25 mL/min to afford the title compound (13 mg, 42%).

LC/MS: 456.2 Rt: 1.34 min.

Example 64

5-{3-[(ethylamino)methyl]phenyl}-3-[1-(ethylsulfonyl)-4-piperidinyl]-1H-indazole-7-carboxamide

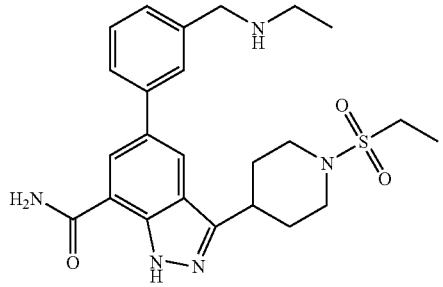 [SMILES: CCNCc1cccc(-c2cc(C(N)=O)c3[nH]nc(C4CCN(S(=O)(=O)CC)CC4)c3c2)c1]

To a solution of 3-[1-(ethylsulfonyl)-4-piperidinyl]-5-(3-formylphenyl)-1H-indazole-7-carboxamide (Intermediate 24) (30 mg, 0.068 mmol) in DCM/MeOH (1 mL/1 mL) was added 2.0 M in THF ethyl amine (0.2 mL) and one drop of acetic acid. The reaction mixture was stirred at room temperature for 2 hrs before sodium borohydride (16 mg, 0.408 mmol) was added. The reaction mixture was stirred at room temperature for 1 hrs and concentrated. The residue was purified by using a Gilson semi-preparative HPLC system with a YMC ODS-A (C-18) column 50 mm by 20 mm ID, eluting with 10% B to 80% B in 10 min, hold for 1 min where A=$H_2O$ (0.1% trifluoroacetic acid) and B=$CH_3CN$ (0.1% trifluoroacetic acid) pumped at 25 mL/min to afford the title compound (5.1 mg, 16%).

LC/MS: 470.2 Rt: 1.56 min.

Example 65

5-[(methylamino)methyl]-3-(1-{[3-(methyloxy)propyl]sulfonyl}-4-piperidinyl)-1H-indazole-7-carboxamide

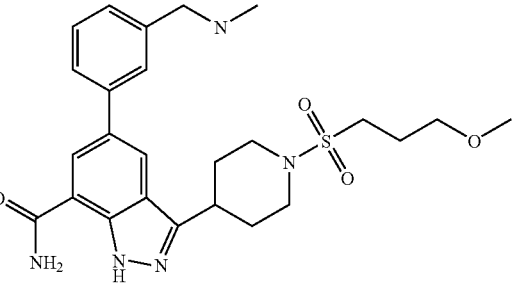

To a solution of 5-(hydroxymethyl)-3-(1-{[3-(methyloxy)propyl]sulfonyl}-4-piperidinyl)-1H-indazole-7-carboxamide (Intermediate 26) (18 mg, 0.04 mmol) in THF (15 mL) was added $MnO_2$ (120 mg, 1.18 mmol). The reaction mixture was stirred at room temperature overnight and filtered. The filtrate was concentrated under reduced pressure to give the crude aldehyde compound, which was used in the next step without further purification.

To a solution of the above aldehyde (8 mg, 0.017 mmol) in DCM/MeOH (1 mL, 1 mL) were added methyl amine (50 uL, 0.106 mmol) and one drop of acetic acid. The reaction mixture was stirred at room temperature for 2 hrs and then sodium borohydride (4.0 mg, 0.106 mmol) was added. After stirring at room temperature for 1 hr, the reaction mixture was concentrated at reduced pressure. The residue was dissolved in DMSO (0.9 mL) and was purified by using a Gilson semi-preparative HPLC system with a YMC ODS-A (C-18) column 50 mm by 20 mm ID, eluting with 10% B to 80% B in 10 min, hold for 1 min where A=H$_2$O (0.1% trifluoroacetic acid) and B=CH$_3$CN (0.1% trifluoroacetic acid) pumped at 25 mL/min to afford the title compound (2.6 mg, 31%).

LC/MS: 500.6 Rt: 1.42 min.

Example 66

1,1-dimethylethyl 4-(7-(aminocarbonyl)-5-{3-[(methylsulfonyl)amino]phenyl}-1H-indazol-3-yl)-1-piperidinecarboxylate

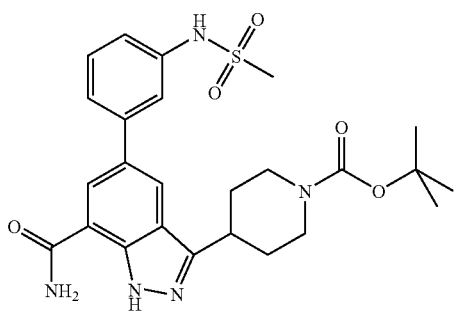 [SMILES: CC(C)(C)OC(=O)N1CCC(c2n[nH]c3c(C(N)=O)cc(-c4cccc(NS(C)(=O)=O)c4)cc23)CC1]

A mixture of 1,1-dimethylethyl 4-[7-(aminocarbonyl)-5-bromo-1H-indazol-3-yl]-1-piperidinecarboxylate (Intermediate 5) (30 mg, 0.07 mmols), {3-[(methylsulfonyl)amino]phenyl}boronic acid (46 mg, 0.21 mmols), cesium carbonate (150 mg), and Pd(PPh$_3$)$_4$ (10 mg) in dioxane/water (3/1, 4 mL) was heated at 160° C. for 2700 secs. (microwave irradiation). The resulting mixture was concentrated, redissolved in methylene chloride and filtered. The filtrate was concentrated and used in the next step without further purification.

LC/MS: 514 Rt. 2.01 min.

Example 67

5-{3-[(methylsulfonyl)amino]phenyl}-3-(4-piperidinyl)-1H-indazole-7-carboxamide

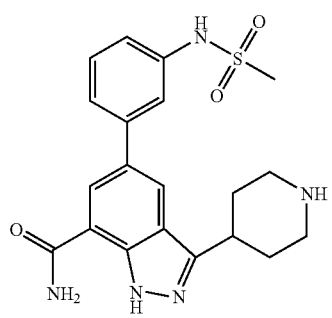 [SMILES: CS(=O)(=O)Nc1cccc(-c2cc(C(N)=O)c3[nH]nc(C4CCNCC4)c3c2)c1]

Following the general procedure of Example 2, a mixture of 1,1-dimethylethyl 4-(7-(aminocarbonyl)-5-{3-[(methylsulfonyl)amino]phenyl}-1H-indazol-3-yl)-1-piperidine-carboxylate (Example 66) (0.07 mmols) and concentrated HCl (1 mL) in dioxane/water (3/1, 10 mL) was reacted to give the crude amine hydrochloride salt, which was used in the next step without further purification.

LC/MS: 414 Rt. 1.33 min.

Example 68

1,1-dimethylethyl 4-[5-[3-(acetylamino)phenyl]-7-(aminocarbonyl)-1H-indazol-3-yl]-1-piperidinecarboxylate

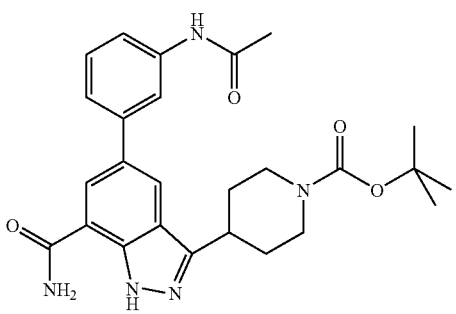 [SMILES: CC(=O)Nc1cccc(-c2cc(C(N)=O)c3[nH]nc(C4CCN(C(=O)OC(C)(C)C)CC4)c3c2)c1]

Following the general procedure of Example 66, a mixture of 1,1-dimethylethyl 4-[7-(aminocarbonyl)-5-bromo-1H-indazol-3-yl]-1-piperidinecarboxylate (Intermediate 5) (30 mg, 0.07 mmols), [3-(acetylamino)phenyl]boronic acid (38 mg, 0.21 mmols), cesium carbonate (150 mg), and Pd(PPh$_3$)$_4$ (10 mg) in dioxane/water (3/1, 4 mL) were reacted to give the title compound.

LC/MS: 478 Rt. 1.91 min.

Example 69

5-[3-(acetylamino)phenyl]-3-(4-piperidinyl)-1H-indazole-7-carboxamide

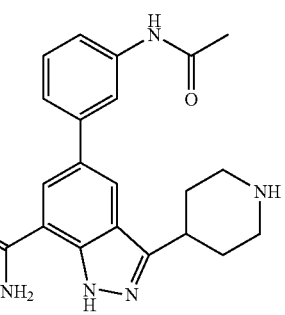

Following the general procedure of Example 2, a mixture of 1,1-dimethylethyl 4-[5-[3-(acetylamino)phenyl]-7-(aminocarbonyl)-1H-indazol-3-yl]-1-piperidinecarboxylate (Example 68) (0.07 mmols) and concentrated HCl (1 mL) in dioxane/water (3/1, 10 mL) was reacted to give the crude amine hydrochloride salt, which was used in the next step without further purification.

LC/MS: 378 Rt. 1.29 min.

Example 70

1,1-dimethylethyl 4-[5-[4-(acetylamino)phenyl]-7-(aminocarbonyl)-1H-indazol-3-yl]-1-piperidinecarboxylate

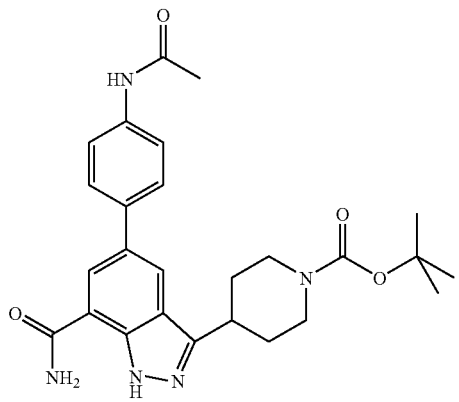 [SMILES: CC(=O)Nc1ccc(-c2cc(C(N)=O)c3[nH]nc(C4CCN(C(=O)OC(C)(C)C)CC4)c3c2)cc1]

Following the general procedure of Example 66, a mixture of 1,1-dimethylethyl 4-[7-(aminocarbonyl)-5-bromo-1H-indazol-3-yl]-1-piperidinecarboxylate (Intermediate 5) (30 mg, 0.07 mmols), N-[4-(4,4,5,5-tetramethyl-1,3,2-dioxaborolan-2-yl)phenyl]acetamide (55 mg, 0.21 mmols), cesium carbonate (150 mg), and Pd(PPh$_3$)$_4$ (10 mg) in dioxane/water (3/1, 4 mL) were reacted to give the title compound.

LC/MS: 478 Rt. 1.95 min.

Example 71

5-[4-(acetylamino)phenyl]-3-(4-piperidinyl)-1H-indazole-7-carboxamide

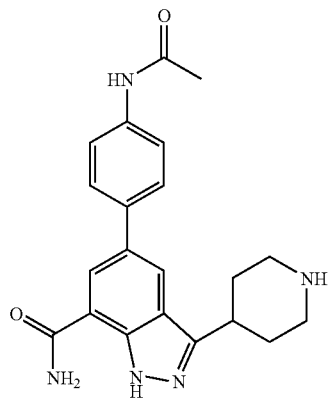 [SMILES: CC(=O)Nc1ccc(-c2cc(C(N)=O)c3[nH]nc(C4CCNCC4)c3c2)cc1]

Following the general procedure of Example 2, a mixture of 1,1-dimethylethyl 4-[5-[4-(acetylamino)phenyl]-7-(aminocarbonyl)-1H-indazol-3-yl]-1-piperidinecarboxylate (Example 70) (0.07 mmols) and concentrated HCl (1 mL) in dioxane/water (3/1, 10 mL) was reacted to give the crude amine hydrochloride salt, which was used in the next step without further purification.

LC/MS: 378 Rt. 1.17 min.

Example 72

1,1-dimethylethyl 4-{7-(aminocarbonyl)-5-[4-(hydroxymethyl)phenyl]-1H-indazol-3-yl}-1-piperidinecarboxylate

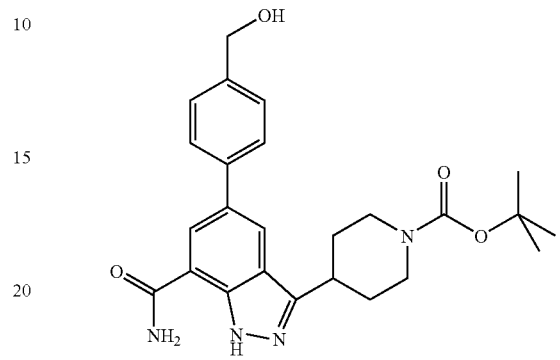

Following the general procedure of Example 66, a mixture of 1,1-dimethylethyl 4-[7-(aminocarbonyl)-5-bromo-1H-indazol-3-yl]-1-piperidinecarboxylate (Intermediate 5) (30 mg, 0.07 mmols), [4-(hydroxymethyl)phenyl]boronic acid (32 mg, 0.21 mmols), cesium carbonate (150 mg), and Pd(PPh$_3$)$_4$ (10 mg) in dioxane/water (3/1, 4 mL) were reacted to give the title compound.

LC/MS: 451 Rt. 2.12 min.

Example 73

5-[4-(hydroxymethyl)phenyl]-3-(4-piperidinyl)-1H-indazole-7-carboxamide

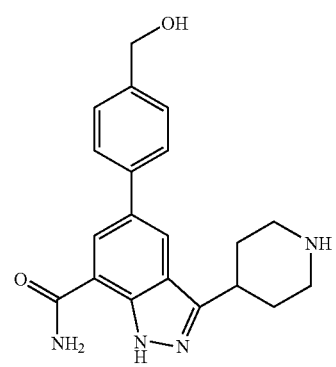 [SMILES: NC(=O)c1cc(-c2ccc(CO)cc2)cc2c(C3CCNCC3)n[nH]c12]

Following the general procedure of Example 2, a mixture of 1,1-dimethylethyl 4-{7-(aminocarbonyl)-5-[4-(hydroxymethyl)phenyl]-1H-indazol-3-yl}-1-piperidinecarboxylate (Example 72) (0.07 mmols) and concentrated HCl (1 mL) in dioxane/water (3/1, 10 mL) was reacted to give the crude amine hydrochloride salt, which was used in the next step without further purification.

LC/MS: 351 Rt. 1.23 min.

Example 74

1,1-dimethylethyl 4-[7-(aminocarbonyl)-5-(1H-pyrazol-4-yl)-1H-indazol-3-yl]-1-piperidinecarboxylate

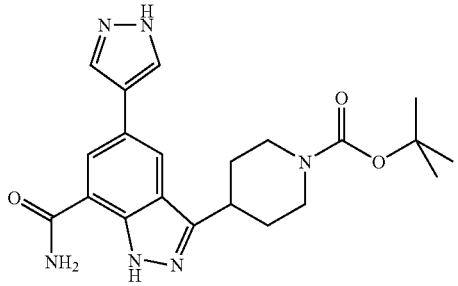 [SMILES: CC(C)(C)OC(=O)N1CCC(c2n[nH]c3c(C(N)=O)cc(-c4cn[nH]c4)cc23)CC1]

Following the general procedure of Example 66, a mixture of 1,1-dimethylethyl 4-[7-(aminocarbonyl)-5-bromo-1H-indazol-3-yl]-1-piperidinecarboxylate (Intermediate 5) (30 mg, 0.07 mmols), 4-(4,4,5,5-tetramethyl-1,3,2-dioxaborolan-2-yl)-1H-pyrazole (41 mg, 0.21 mmols), cesium carbonate (150 mg), and Pd(PPh$_3$)$_4$ (10 mg) in dioxane/water (3/1, 4 mL) were reacted to give the title compound.

LC/MS: 411 Rt. 1.71 min.

Example 75

3-(4-piperidinyl)-5-(1H-pyrazol-4-yl)-1H-indazole-7-carboxamide

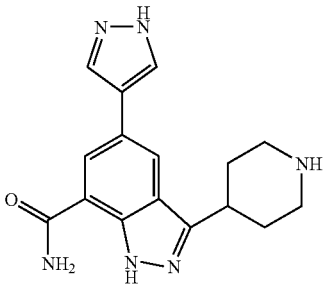 [SMILES: NC(=O)c1cc(-c2cn[nH]c2)cc2c(C3CCNCC3)n[nH]c12]

Following the general procedure of Example 2, a mixture of 1,1-dimethylethyl 4-[7-(aminocarbonyl)-5-(1H-pyrazol-4-yl)-1H-indazol-3-yl]-1-piperidinecarboxylate (Example 74) (0.07 mmols) and concentrated HCl (1 mL) in dioxane/water (3/1, 10 mL) was reacted to give the crude amine hydrochloride salt which was used in the next step without further purification.

LC/MS: 311 Rt. 1.09 min.

Example 76

5-phenyl-3-{1-[(2,2,2-trifluoroethyl)sulfonyl]-4-piperidinyl}-1H-indazole-7-carboxamide

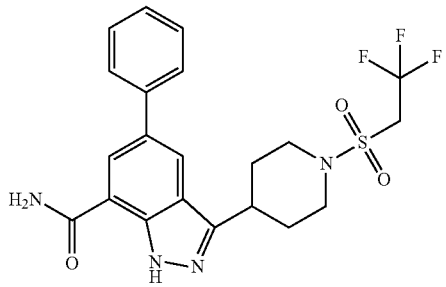 [SMILES: NC(=O)c1cc(-c2ccccc2)cc2c(C3CCN(S(=O)(=O)CC(F)(F)F)CC3)n[nH]c12]

This compound was prepared in a fashion analogous to the procedure described in Example 3. Thus, 5-phenyl-3-(4-piperidinyl)-1H-indazole-7-carboxamide hydrochloride (Example 2) (0.030 g, 0.07 mmol) was reacted with 2,2,2-trifluoroethanesulfonyl chloride (0.015 mL, 0.105 mmol) in the presence of triethylamine (0.04 mL, 0.28 mmol) in DMF (2 mL) to give 6.7 mg of white solid.

LC/MS-M+H 467

Assays and Biological Data

IKK2 Assay

Recombinant human IKKβ (residues 1-737) was expressed in baculovirus as a C-terminal GST-tagged fusion protein, and its activity was assessed using a time-resolved fluorescence resonance energy transfer (TR-FRET) assay. Briefly, IKK2 (5 nM final) diluted in assay buffer (50 mM HEPES, 10 mM MgCl$_2$, 1 mM CHAPS pH 7.4 with 1 mM DTT and 0.01% w/v BSA) was added to wells containing various concentrations of compound or DMSO vehicle (3% final). The reaction was initiated by the addition of GST-IκBα substrate (25 nM final)/ATP (1 μM final), in a total volume of 30 μl. The reaction was incubated for 30 minutes at room temperature, then terminated by the addition of 15 μl of 50 mM EDTA. Detection reagent (15 μl) in buffer (100 mM HEPES pH 7.4, 150 mM NaCl and 0.1% w/v BSA) containing antiphosphoserine-IκBα-32/36 monoclonal antibody 12C2 (Cell Signalling Technology, Beverly Mass., USA) labeled with W-1024 europium chelate (Wallac OY, Turku, Finland), and an APC-labeled anti-GST antibody (Prozyme, San Leandro, Calif., USA) was added and the reaction was further incubated for 60 minutes at room temperature. The degree of phosphorylation of GST-IκBα was measured using a Packard Discovery plate reader (Perkin-Elmer Life Sciences, Pangbourne, UK) as a ratio of specific 665 nm energy transfer signal to reference europium 620 nm signal.

Results

Many of the compounds exemplified above were tested for activity against IKK2, and all compounds tested against IKK2 were found to be inhibitors of IKK2. All tested compounds had a pIC$_{50}$ of 5.0 or greater.

What is claimed is:
1. A compound according to Formula (I):

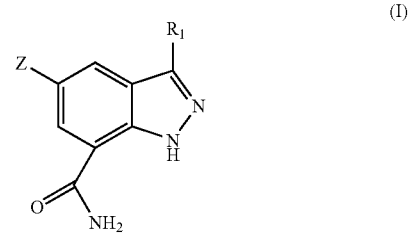

wherein:
Z is optionally substituted thienyl
wherein the thienyl is optionally substituted with one or more substituent independently selected from the group consisting of: halo, optionally substituted C$_1$-C$_6$ alkyl, optionally substituted C$_1$-C$_6$ haloalkyl, optionally substituted heterocycloalkyl, CN, N(Rb)SO$_2$Re, N(Rb)C(O)Ra, C(O)NRaRb, C(O)NRxRy, SO$_2$NRaRb, SO$_2$NRxRy, ORc, N(Rb)C(O)NRaRb, N(Rb)C(O)NRxRy, N(Rb)C(O)ORd, where said C$_1$-C$_6$ alkyl and C$_1$-C$_6$ haloalkyl are optionally substituted with one or more substituent selected from the group consisting of:

NRaRb, $C_3$-$C_6$ cycloalkyl, ORc, phenyl, and heterocycloalkyl optionally substituted with one or two $C_1$-$C_6$ alkyl groups;

R1 is —WX;

W is a bond; and

X is optionally substituted piperidinyl optionally substituted with one or more substituent independently selected from the group consisting of: halo, optionally substituted $C_1$-$C_6$ alkyl, optionally substituted $C_1$-$C_6$ haloalkyl, ORc, C(O)Rg, C(O)ORf, N(Rb)$SO_2$Re, N(Rb)C(O)Ra, C(O)NRaRb, $SO_2$NRaRb, $SO_2$Re, and heterocycloalkyl, where said $C_1$-$C_6$ alkyl and $C_1$-$C_6$ haloalkyl are optionally substituted with one phenyl group;

each Ra is independently selected from the group consisting of: H, optionally substituted $C_1$-$C_3$ alkyl, optionally substituted phenyl, optionally substituted heteroaryl, optionally substituted $C_3$-$C_7$ cycloalkyl, and optionally substituted heterocycloalkyl, where said $C_1$-$C_3$ alkyl is optionally substituted with one or more substituent selected from the group consisting of: halo, ORc, $C_1$-$C_6$ haloalkyl, phenyl, and heteroaryl; and where said phenyl, heteroaryl, $C_3$-$C_7$ cycloalkyl, and heterocycloalkyl are optionally substituted with one or more substituent selected from the group consisting of: halo, ORc, $C_1$-$C_6$ alkyl, and $C_1$-$C_6$ haloalkyl;

each Rb is independently selected from the group consisting of: H and optionally substituted $C_1$-$C_3$ alkyl, where said $C_1$-$C_3$ alkyl is optionally substituted with one or more ORc groups;

each Rc is independently selected from the group consisting of: H, optionally substituted $C_1$-$C_6$ alkyl, optionally substituted $C_1$-$C_6$ haloalkyl, optionally substituted $C_3$-$C_7$ cycloalkyl, optionally substituted heterocycloalkyl, and optionally substituted aryl, optionally substituted heteroaryl, where said $C_1$-$C_6$ alkyl and $C_1$-$C_6$ haloalkyl are optionally substituted with one or more substituent selected from the group consisting of: $C_3$-$C_6$ cycloalkyl, phenyl, heterocycloalkyl, and heteroaryl; and where said aryl and heteroaryl are optionally substituted with one or more substituent selected from the group consisting of: halo, $C_1$-$C_3$ alkyl, $C_1$-$C_3$ haloalkyl and OH; and where said $C_3$-$C_7$ cycloalkyl and heterocycloalkyl are optionally substituted with one or more $C_1$-$C_3$ alkyl groups;

each Rd is independently optionally substituted $C_1$-$C_3$ alkyl, where said $C_1$-$C_3$ alkyl is optionally substituted with one or more substituent selected from the group consisting of: $C_3$-$C_6$ cycloalkyl; phenyl optionally substituted with one or more substituent selected from the group consisting of: halo, $C_1$-$C_6$ alkyl, and $C_3$-$C_6$ cycloalkyl; and heteroaryl optionally substituted with one or more substituent selected from the group consisting of: halo, $C_1$-$C_6$ alkyl, and $C_3$-$C_6$ cycloalkyl;

each Re is independently selected from the group consisting of: optionally substituted $C_1$-$C_6$ alkyl, optionally substituted phenyl, optionally substituted heteroaryl, optionally substituted $C_5$-$C_7$ cycloalkyl, and optionally substituted heterocycloalkyl, where said $C_1$-$C_6$ alkyl is optionally substituted with one substituent selected from the group consisting of: ORc, trifluoromethyl, phenyl, heteroaryl, heterocycloalkyl optionally substituted with ORc or heterocycloalkyl, and NRaRb; where said phenyl and heteroaryl are optionally substituted with one or more substituent selected from the group consisting of: halo, CN, $C_1$-$C_6$ alkyl, $C_1$-$C_6$ haloalkyl, N(Rb)C(O)Ra, and ORh; and where said $C_5$-$C_7$ cycloalkyl and heterocycloalkyl are optionally substituted with one or more substituent selected from the group consisting of: halo, $C_1$-$C_6$ alkyl optionally substituted with ORc, and $C_3$-$C_6$ cycloalkyl;

each Rf is independently selected from the group consisting of: H and optionally substituted $C_1$-$C_4$ alkyl, where said $C_1$-$C_4$ alkyl is optionally substituted with one or more substituent selected from the group consisting of: $C_3$-$C_6$ cycloalkyl; phenyl optionally substituted with one or more substituent selected from the group consisting of: halo, $C_1$-$C_6$ alkyl, and $C_3$-$C_6$ cycloalkyl; and heteroaryl optionally substituted with one or more substituent selected from the group consisting of: halo, $C_1$-$C_6$ alkyl, and $C_3$-$C_6$ cycloalkyl;

each Rg is independently selected from the group consisting of: optionally substituted $C_1$-$C_3$ alkyl, optionally substituted phenyl, optionally substituted heteroaryl, optionally substituted $C_3$-$C_7$ cycloalkyl, and optionally substituted heterocycloalkyl, where said $C_1$-$C_3$ alkyl is optionally substituted with one or more substituent selected from the group consisting of: halo and $C_{1-6}$ haloalkyl; and where said phenyl, heteroaryl, $C_3$-$C_7$ cycloalkyl, and heterocycloalkyl are optionally substituted with one or more substituent selected from the group consisting of: halo, $C_{1-6}$ alkyl, and $C_1$-$C_6$ haloalkyl;

each Rh is independently selected from the group consisting of: H, $C_1$-$C_6$ alkyl, and $C_1$-$C_6$ haloalkyl; and Rx and Ry taken together with the nitrogen atom to which they are attached form a ring having from 5 to 7 member atoms wherein said ring optionally contains one additional heteroatom as a member atom, said ring is saturated or unsaturated but not aromatic, and said ring is optionally substituted with one or two $C_1$-$C_3$ alkyl substituent;

or a pharmaceutically-acceptable salt thereof.

2. A compound according to claim 1 wherein X is optionally substituted piperidinyl.

3. A compound according to claim 2 wherein X is piperidinyl substituted with C(O)Rg, C(O)ORf, or $SO_2$Re.

4. A pharmaceutical composition comprising a compound according to claim 1 and one or more pharmaceutically-acceptable excipient.

5. A compound selected from:
3-[1-(ethylsulfonyl)-4-piperidinyl]-5-(2-thienyl)-1H-indazole-7-carboxamide;
3-[1-(ethylsulfonyl)-4-piperidinyl]-5-(3-thienyl)-1H-indazole-7-carboxamide;
3-(1-{[3-(1-pyrrolidinyl)propyl]sulfonyl}-4-piperidinyl)-5-(2-thienyl)-1H-indazole-7-carboxamide;
3-(1-{[3-(dimethylamino)propyl]sulfonyl}-4-piperidinyl)-5-(2-thienyl)-1H-indazole-7-carboxamide;
3-(1-{[3-(1-pyrrolidinyl)propyl]sulfonyl}-4-piperidinyl)-5-(3-thienyl)-1H-indazole-7-carboxamide;
3-(1-{[3-(dimethylamino)propyl]sulfonyl}-4-piperidinyl)-5-(3-thienyl)-1H-indazole-7-carboxamide;
3-(1-{[3-(4-morpholinyl)propyl]sulfonyl}-4-piperidinyl)-5-(2-thienyl)-1H-indazole-7-carboxamide; and
3-(1-{[3-(4-morpholinyl)propyl]sulfonyl}-4-piperidinyl)-5-(3-thienyl)-1H-indazole-7-carboxamide; or a pharmaceutically acceptable salt thereof.

* * * * *